United States Patent
Vujanovic et al.

(10) Patent No.: US 10,543,264 B2
(45) Date of Patent: Jan. 28, 2020

(54) CANCER PREVENTION AND THERAPY BY INHIBITING SOLUBLE TUMOR NECROSIS FACTOR

(71) Applicant: University of Pittsburgh—Of the Commonwealth System of Higher Education, Pittsburgh, PA (US)

(72) Inventors: Nikola L. Vujanovic, Pittsburgh, PA (US); Lazar Vujanovic, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 54 days.

(21) Appl. No.: 15/776,061

(22) PCT Filed: Dec. 14, 2016

(86) PCT No.: PCT/US2016/066552
§ 371 (c)(1),
(2) Date: May 14, 2018

(87) PCT Pub. No.: WO2017/106278
PCT Pub. Date: Jun. 22, 2017

(65) Prior Publication Data
US 2019/0336591 A1    Nov. 7, 2019

Related U.S. Application Data

(60) Provisional application No. 62/269,839, filed on Dec. 18, 2015.

(51) Int. Cl.
*G01N 31/00* (2006.01)
*G01N 33/53* (2006.01)
*A61K 39/00* (2006.01)
*A61K 38/20* (2006.01)
*C07K 14/525* (2006.01)
*A61P 35/00* (2006.01)
*A61K 45/06* (2006.01)

(52) U.S. Cl.
CPC .. *A61K 39/001117* (2018.08); *A61K 38/2013* (2013.01); *A61K 38/2046* (2013.01); *A61K 38/2086* (2013.01); *A61K 39/00114* (2018.08); *A61K 39/001139* (2018.08); *A61P 35/00* (2018.01); *C07K 14/525* (2013.01); *A61K 45/06* (2013.01); *A61K 2039/57* (2013.01)

(58) Field of Classification Search
None
See application file for complete search history.

(56) References Cited

U.S. PATENT DOCUMENTS

| | | | | |
|---|---|---|---|---|
| 7,446,174 | B2 * | 11/2008 | Desjarlais | A61K 38/191 435/335 |
| 7,662,367 | B2 * | 2/2010 | Desjarlais | A61K 38/191 424/85.1 |
| 9,060,978 | B2 * | 6/2015 | Binette | A61K 45/06 |
| 2010/0197751 | A1 | 8/2010 | Kerwin et al. | |
| 2012/0189619 | A1 | 7/2012 | Binette | |
| 2013/0022605 | A1 | 1/2013 | Brewis et al. | |
| 2013/0071350 | A1 | 3/2013 | Lentz | |
| 2013/0164287 | A1 | 6/2013 | Finck | |

FOREIGN PATENT DOCUMENTS

WO    WO 2014/040076 A1    3/2014

OTHER PUBLICATIONS

Gray-Schopfer et al., "Tumor necrosis factor-α blocks apoptosis in melanoma cells when BRAF signaling is inhibited," *Cancer Research* 67(1): 122-129 (Jan. 1, 2007).
International Search Report from PCT Application No. PCT/US2016/066552, 11 pages (dated Feb. 15, 2017).
Kalliolias and Ivashkiv, "TNF biology, pathogenic mechanisms and emerging therapeutic strategies," *Nature Review Rheumatology* 12(1): 49-62 (ePub Dec. 10, 2015).
Kontermann et al., "Antagonists of TNF action: clinical experience and new developments," *Expert Opinion on Drug Discovery* 4(3):279-292 (Mar. 2009)(Abstract).
Smith et al., "The immune microenvironment confers resistance to MAPK pathway inhibitors through macrophage-derived TNFα," *Cancer Discovery* 4: 1214-1229 (ePub Sep. 30, 2014).
Steed et al., "Inactivation of TNF signaling by rationally designed dominant-negative TNF variants," *Science* 301(5641): 1895-1898 (Sep. 2003)(Abstract).
Written Opinion from PCT Application No. PCT/US2016/066552, 5 pages (dated Feb. 15, 2017).

* cited by examiner

*Primary Examiner* — Lisa V Cook
(74) *Attorney, Agent, or Firm* — Klarquist Sparkman, LLP

(57) ABSTRACT

Methods are disclosed for inhibiting the development of a tumor in a subject. The methods include administering to a subject a therapeutically effective amount of a dominant negative tumor necrosis factor (DN-TNF)-α protein and/or a nucleic acid encoding the DN-TNF-α protein. The DN-TNF-α protein and/or a nucleic acid encoding the DN-TNF-α protein can be administered alone or in combination with other agents.

25 Claims, 13 Drawing Sheets
Specification includes a Sequence Listing.

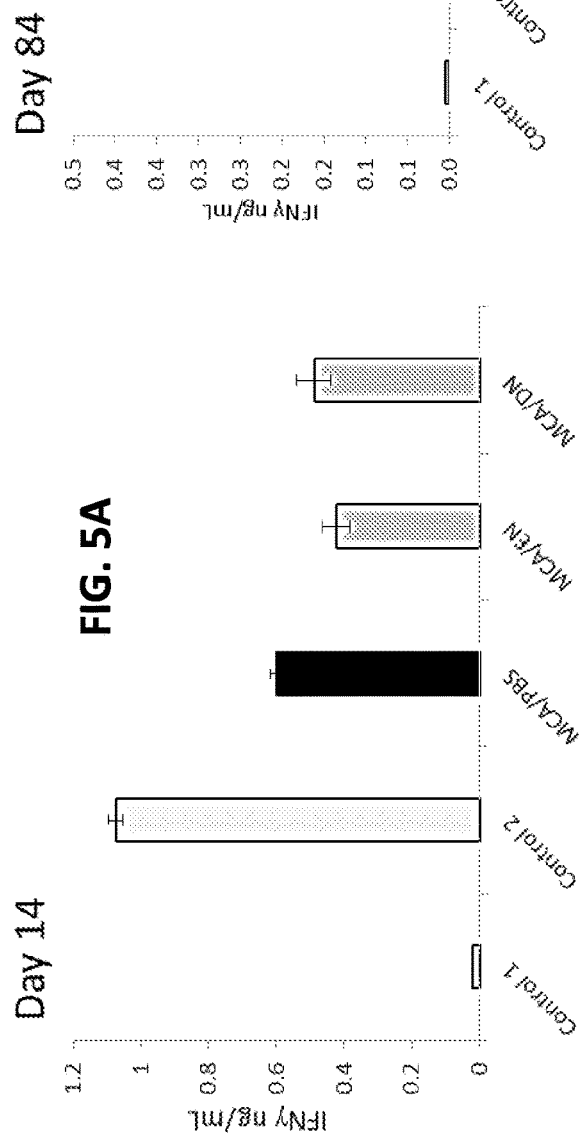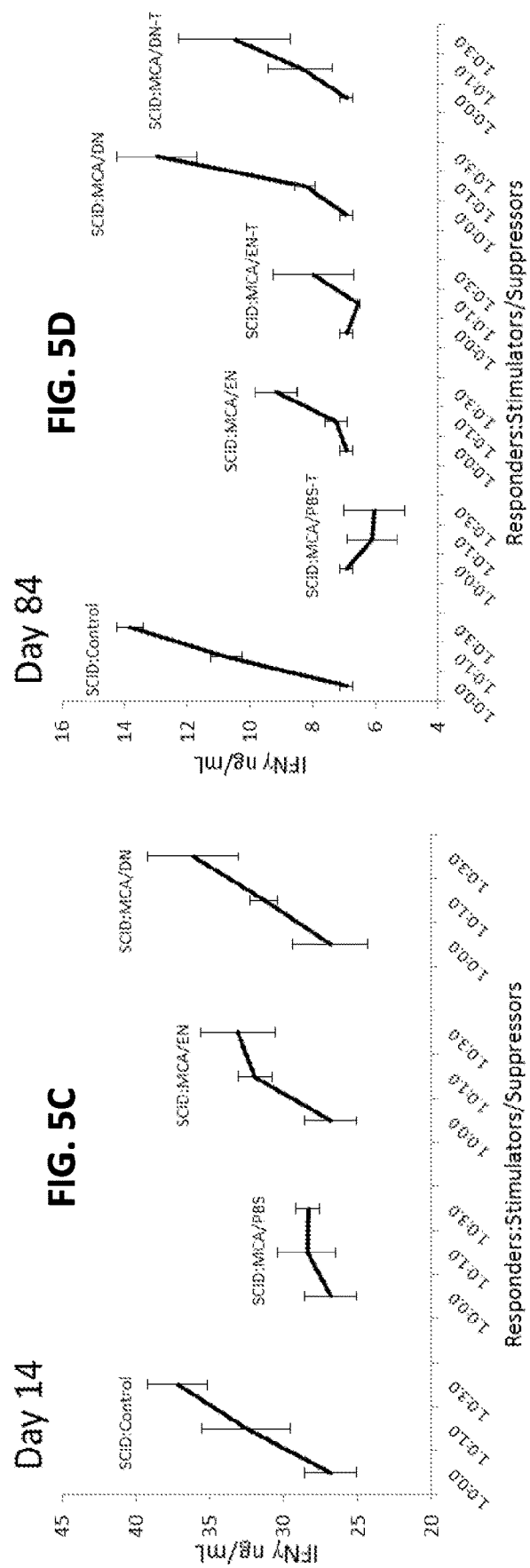

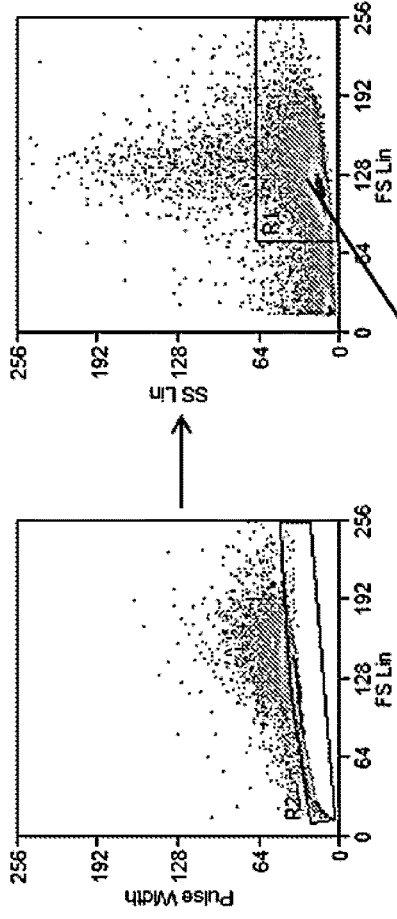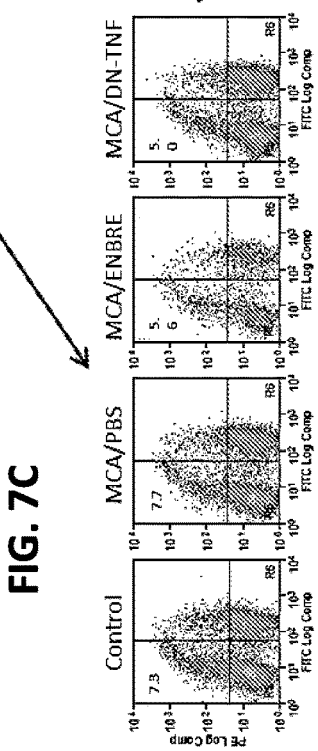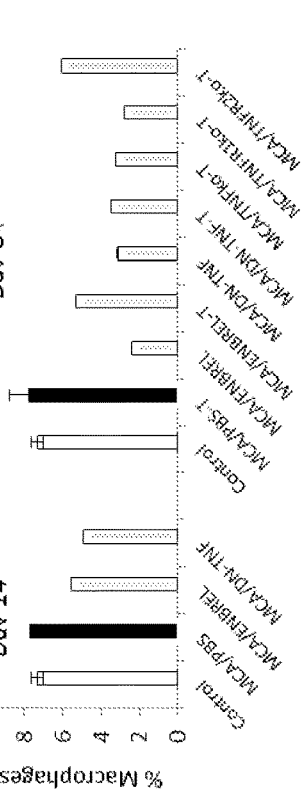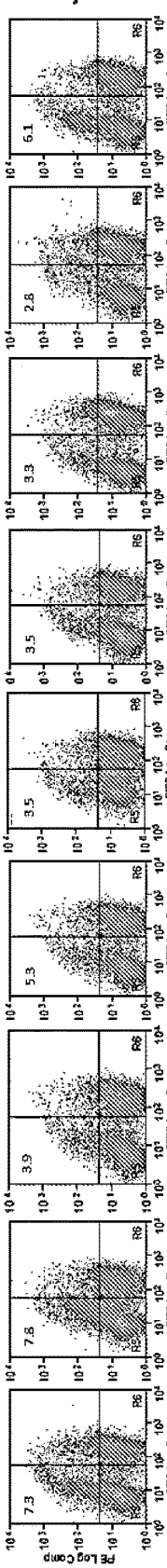

FIG. 11

MRSSSRTPSDKPVAHVVANPQAEGQLQWLNCRANALLANGVELRDNQLVVPSEGLYLIYSQVLFKGQGVPSTHVLLT

VRSSSRTPSDKPVAHVVANPQAEGQLQWLNRRANALLANGVELRDNQLVVPSEGLYLIYSQVLFKGQGCPSTHVLLT

HTISRIAVSHQTKVNLLSAIKSPAQRETPEGAEAKPWYEPIYLGGVFQLEKGDRLSAEINRPDYLDFRESGQVYFGIIAL

HTISRIAVSYQTKVNLLSAIKSPCQRETPEGAEAKPWYEPIYLGGVFQLEKGDRLSAEINRPDYLDFAESGQVYFGIIAL

SEQUENCE LISTING

```
<160> NUMBER OF SEQ ID NOS: 3

<210> SEQ ID NO 1
<211> LENGTH: 157
<212> TYPE: PRT
<213> ORGANISM: Homo sapiens

<400> SEQUENCE: 1

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 2
<211> LENGTH: 157
<212> TYPE: PRT
<213> ORGANISM: Artificial Sequence
<220> FEATURE:
```

<223> OTHER INFORMATION: dominant-negative tumor necrosis factor alpha

<400> SEQUENCE: 2

```
Met Arg Ser Ser Ser Arg Thr Pro Ser Asp Lys Pro Val Ala His Val
1               5                   10                  15
Val Ala Asn Pro Gln Ala Glu Gly Gln Leu Gln Trp Leu Asn Cys Arg
            20                  25                  30
Ala Asn Ala Leu Leu Ala Asn Gly Val Glu Leu Arg Asp Asn Gln Leu
        35                  40                  45
Val Val Pro Ser Glu Gly Leu Tyr Leu Ile Tyr Ser Gln Val Leu Phe
    50                  55                  60
Lys Gly Gln Gly Val Pro Ser Thr His Val Leu Leu Thr His Thr Ile
65                  70                  75                  80
Ser Arg Ile Ala Val Ser His Gln Thr Lys Val Asn Leu Leu Ser Ala
                85                  90                  95
Ile Lys Ser Pro Ala Gln Arg Glu Thr Pro Glu Gly Ala Glu Ala Lys
            100                 105                 110
Pro Trp Tyr Glu Pro Ile Tyr Leu Gly Gly Val Phe Gln Leu Glu Lys
        115                 120                 125
Gly Asp Arg Leu Ser Ala Glu Ile Asn Arg Pro Asp Tyr Leu Asp Phe
    130                 135                 140
Arg Glu Ser Gly Gln Val Tyr Phe Gly Ile Ile Ala Leu
145                 150                 155
```

<210> SEQ ID NO 3
<211> LENGTH: 474
<212> TYPE: DNA
<213> ORGANISM: Artificial Sequence
<220> FEATURE:
<223> OTHER INFORMATION: nucleic acid encoding dominant-negative tumor necrosis factor alpha

<400> SEQUENCE: 3

```
atgcgctcct cctcccgcac tccgtccgac aaaccggtag ctcacgtagt agctaacccg      60
caggctgaag gtcagctgca gtggctgaac tgccgcgcta acgctctgct ggctaacggt     120
gtagaactgc gcgacaacca gctggtagta ccgtccgaag gtctgtacct gatctactcc     180
caggtactgt tcaaaggtca gggtgttccg tccactcacg tactgctcac tcacactatc     240
tcccgcatcg ctgtatccca ccagactaaa gtaaacctgc tgtccgctat caaatccccg     300
gcgcagcgcg aaactccgga aggtgctgaa gctaaaccgt ggtacgaacc gatctacctg     360
ggtggtgtat tccagctgga aaaaggtgac cgcctgtccg ctgaaatcaa ccgcccggac     420
tacctggact tccgcgaatc cggtcaggta tacttcggta tcatcgctct gtaa          474
```

CANCER PREVENTION AND THERAPY BY INHIBITING SOLUBLE TUMOR NECROSIS FACTOR

CROSS REFERENCE TO RELATED APPLICATION

This application is a § 371 U.S. national stage of International Application No. PCT/US2016/066552, filed Dec. 14, 2016, which was published in English under PCT Article 21(2), and which claims the benefit of U.S. Provisional Application No. 62/269,839, filed Dec. 18, 2015, which is incorporated by reference herein.

ACKNOWLEDGMENT OF GOVERNMENT SUPPORT

This invention was made with government support under grant number DE017150 awarded by the National Institutes of Health (NIH); the government has certain rights in the invention.

FIELD

This relates to the field of cancer, specifically to the exclusion of soluble tumor necrosis factor (TNF), in order to inhibit the development of cancer in a subject.

BACKGROUND

Tumor necrosis factor (TNF) is produced as transmembrane and soluble molecules (Wallach et al., Ann Rev Immunol 1999; 17:331-67; Wajant et al., Cell Death Differ 2003; 10:45-65). Transmembrane TNF (tmTNF) is expressed on the cell membrane as functional homotrimers composed of 26 kDa type-II protomers. Soluble TNF (sTNF) is also a homotrimer, but constituted of 17 kDa tmTNF-protomer-extracellular-domain residue produced by TNF-alpha-converting enzyme (TACE, ADAM-17) shedding. TNF is mainly produced by activated macrophages. TNF mediates a number of vital functions, including structural and functional organization of secondary lymphoid organs, apoptosis and antitumor activity, inhibition of viral replication, immunoregulation and inflammation. TNF also plays important roles in pathogenesis of autoimmune diseases, acute phase reaction, septic shock, fever and cachexia. These diverse functions are induced via cognate interactions between the two TNF forms and two transmembrane receptors, TNF receptor type-1 (TNFR1, TNFRSF1A, p55/60, CD120a) and TNF receptor type-2 (TNFR2, TNFRSF1B, p75/80, CD120b). The receptors have structurally distinct intracellular domains and activate different signaling pathways. It is suggested that TNFR1 and TNFR2 are preferentially activated by sTNF and tmTNF, respectively (Wallach et al., Ann Rev Immunol 1999; 17:331-67; Wajant et al., Cell Death Differ 2003; 10:45-65).

Millions of people die from cancer every year worldwide; cancer is the second leading cause of mortality in the United States. The American Cancer Society reports that, in the United States alone, cancer causes the death of well over a half-million people annually, with over 1.2 million new cases diagnosed per year. As deaths from cancer generally are increasing, it has been predicted that cancer will become the leading cause of death.

Cancer is an abnormal state in which uncontrolled proliferation of one or more cell populations interferes with normal biological functioning. The proliferative changes are usually accompanied by changes in cellular properties, including reversion to a less differentiated state and an increase in proliferative capacity. The in vitro correlate of cancer is called cellular transformation. Transformed cells generally display several or all of the following properties: spherical morphology, expression of fetal antigens, growth-factor independence, lack of contact inhibition, anchorage-independence, and growth to high density. A need remains for methods for the treatment and prevention of cancer.

SUMMARY

It is disclosed herein that dominant-negative tumor necrosis factor (DN-TNF)-α decreases tumor incidence and growth, and prolongs survival of subjects at risk for developing tumors. In addition, methods are disclosed for inhibiting the development of a tumor in a subject. The methods include administering to a subject, such as a subject at risk of developing a tumor or a subject with a tumor, a therapeutically effective amount of a dominant negative tumor necrosis factor (DN-TNF)-α protein, and/or a nucleic acid encoding the DN-TNF-α protein. The DN-TNF-α protein or nucleic acid encoding the DN-TNF-α protein can be administered alone or in combination with other agents.

The subject can have a benign or malignant tumor. In some embodiments, the tumor is colon cancer, lung cancer, prostate cancer, breast cancer Kaposi's sarcoma, liver cancer or melanoma.

In specific non-limiting examples, the DN-TNF-α protein comprises the amino acid sequence set forth as SEQ ID NO: 2. In other non-limiting examples, the DN-TNF-α protein is PEGylated.

The foregoing and other objects, features, and advantages of the invention will become more apparent from the following detailed description, which proceeds with reference to the accompanying figures.

BRIEF DESCRIPTION OF THE DRAWINGS

FIG. 1A: Wild-type C57BL/6 mice were injected subcutaneously (s.c.) with MCA as described in Example 1. The MCA-injected mice were randomized into 3 groups of 15 mice. The control-group mice were injected intraperitoneally (i.p.) with phosphate buffered saline (PBS) (0.5 mL). The two other groups mice were injected i.p. with either etanercept (ENBREL®) or XPRO™ 1595 (DN-TNF) (200 µg/0.5 mL PBS/mouse), respectively. The injections of PBS, ENBREL and DN-TNF were performed twice a week, for 12 weeks, starting on the day of MCA injection. FIGS. 1B, 1C and 1D: Twenty wild-type, 10 TNF-deficient (TNFko), 10 TNFR1-deficient (TNFR1ko) and 10 TNFR2-deficient (TNFR2ko) C57BL/6 mice were injected with MCA, as described above. Ten of the MCA-injected wild-type mice were also injected i.p. with PBS, while the other 10 mice were injected with XPRO™ 1595 biologic. The MCA-injected gene-deficient mice were left untreated. MCA-injections and treatments were performed as described in FIG. 1A. FIGS. 1A and 1B present the cumulative tumor incidence. FIG. 1C presents the individual tumor sizes and their means (thick lines). FIG. 1D presents the cumulative survival. The analyses were performed as described in Example 1. In FIG. 1A, the differences of MCA/PBS vs MCA/ENBREL and MCA/DN-TNF, and MCA/ENBREL vs MCA/DN-TNF are significant ($p=0.009$, $p<0.00005$, and $p=0.027$ respectively). In FIG.

1B, the differences of MCA/PBS vs MCA/DN-TNF, MCA/TNFko and MCA/TNFR1ko; and MCA/TNFR2ko vs MCA/DN-TNF, MCA/TNFko and MCA/TNFR1ko are significant (p=0.0007, p=0.0016 and p=0.031; p=0.0013, p=0.0026, and p=0.029; respectively). In FIG. 1C, the differences of MCA/PBS vs MCA/DN-TNF and MCA/TNFko; MCA/TNFR1ko vs MCA/DN-TNF and MCA/TNFko; and MCA/TNFR2ko vs MCA/DN-TNF and MCA/TNFko are significant (p=0.017, p=0.027; p=0.023, p=0.031; p=0.029 and p=0.036, respectively). In FIG. 1D, the differences of MCA/DN-TNF vs MCA/TNFR1ko, MCA/PBS and MCA/TNFR2ko; MCA/TNFko vs MCA/TNFR1ko, MCA/PBS and MCA/TNFR2ko; and MCA/TNFR2ko vs MCA/PBS and MCA/TNFR1ko are significant (p<0.0001, p<0.0003, p<0.0001; p<0.0001, p<0.0001, p<0.0001; p=0.037, and p=0.029, respectively).

In FIGS. 2A, 2B, and 2C, the increases of cytokine levels in the sera of MCA/DN-TNF-treated mice were significant relative to that of Control and MCA/PBS-treated mice (p=0.026, p=0.05 and p=0.039, respectively). In FIG. 2D, the decreases of IL-1α levels in the sera of MCA/ENBREL®- and DN-TNF-treated mice versus Control and MCA/PBS-treated mice are significant (p=0.012 and p=0.023, respectively).

FIGS. 5A-5D. sTNF sequestration prevents MCA induction of cell-mediated suppression of NK-cell/DC crosstalk. As described in FIG. 3 legend, splenocytes of healthy/untreated (Control), and MCA-injected/PBS-treated (tumor-free: MCA/PBS; and tumor-bearing: MCA/PBS-T), TNFR2-Fc-treated (tumor-free: MCA/EN; and tumor-bearing: MCA/EN-T) and XPRO™ 1595-treated (tumor-free MCA/DN; and tumor-bearing MCA/DN-T) wild-type mice were obtained on days 14 (FIGS. 5A, 5C) and/or 84 (FIG. 5B, 5D) after MCA injection. These splenocytes, either alone (FIGS. 5A, 5B) or mixed with SCID splenocytes (SCID) at 1:1 and 3:1 ratios (FIGS. 5C, 5D), were stimulated with LPS (1 µg/mL) and IL-2 (6,000 IU/mL), for 24 h. After this stimulation, the cell culture-conditioned media were collected and examined for the presence of IFNβ using ELISA. In FIG. 5A and FIG. 5B, Control 1 and Control 2 designate unstimulated and IL-2/LPS-stimulated splenocytes of healthy/untreated mice, respectively. Data are means of triplicates±SD of IFNγ ng/mL. In FIG. 5A, MCA/PBS, MCA/EN and MCA/DN are significantly lower than Control 2 (p=0.00041, p=0.00057 and p=0.0016, respectively). In FIG. 5B, MCA/PBS and MCA/EN are significantly lower than Control 2 (p=0.0047, p=0.0016, respectively). In FIG. 5C, SCID:Control (1.0:0.0) and SCID:MCA/PBS (1.0:1.0-1.0:3.0) are significantly lower than SCID:Control (1.0:1.0-1.0:3.0) (p=0.026, p=0.001, respectively); and SCID:MCA/EN (1.0:1.0-1.0:3.0) and SCID:MCA/DN (1.0:1.0-1.0:3.0) are significantly higher than SCID:MCA/PBS (1.0:1.0-1.0:3.0) (p=0.019, and p=0.001, respectively). In FIG. 5D, SCID:Control (1.0:0.0) and SCID:MCA/PBS-T (1.0:1.0-1.0:3.0) are significantly lower than SCID: Control (1.0:1.0-1.0:3.0) (p=0.0034, p=0.0033, respectively); and SCID:MCA/EN (1.0:3.0), SCID:MCA/DN (1.0:1.0-1.0:3.0) and SCID:MCA/DN-T (1.0:1.0-1.0:3.0) are significantly higher than SCID:MCA/PBS-T (1.0:1.0-1.0:3.0) (p=0.027, p=0.028, p=0.046, respectively).

FIGS. 7A-7D. MCA does not affect and sTNF exclusion with XPRO™ 1595 decreases frequency of macrophages. Experimental groups were set up as described in FIG. 3 legend. Splenocytes were simultaneously stained with anti-CD45R-FITC and anti-F4/80-PE antibodies, and examined by flow cytometry. Single (FIG. 7A) non-granular (FIG. 7B) mononuclear cells were gated and (FIG. 7C) examined by two-color flow cytometry for the cell surface expression of CD45R and F4/80 markers of B cells and macrophages, respectively. $CD45^-F4/80^+$ macrophages are shown as dotplots (FIG. 7C) and histograms (FIG. 7D) of individual and mean (2-3 replicates) ±SD values of percentages of positive cells.

FIG. 9A), T helper cells (CD3$^+$NK1.1$^-$CD4$^+$: CD3$^+$CD4$^+$; FIG. 9B) and T-cytotoxic cells (CD3$^+$NK1.1$^-$CD8$^+$: CD3$^+$CD8$^+$; FIG. 9C).

FIG. 11. Comparison of the amino acid sequences of soluble TNF (SEQ ID NO: 1) and XPRO™ 1595 (SEQ ID NO: 2). The soluble TNF amino acid sequence (SEQ ID NO: 2) is the lower line, and is underlined. The differences between the two sequences are shown in bold and are highlighted.

SEQUENCE LISTING

Figure 1A:
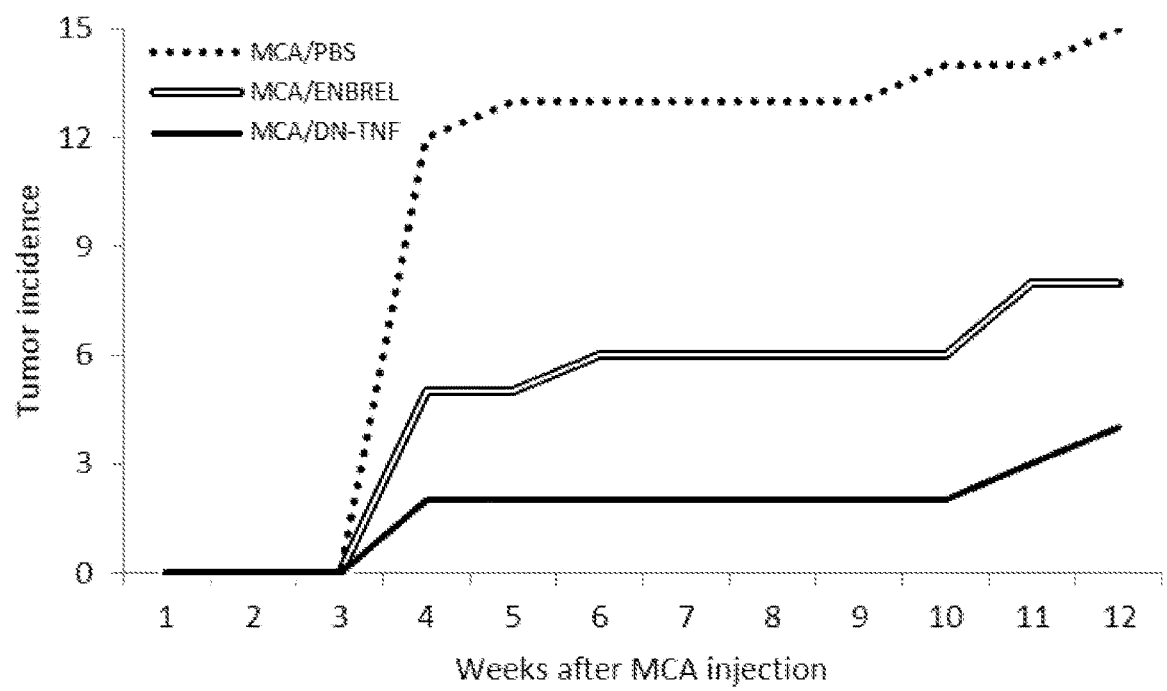
FIGS. 1A-1D. Sequestration of sTNF with XPRO™ 1595 or deletion of TNF or TNFR1 genes protect mice from MCA-induced carcinogenesis.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file [Sequence_Listing, 4,096 bytes], which is incorporated by reference herein. In the accompanying sequence listing:

SEQ ID NO: 1 is the amino acid sequence of human TNF-α.

SEQ ID NO: 2 is the amino acid sequence of an exemplary DN-TNF-α (XPRO™ 1595).

SEQ ID NO: 3 is a nucleic acid sequence encoding an exemplary DN-TNF-α (XPRO™ 1595).

DETAILED DESCRIPTION

It is disclosed herein that soluble tumor necrosis factor (sTNF) has a pivotal role in the expansion of MDSCs, development of immunosuppression and promotion of carcinogenesis and tumor growth, such as, but not limited to, in chemical-induced carcinogenesis. The administration of DN-TNF-α efficiently inhibits tumor immunosuppression and tumor development.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects. Therefore, the general term "subject" is understood to include all animals, including, but not limited to, humans, or veterinary subjects, such as other primates, rodents, dogs, cats, horses, and cows.

Antibody: A polypeptide ligand comprising at least a light chain or heavy chain immunoglobulin variable region which specifically recognizes and binds an epitope (e.g., an antigen, such as a tumor or viral antigen or a fragment thereof, or another protein of interest, such as PD-1 or CTLA-4). This includes intact immunoglobulins and the variants and portions of them well known in the art, such as Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (e.g., humanized murine antibodies), heteroconjugate antibodies (e.g., bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Typically, an immunoglobulin has a heavy and light chain Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs has been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (e.g., see U.S. Pat. No. 5,585, 089).

A "neutralizing antibody" is an antibody that interferes with any of the biological activities of a polypeptide, such as a PD-1 polypeptide. For example, a neutralizing antibody can interfere with the ability of a PD-1 polypeptide to reduce an immune response such as the cytotoxicity of T cells. In several examples, the neutralizing antibody can reduce the ability of a PD-1 polypeptide to reduce an immune response by about 50%, about 70%, about 90% or more. Any standard assay to measure immune responses, including those described herein, may be used to assess potentially neutralizing antibodies.

BRAF kinase: An enzyme involved in the MAPK signaling pathway. In normal cells, cell surface receptor tyrosine kinases dimerize when a growth factor binds to their extracellular region. This initiates the MAPK signaling cascade, which promotes cell proliferation, survival, invasion, and angiogenesis (Cheng, Y., et al. 2013. *Cancer Metastasis Rev* 32: 567-584). Somatic mutations in BRAF lead to reprogramming of pre-malignant melanocytes. Mutated BRAF signals independently of upstream cues, leading to overactive downstream signaling via MAPK kinase (MEK) and extracellular signal-regulated kinase (ERK). Such dysregulated signaling causes uncontrolled cell proliferation and extended cell survival. Approximately 50% of melanomas harbor BRAF mutations at position V600 of the protein chain, the majority of which (>90%) involve the substitution of glutamic acid (E) for valine (V; V600E), resulting in constitutively active BRAF that is independent of upstream cues (Cantwell-Dorris, E. R., et al. 2011. *Molecular Cancer Therapeutics* 10: 385-394).

Breast cancer: A neoplastic condition of breast tissue that can be benign or malignant. The most common type of breast cancer is ductal carcinoma. Ductal carcinoma in situ is a non-invasive neoplastic condition of the ducts. Lobular carcinoma is not an invasive disease but is an indicator that a carcinoma may develop. Infiltrating (malignant) carcinoma of the breast can be divided into stages (I, IIA, IIB, IIIA, IIIB, and IV).

Breast carcinomas lose the typical histology and architecture of normal breast glands. Generally, carcinoma cells overgrow the normal cells and lose their ability to differentiate into glandular like structures. The degree of loss of differentiation in general is related to the aggressiveness of the tumor. For example, "in situ" carcinoma by definition retains the basement membrane intact, whereas as it progresses to "invasive", the tumor shows breakout of basement membranes. Thus one would not expect to see, within breast carcinomas, staining of a discrete layer of basal cells as seen in normal breast tissue. For a discussion of the physiology and histology of normal breast and breast carcinoma, see Ronnov-Jessen, L., Petersen, O. W. & Bissell, M. J., "Cellular changes involved in conversion of normal to malignant breast: importance of the stromal reaction" (see, for example, *Physiol, Rev* 76, 69-125, 1996).

Breast cancers can be divided into groups based on their gene expression profiles. Basal-type carcinomas usually are negative for expression of estrogen receptor (ER) and negative for expression of HER2 (erbB2) and progesterone receptor (PR), and thus are referred to as "triple-negative breast cancers" or "TNBC." This type of breast cancer is also denoted $ER^-/HER2^-/PR^-$ and represents about 15-20% of all breast cancer, and generally cannot be treated using Her2 targeted or estrogen targeted therapies. It is believed that the aggressive nature of this cancer is correlated with an enrichment for cancer stem cells (CSC) with a $CD44^+$ $CD24^{-/lo}$ phenotype. In some embodiments, basal carcinomas are negative for expression of progesterone receptor (PR), positive for expression of epidermal growth factor receptor (EGFR), and positive for expression of cytokeratin 5 (CK5). This phenotype is denoted as follows: $ER^-/PR^-/HER2^-/CK5^+/EGFR^+$.

Cancer: A malignant tumor that has undergone characteristic anaplasia with loss of differentiation, increase rate of growth, invasion of surrounding tissue, and is capable of metastasis. For example, prostate cancer is a malignant neoplasm that arises in or from prostate tissue, and breast cancer is a malignant neoplasm that arises in or from breast tissue (such as a ductal carcinoma). Residual cancer is cancer that remains in a subject after any form of treatment given to the subject to reduce or eradicate the cancer. Metastatic cancer is a cancer at one or more sites in the body other than the site of origin of the original (primary) cancer from which the metastatic cancer is derived. Cancer includes, but is not limited to, solid tumors.

Chemotherapeutic agent: An agent with therapeutic usefulness in the treatment of diseases characterized by abnormal cell growth (e.g., an anti-neoplastic agent). In one embodiment, a chemotherapeutic agent is an agent of use in treating neoplasms such as solid tumors. Chemotherapeutic agents can be protein or non-protein agents, such as small molecule drugs, antibodies, peptides, proteins, and immunomodulators. In one embodiment, a chemotherapeutic agent is a radioactive molecule. One of skill in the art can readily identify a chemotherapeutic agent (for instance, see Slapak and Kufe, *Principles of Cancer Therapy*, Chapter 86 in *Harrison's Principles of Internal Medicine*, 14th edition; Perry et al., *Chemotherapy*, Ch. 17 in Abeloff, *Clinical Oncology* $2^{nd}$ ed., © 2000 Churchill Livingstone, Inc; Baltzer L., Berkery R. (eds): *Oncology Pocket Guide to Chemotherapy,* 2nd ed. St. Louis, Mosby-Year Book, 1995; Fischer D S, Knobf M F, Durivage H J (eds): *The Cancer Chemotherapy Handbook,* 4th ed. St. Louis, Mosby-Year Book, 1993).

Colon cancer: Colorectal cancer, also called large bowel cancer, includes cancerous growths in the colon, rectum and appendix. With 655,000 deaths worldwide per year, it is the third most common form of cancer and the second leading cause of cancer-related death in the Western world. Many colorectal cancers are thought to arise from adenomatous polyps in the colon. These mushroom-like growths are usually benign, but some may develop into cancer over time. The majority of the time, the diagnosis of localized colon cancer is through colonoscopy. Therapy is usually through surgery, which in many cases is followed by chemotherapy. The first symptoms of colon cancer are usually vague, such as bleeding, weight loss, and fatigue (tiredness). Local (bowel) symptoms are rare until the tumor has grown to a large size. Generally, the nearer the tumor is to the anus, the more bowel symptoms are present.

Contacting: Placement in direct physical association, including both a solid and liquid form. Contacting can occur in vitro with isolated cells or in vivo by administering to a subject.

Cytokine: The term "cytokine" is used as a generic name for a diverse group of soluble proteins and peptides that act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to, tumor necrosis factor α (TNFα), interleukin (IL)-1, IL-12, and IL-17.

Decrease or Inhibit: Becoming less or smaller, as in number, amount, size, or intensity. In one example, decreasing or inhibiting the risk of a disease (such as for tumor formation) includes a decrease in the likelihood of developing the tumor by at least about 20%, for example by at least about 30%, 40%, 50%, 60%, 70%, 80%, or 90%. In another example, decreasing or inhibiting the risk of a disease includes a delay in the development of the disease, for example a delay of at least about six months, such as about one year, such as about two years, about five years, or about ten years.

In one example, decreasing or inhibiting the signs and symptoms of a tumor includes decreasing the size, volume, or number of tumors (such as colon or breast tumors) or metastases by a desired amount, for example by at least 5%, at least 10%, at least 15%, at least 20%, at least 25%, at least 30%, at least 50%, at least 75%, or even at least 90%, as compared to a response in the absence of the therapeutic composition.

Dendritic cell vaccine: Bone marrow-derived dendritic cells (DCs) are professional antigen presenting cells (APCs) that mediate the cross-priming of effector T cells reactive against specific proteins and glycolipids. In the cancer setting, DC cross-priming promotes enhanced protective or therapeutic immunity. DCs first capture and digest dead cancer cells or proteins. Then they process the proteins into peptide epitopes, and finally present these epitopes in the context of the cell surface expressed MHC molecules to T cell receptors (TCRs) on specific CD4+ and CD8+ T cells. The consequent generation of antitumor effector T cells is invigorated and regulated by costimulatory molecule and cytokine signals contributed by DCs. Dendritic cells can be generated in vitro by stimulating peripheral blood monocytes with GM-CSF and IL-4. They can be also matured with Toll-like receptor ligands (TLR-Ls) and cytokines to increase their antigen-presenting activity. These DCs can be loaded with a cancer cell lysate, a cancer recombinant protein, a synthetic peptide or a nucleic acid (DNA or RNA), and injected into cancer patients as a vaccine to promote anti-cancer immune response and control of tumor growth.

Immune response: A response of a cell of the immune system, such as a B cell or T cell to a stimulus. In one embodiment, the response is an inflammatory response.

Interleukin-12 (IL-12): An interleukin that is naturally produced by dendritic cells, macrophages, and human B-lymphoblastoid cells in response to antigenic stimulation. IL-12 is involved in the differentiation of naive T cells into Th1 cells. It stimulates the production of interferon-gamma (IFN-γ) and tumor necrosis factor-alpha (TNF-α) from T cells and natural killer (NK) cells, and reduces IL-4 mediated suppression of IFN-γ. IL-12 is composed of a bundle of four alphahelices. It is a heterodimeric cytokine encoded by two separate genes, IL-12A (p35)) and IL-12B (p40). The active heterodimer (referred to as 'p70'), and a homodimer of p40 are formed following protein synthesis. An exemplary human IL-12A amino acid sequence is shown in UNIPROT® Accession No. P29246, Dec. 23, 2014.

Interleukin-17 (IL-17): A cytokine that acts as a potent mediator in delayed-type hypersensitivity reactions by increasing chemokine production in various tissues to recruit monocytes and neutrophils to the site of inflammation. IL-17 is produced by T-helper cells and is induced by IL-23 which results in destructive tissue damage in delayed-type reactions. IL-17 binds to a type I cell surface receptor called IL-17R, of which there are at least three variants IL17RA, IL17RB, and IL17RC. An exemplary human IL-17 amino acid sequence is shown in UNIPROT® Accession No. Q15552, as available on Dec. 23, 2014.

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

Lung cancer: The main type of lung cancer is carcinoma of the lung, which includes small cell lung carcinoma and non-small cell lung carcinoma. Non-small cell lung carcinoma (NSCLC) is sometimes treated with surgery, while small cell lung carcinoma (SCLC) usually responds to chemotherapy and radiation. The most common cause of lung cancer is long-term exposure to tobacco smoke.

The non-small cell lung carcinomas are grouped together because their prognosis and management are similar. There are three main sub-types: squamous cell lung carcinoma, adenocarcinoma, and large cell lung carcinoma. Squamous cell lung carcinoma usually starts near a central bronchus. Cavitation and necrosis within the center of the cancer is a common finding. Well-differentiated squamous cell lung cancers often grow more slowly than other cancer types. Adenocarcinoma accounts for 29.4% of lung cancers. It usually originates in peripheral lung tissue. Most cases of adenocarcinoma are associated with smoking; however, among people who have never smoked, adenocarcinoma is the most common form of lung cancer. A subtype of adenocarcinoma, the bronchioloalveolar carcinoma, is more common in females.

Small cell lung cancers (SCLC, also called "oat cell carcinoma") is less common. It tends to arise in the larger airways (primary and secondary bronchi) and grows rapidly, becoming quite large. The "oat" cell contains dense neurosecretory granules (vesicles containing neuroendocrine hormones), which give this an endocrine/paraneoplastic syndrome association. While initially more sensitive to chemotherapy, it ultimately carries a worse prognosis and is often metastatic at presentation. Small cell lung cancers are divided into limited stage and extensive stage disease. This type of lung cancer also is strongly associated with smoking.

Malignant cells: Cells which have the properties of anaplasia, invasion and metastasis.

Myeloid Derived Suppressor Cells (MDSCs): A population of immune cells from the myeloid lineage that possess strong immunosuppressive activities, such as the ability to inhibit T cell proliferation and activation. In humans, MDSC express high levels of CD33, CD11b and low levels of HLA-DR. In chronic inflammatory conditions (such as viral and bacterial infections) or cancer, myeloid differentiation is skewed towards the expansion of MDSCs. The MDSCs increase in bone marrow, peripheral blood and secondary lymphoid organs such as spleen and lymph nodes, infiltrate inflammation sites and tumors, where they inhibit T cells and NK cells.

Natural Killer (NK) cell/Dendritic cell (DC) cross-talk: NK cells and DCs are effector cells of the innate immune system that rapidly recognize and eliminate microbial pathogens and abnormal cells, and induce and regulate innate and adaptive immune functions. NK cells and DCs are able to co-localize in and interact in inflamed and peripheral lymphoid tissues. This cross-talk usually occurs in cell-to-cell contact, and is mediated via membrane bound and secreted cytokines, including transmembrane TNF (tmTNF) trans-presented interleukin (IL)-15, IL-12, IL-2, IL-18 and interferon (IFN)γ. The interaction leads to reciprocal stimulation and regulation of the interacting cells, and results in NK cell activation and DC maturation. NK cells induce in DCs increases in expression of maturation markers and secretion of IL-12. Reciprocally, DCs induce in NK cells the expression of activation marker CD69, proliferation and augmentation of cytotoxicity and IFN-γ secretion. The joint increases in NK cell and DC functions empower the innate immune system with enhanced abilities to directly eliminate viral infected and transformed cells and induce robust Th1 adaptive immune responses, which enable efficient control of viral infections and cancers.

Normal cells: Non-diseased (wild-type) cells, such as non-tumor, non-malignant cells.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, such as a "recombinant polypeptide." A recombinant nucleic acid may serve a non-coding function (such as a promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, for example, by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see for example, *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, such as version 7.0 (Devereaux et al., *Nuc. Acids Res.* 12:387-395, 1984).

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov/). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989).

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

OX40: The OX-40 receptor ("OX-40") (Paterson et al. (1987) *Mol. Immunol.* 24:1281-1290; Calderhead et al. (1993) *J. Immunol.* 151:5261-5271) has been shown to be present only on antigen activated $CD4^+$ T-cells in vivo (Weinberg et al. (1994) *J. Immunol.* 152:4712-4721; Wienberg et al. (1996) *Nature Medicine* 2:183-189) unlike the CD28 receptor, which is present on the surface of many sub-classes of T-cells (irrespective of whether they are activated or not). For example, OX-40 is present on activated $CD4^+$ T-cells that recognize autoantigen at the site of inflammation in autoimmune disease, but not in the periphery. OX-40 has also been shown to be present on the surface of a percentage of $CD4^+$ T-cells isolated from tumor infiltrating lymphocytes and draining lymph node cells removed from patients with squamous cell tumors of the head and neck and melanomas (Vetto et al. (1997) *Am. J. Surg.* 174:258-265). The OX-40 ligand, a member of the tumor necrosis factor (TNF) superfamily, has been shown to co-stimulate T-cells which have been activated with an anti-CD3 antibody (i.e., in a nonantigen-specific manner) (Godfrey et al. (1994) *J. Exp. Med.* 180:757-762). Despite the recognition of the costimulatory properties of the OX-40 ligand, its benefits have not previously been fully exploited to enhance an antigen specific immune response.

Parenteral: Administered outside of the intestine, e.g., not via the alimentary tract. Generally, parenteral formulations are those that will be administered through any possible mode except ingestion. This term especially refers to injections, whether administered intravenously, intrathecally, intramuscularly, intraperitoneally, intraarticularly, or subcutaneously, and various surface applications including intranasal, intradermal, and topical application, for instance.

Pharmaceutical agent or drug: A chemical compound or composition capable of inducing a desired therapeutic or prophylactic effect when properly administered to a subject.

Pharmaceutical agents include, but are not limited to, anti-infective agents, anti-inflammatory agents, bronchodilators, enzymes, expectorants, leukotriene antagonists, leukotriene formation inhibitors, and mast cell stabilizers.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the DN-TNF-α proteins and nucleic acids disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the development of a disease, such as a tumor, including preventing the conversion of a benign tumor to malignant cancer. In some embodiments, a prevention inhibits the full development of a tumor, for example in a person who is known to have a predisposition to a disease such as a cancer. An example of a person with a known predisposition is someone with a history of breast cancer in the family, or who has been exposed to factors that predispose the subject to a condition, such as colon cancer, breast cancer, lung cancer or skin cancer. Prevention can include increasing the immune response to the tumor, such as by increasing the humoral response, or cytokines, NK cells, activated CTLs, such as CD9+ T cells, or decreasing the number and/or function of myeloid derived suppressor cells (MDSCs). Prevention can include decreasing an immunosuppressive immune response, such as regulatory T cells (Tregs), or by blocking (PD)-1 molecule. "Treating" refers to a therapeutic intervention that ameliorates a sign or symptom of a disease or pathological condition after it has begun to develop. For example, "treating" a tumor can include reducing tumor volume, reducing the number of tumors or inhibiting metastasis of the tumor. "Ameliorating" refers to the reduction in the number or severity of signs or symptoms of a disease, such as cancer.

In one embodiment of the disclosure, the formation of tumors, such as metastasis, is delayed, prevented or decreased. In another aspect, the number of tumors is decreased. Thus, signs and symptoms of a disease can be decreased.

Programmed Death (PD)-1: PD-1 molecules are members of the immunoglobulin gene superfamily. The human PD-1 has an extracellular region containing an immunoglobulin superfamily domain, a transmembrane domain, and an intracellular region including an immunoreceptor tyrosine-based inhibitory motif (ITIM) ((Ishida et al., EMBO J. 11:3887, 1992; Shinohara et al., Genomics 23:704, 1994; U.S. Pat. No. 5,698,520). These features also define a larger family of molecules, called the immunoinhibitory receptors, which also includes gp49B, PIR-B, and the killer inhibitory receptors (KIRs) (Vivier and Daeron (1997) Immunol. Today 18:286). Without being bound by theory, it is believed that the tyrosyl phosphorylated ITIM motif of these receptors interacts with the S112-domain containing phosphatase, which leads to inhibitory signals. A subset of these immunoinhibitory receptors bind to major histocompatibility complex (MHC) molecules, such as the KIRs, and cytotoxic T-lymphocyte associated protein 4 (CTLA4) binds to B7-1 and B7-2. In humans, PD-1 is a 50-55 kDa type I transmembrane receptor that was originally identified in a T cell line undergoing activation-induced apoptosis. PD-1 is expressed on T cells, B cells, and macrophages. The ligands for PD-1 are the B7 family members PD-ligand 1 (PD-L1, also known as B7-H1) and PD-L2 (also known as B7-DC).

In vivo, PD-1 is expressed on activated T cells, B cells, and monocytes. Experimental data implicates the interactions of PD-1 with its ligands in down regulation of central and peripheral immune responses. In particular, proliferation in wild-type T cells but not in PD-1-deficient T cells is inhibited in the presence of PD-L1. Additionally, PD-1-deficient mice exhibit an autoimmune phenotype. An exemplary amino acid sequence of human PD-1 is set forth in Ishida et al., EMBO J. 11:3887, 1992; Shinohara et al. Genomics 23:704, 1994; U.S. Pat. No. 5,698,520):

Engagement of PD-1 (for example by crosslinking or by aggregation), leads to the transmission of an inhibitory signal in an immune cell, resulting in a reduction of immune responses concomitant with an increase in immune cell anergy. PD-1 binds two ligands, PD-L1 and PD-L2, both of which are human PD-1 ligand polypeptides, that are members of the B7 family of polypeptides.

PD-1 antagonists include agents that reduce the expression or activity of a PD ligand 1 (PD-L1) or a PD ligand 2 (PD-L2) or reduces the interactions between PD-1 and PD-L1 or PD-L2. Exemplary compounds include antibodies (such as an anti-PD-1 antibody, an anti-PD-L1 antibody, and an anti-PD-L2 antibody), RNAi molecules (such as anti-PD-1 RNAi molecules, anti-PD-L1 RNAi, and an anti-PD-L2 RNAi), antisense molecules (such as an anti-PD-1 antisense RNA, an anti-PD-L1 antisense RNA, and an anti-PD-L2 antisense RNA), dominant negative proteins (such as a dominant negative PD-1 protein, a dominant negative PD-L1 protein, and a dominant negative PD-L2 protein), see, for example, PCT Publication No. 2008/083174, incorporated herein by reference.

Promoter: A promoter is an array of nucleic acid control sequences that directs transcription of a nucleic acid. A promoter includes necessary nucleic acid sequences near the start site of transcription, such as in the case of a polymerase II type promoter (a TATA element). A promoter also optionally includes distal enhancer or repressor elements which can be located as much as several thousand base pairs from the start site of transcription. Both constitutive and inducible promoters are included (see e.g., Bitter et al., *Methods in Enzymology* 153:516-544, 1987).

Specific, non-limiting examples of promoters include promoters derived from the genome of mammalian cells (e.g., metallothionein promoter) or from mammalian viruses (e.g., the retrovirus long terminal repeat; the adenovirus late promoter; the vaccinia virus 7.5K promoter). Promoters produced by recombinant DNA or synthetic techniques can also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Hepatocellular carcinoma (HCC): A malignant tumor of liver that is the third most common cause of cancer related deaths worldwide, and is the fastest growing cause of cancer-related death of US males. Hepatitis viruses, alcoholic cirrhosis, primary biliary cirrhosis, non-alcoholic fatty liver disease and autoimmune hepatitis have all been linked to HCC oncogenesis. The primary risk factors for developing HCC are cirrhosis (independent of its etiology, with annual HCC incidence rate in cirrhotic patients 2-6%) and chronic infection with hepatitis B or C virus.

As HCC is commonly diagnosed in late stages of the disease, less than 20% of patients are eligible for possibly curable surgery (resection and liver transplantation). Local regional therapy is largely palliative and includes cryoablation, radiofrequency ablation, and transarterial embolization. Sorafenib (a multi-targeted kinase inhibitor), which improves survival by 2.3-2.8 months is the standard of care for patients with advanced HCC.

Prostate Cancer: A malignant tumor, generally of glandular origin, of the prostate. Prostate cancers include adenocarcinomas and small cell carcinomas. Many prostate cancers, specifically adenocarcinomas, express prostate specific antigen (PSA). Factors that increase the risk of prostate cancer include: older age, a family history of the disease, and race. About 99% of cases occur in those over the age of 50. If a first degree relative has the disease, then risk is increased by 2 to 3 fold. Symptoms include frequent urination, nocturia, difficulty starting and maintaining a steady stream of urine, hematuria, and dysuria.

Skin Cancer: Skin cancer is a malignant growth on the skin which can have many causes. Skin cancer generally develops in the epidermis (the outermost layer of skin), so a tumor is usually clearly visible. This makes most non-melanoma skin cancers detectable in the early stages. Skin cancer represents the most commonly diagnosed malignancy, surpassing lung, breast, colorectal and prostate cancer.

The most common type of skin cancer is non-melanoma skin cancer. Non-melanoma skin cancers include all skin cancers except malignant melanoma (cancer that develops from melanocytes, the pigment-producing cells of the skin). There are many types of non-melanoma skin cancers. Two common types of non-melanoma skin cancer are basal cell carcinoma and squamous cell carcinoma. These two types of skin cancer are also known as keratinocyte carcinomas.

Basal cell carcinoma begins in the lowest layer of the epidermis, called the basal cell layer. About 70% to 80% of all skin cancers in men and 80% to 90% in women are basal cell carcinomas. They usually develop on sun-exposed areas, especially the head and neck. Basal cell carcinoma is slow growing. It is highly unusual for a basal cell cancer to spread to lymph nodes or to distant parts of the body. However, if a basal cell cancer is left untreated, it can grow into nearby areas and invade the bone or other tissues beneath the skin. After treatment, basal cell carcinoma can recur in the same place on the skin. Also, new basal cell cancers can start elsewhere on the skin. Within 5 years of being diagnosed with one basal cell cancer, 35% to 50% of people develop a new skin cancer.

Squamous cell carcinomas account for about 10% to 30% of all skin cancers. They commonly appear on sun-exposed areas of the body such as the face, ear, neck, lip, and back of the hands. Squamous cell carcinomas can also develop in scars or skin ulcers elsewhere. These carcinomas are generally more aggressive than basal cell cancers. Squamous cell carcinomas can sometimes start in actinic keratoses. Squamous cell carcinoma in situ (also called Bowen disease) is the earliest form of squamous cell skin cancer and involves cells that are within the epidermis and have not invaded the dermis.

Less common types of nonmelanoma skin cancer include Kaposi sarcoma, cutaneous lymphoma, skin adnexal tumors and various types of sarcomas and Merkel cell carcinoma. Together, these types of nonmelanoma skin cancer account for less than 1% of nonmelanoma skin cancers.

The most lethal type of skin cancer is melanoma. Melanoma (also known as malignant melanoma or cutaneous melanoma) is a cancer that begins in the melanocytes. Because most melanoma cells still produce melanin, melanoma tumors are usually brown or black. This form of skin cancer can be fatal if not treated early.

Subject at risk: An individual, such as a human or a veterinary subject, that is prone to developing a certain condition, such as a tumor. This can be due to their age, genotype, or due to an environmental exposure. Examples are a human subject who is exposed to a carcinogen due to an occupational exposure (i.e., asbestos, silica, ionizing radiation, aromatic amines, heavy metals, pesticides, petrochemicals and combustion byproducts), or a human subject exposed to cigarette smoke, either because that individual smokes or due to exposure to second-hand smoke, or a subject exposed to ultraviolet light, such as due to tanning, or a subject genetically pre-disposed to developing a tumor.

Th1 immune response: Based on their array of cytokines, antigen-specific effector CD4+ T helper (Th) cells can be categorized into Th1, Th2, Tregs, and Th17 cells. Th1 cells secrete the Th1 type cytokines IFNγ, IL-2 and LTα, and mediate adaptive T helper-1 (Th1) immune response that contributes to immune defense against intracellular pathogens, viruses and cancer. Effector CD4+ Th1 cells are generated by stimulation of Th-precursors (Th0) cells by viral or cancer antigens presented in the context of major histocompatibility class II complex (MHC II) and IL-12 secreted by antigen presenting cells such as DCs, and IFNγ secreted by NK cells. Th1 effector cells suppress Th2 immune response and help generation of CD8+ cytotoxic T lymphocytes (CTLs) and delayed type hypersensitivity (DTH) and IgG2a, which have a critical role in killing and eliminating virally infected and cancer cells.

Th2 cells: Antigen-specific effector Th2 cells secrete the Th2 type cytokines IL-4, IL-5 and IL-6 that promote proliferation and differentiation of B cells, leading to secretion of antibodies, which are characteristic for a humoral immune response. Th2 immune response contributes to allergic reactions.

Th17 immune response: T helper 17 (Th17) immune response has physiological role to provide help in development of anti-microbial immunity at epithelial/mucosal barriers. It is also responsible for inflammation and tissue injury in autoimmune diseases such as multiple sclerosis, juvenile diabetes, rheumatoid arthritis and Crohn's disease. In addition, Th17 immune response may play a role in allergen-induced airway responses. TGFb, IL-6, IL-21 and IL-23 stimulate generation of Th17 effector cells from Th0 cells. Th17 effector cells secrete IL-17, IL-21 and IL-22, which mediate Th17 immune response.

Therapeutic agent: Used in a generic sense, it includes treating agents, prophylactic agents, and replacement agents. A therapeutic agent can be surgery, radiation and chemotherapy. Antibodies, chemical compounds, cells and cytokines can be therapeutic agents Therapeutically effective amount: A quantity of a specified compound or DN-TNF-α protein (or nucleic acid encoding the protein) sufficient to achieve a desired effect in a subject being treated. For instance, this can be the amount of a DN-TNF-α protein (or nucleic acid encoding the protein) necessary to reduce immunosuppression and increase an immune response to a tumor, prevent a tumor, delay the development of a tumor, and/or reduce the risk of developing a tumor. In one embodiment, a therapeutically effective amount of a DN-TNF-α protein (or nucleic acid encoding the protein) is the amount that alone, or together with one or more additional therapeutic agents (such antineoplastic agents or immunosuppressive agents), induces the desired response, such as prevention, delaying development, or reducing tumor number. The preparations disclosed herein are administered in therapeutically effective amounts.

In one example, a desired response is to prevent the development of a tumor. In another example, a desired response is to delay the development, progression, or metastasis of a tumor, for example, by at least about 3 months, at least about six months, at least about one year, at least about two years, at least about five years, or at least about ten years. In a further example, a desired response is to decrease the occurrence of cancer, such as prostate, colon cancer, breast cancer or lung cancer. For example, the composition including DN-TNF-α protein (or nucleic acid encoding the protein) can, in some examples, decrease the size, volume, or number of tumors (such as colorectal tumors) by a desired amount, for example by at least 5%, at least 10%, at least 15%, at least 20%, at least 25%, at least 30%, at least 50%, at least 75%, or even at least 90%, as compared to a response in the absence of the therapeutic composition.

The effective amount of a DN-TNF-α protein (or nucleic acid encoding the protein) that is administered to a human or veterinary subject will vary depending upon a number of factors associated with that subject, for example the overall health of the subject. An effective amount of an agent can be determined by varying the dosage of the product and measuring the resulting therapeutic response, such as the number of tumors. Effective amounts also can be determined through various in vitro, in vivo or in situ immunoassays. The disclosed agents can be administered in a single dose, or in several doses, as needed to obtain the desired response. However, the effective amount can be dependent on the source applied, the subject being treated, the severity and type of the condition being treated, and the manner of administration.

A therapeutically effective amount of DN-TNF-α protein (or nucleic acid encoding the protein) can be administered systemically or locally. In addition, an effective amount of DN-TNF-α protein (or nucleic acid encoding the protein) can be administered in a single dose, or in several doses, for example daily, twice a week and once a week during a course of treatment. However, the effective amount of the DN-TNF-α protein (or nucleic acid encoding the protein) will be dependent on the preparation applied, the subject being treated, the severity and type of the affliction, and the manner of administration of the compound.

Toll-Like Receptor Ligand: Toll-Like Receptor Ligands (TLR-Ls) are structurally conserved molecules that are derived from microorganisms (Pathogen-Associated Molecular Patterns (PAMPs)) or damaged cells (Damage Associated Molecular Patterns (PAMPs)) and have the ability to strongly activate dendritic cells via their TLRs. Thus activated DCs undergo maturation, enhance secretion of immunoregulatory cytokines, increase antigen presentation, and promote innate and adaptive immune responses. Because of this property, TLR-Ls are used as immune adjuvants with vaccines to modulate the quality, and enhance the magnitude and overall effectiveness of vaccine-induced immune responses. Several of TLR-Ls, including TLR3-L Poly (I:C) (Polyinocine-Polycytidylic acid, a synthetic analog of double-strand RNA) and TLR9-L unmethylated CpG (a synthetic oligonucleotide), are used as immune adjuvants with anti-cancer vaccines.

Treatment: Refers to a therapeutic intervention that ameliorates a sign or symptom of a disease or pathological condition related to a disease (such as a tumor) that is already present in the subject. Treatment can also induce remission or cure of such condition. In particular examples, treatment includes inhibiting a tumor, for example by inhibiting the full development of a tumor, such as preventing development of a metastasis or the development of a primary tumor, reducing tumor volume, or reducing the total number of tumors. Inhibition may not require a total absence of a tumor. In other examples, treatment includes inhibiting, reducing the risk of, or delaying development of, skin cancer. Reducing or suppressing a sign or symptom associated with a disease (such as a tumor, for example, skin cancer, lung cancer, colon cancer, or breast cancer) can be evidenced, for example, by a delayed onset of clinical symptoms of the disease in a susceptible subject (such as a subject having a tumor which has not yet metastasized), a reduction in severity of some or all clinical symptoms of the disease, a slower progression of the disease (for example by prolonging the life of a subject having the disease), a reduction in the number of relapses of the disease, an improvement in the overall health or well-being of the subject, or by other parameters well known in the art that are specific to the particular disease.

Tregs: Regulatory T cells (Tregs) or suppressor T cells are a subpopulation of T cells which modulate the immune system, maintain tolerance to self-antigens, and prevent excessive immune reactions and autoimmune diseases. Tregs generally suppress or down-regulate induction and proliferation of effector Th1 and Th2 cells. Tregs have a characteristic phenotype expressing CD4, CD25, and Foxp3 (CD4$^+$CD25$^{high}$Foxp3+) and secreting the immunosuppressive cytokines TGFβ and IL-10. Tregs expand in subjects with cancer and contribute in the immunosuppression that helps cancer to escape an anticancer immune mechanisms.

Tumor: An abnormal growth of cells, which can be benign or malignant. Cancer is a malignant tumor, which is characterized by abnormal or uncontrolled cell growth. Other features often associated with malignancy include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, salivary gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma).

An "established" or "existing" tumor is an existing tumor that can be discerned by diagnostic tests. In some embodiments, an established tumor can be palpated. In some embodiments, an "established tumor" is at least 500 mm$^3$, such as at least 600 mm$^3$, at least 700 mm$^3$, or at least 800 mm$^3$ in size. In other embodiments, the tumor is at least 1 cm long. With regard to a solid tumor, and established tumor generally has a robust blood supply, and has induced Tregs and myeloid derived suppressor cells (MDSCs).

In several examples, a tumor is breast cancer, prostate cancer, colon cancer, liver cancer or a lung cancer. In another example, a tumor is a skin tumor.

Tumor Necrosis Factor (TNF)-α: A cytokine that exerts its effect through distinct membrane TNF-α receptors. Wild-type TNF is primarily produced as a 212-amino acid type II transmembrane protein that is arranged in stable homotrimers. A soluble homotrimeric cytokine (sTNF) is released via proteolytic cleavage from the transmembrane form by the metalloprotease TNF alpha converting enzyme (TACE, also called ADAM17). Both the secreted and the membrane bound forms are biologically active, although they are believed to have different activities.

Crystallographic studies of TNF and the structurally related cytokine, lymphotoxin (LT) have shown that both cytokines exist as homotrimers, with subunits packed edge to edge in a threefold symmetry.

TNF can bind two receptors, tumor necrosis factor receptor type 1 (TNFR1, also called CD120a and p55/60) and tumor necrosis factor receptor type 2 (TNFR2, also called CD120b; p75/80). TNFR1 is a 55-kDa protein and TNFR2 is a 75-kDa protein. TNFR1 is expressed in most tissues, and can be fully activated by both the membrane-bound and soluble trimeric forms of TNF, whereas TNFR2 is found mostly in cells of the immune system, and respond to the membrane-bound form of the TNF homotrimer. TNF is mainly produced by activated macrophages. The binding of TNF-α to its receptors mediates a number of diverse vital functions, including structural and functional organization of secondary lymphoid organs, apoptosis and antitumor activity, inhibition of viral replication, immunoregulation and inflammation. TNF also plays important roles in pathogenesis of autoimmune diseases, acute phase reaction, septic shock, fever and cachexia. These diverse functions are induced via cognate interactions between the two TNF forms and two transmembrane receptors.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker gene and other genetic elements known in the art. Vectors include plasmid vectors, including plasmids for expression in gram negative and gram positive bacterial cell. Exemplary vectors include those for expression in *E. coli* and *Salmonella*. Vectors also include poxviral vectors, such as, but are not limited to, retrovirus, orthopox, avipox, fowlpox, capripox, suipox, adenoviral, herpes virus, alpha virus, baculovirus, Sindbis virus, vaccinia virus and poliovirus vectors. Vectors also include vectors for expression in yeast cells.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Dominant Negative Tumor Necrosis Factor Proteins and Nucleic Acids

A DN-TNF-α protein has modulated activity as compared to wild type TNF-α. In some embodiments, the DN-TNF-α proteins have decreased to absent biological activity (e.g. antagonism) as compared to wild type TNF-α, including but not limited to, decreased binding to a receptor (p55, p75 or both), decreased activation and/or ultimately a loss of cytotoxic activity as compared to a wild-type TNF-α. A "cytotoxic activity" refers to the ability of a DN-TNF-α polypeptide to selectively kill or inhibit cells. DN-TNF exhibit less than 50% biological activity, less than 25%, less than 15%, or less than 10% of a biological activity of wild-type TNF-α. Suitable assays for TNF-α activity include, but are not limited to, caspase assays, TNF-α cytotoxicity assays, DNA binding assays; transcription assays; size exclusion chromatography assays and radiolabeling/immuno-precipitation; and stability assays (including the use of circular dichroism (CD) assays and equilibrium studies, which are known in the art). In additional embodiments, at least one property critical for binding affinity of the DN-TNF-α protein is altered when compared to the same property of wild type TNF-α and in particular, the DN-TNF-α protein has altered receptor affinity. Thus, DN-TNF-α proteins are of use in the methods disclosed herein have altered binding affinities such that the DN-TNF-α proteins will preferentially oligomerize with soluble wild type TNF-α, but do not substantially oligomerize with wild type transmembrane TNF-α or do not interact with wild type TNF-α receptors, i.e., p55, p75. By "do not substantially oligomerize with wild type transmembrane TNF" is meant that DN-TNF is unable to inhibit transmembrane TNF. By "do not substantially interact with TNF receptors" is meant that the DN-TNF-α proteins will not be able to associate with either the p55 or p75 receptors to significantly activate the receptor and initiate the TNF signaling pathway(s). In a some embodiments, at least a 50% decrease in receptor activation is seen, with greater than 50%, 76%, 80, 90%, 91%, 92%, 93%, 94%, or 95% as compared to trimmers of wild-type TNF-α. Dominant negative tumor necrosis factor α (DN-TNF-α) proteins are disclosed, for example, in PCT Publication No. WO 2014/040076; U.S. Pat. Nos. 7,446,174; and 7,662,367, which are all incorporated herein by reference.

In additional embodiments, the DN TNF-α protein has altered affinity toward oligomerization to wild type TNF-α. Thus, in some embodiments, given equal amounts of dominant-negative variant TNF-α monomers and wild type TNF-α monomers, at least 25% of the resulting trimers are mixed trimers of variant and wild type TNF-α, such as at least about 50%, at least about 60%, at least about 80%, at least about 90% or at least about 95% are mixtures of variant and wild type TNF-α. In some embodiments, the DN-TNF-α proteins have greater affinity for wild type TNF-α protein as compared to affinity of wild type TNF-α proteins. An exemplary amino acid sequence for human TNF-α is set forth below: VRSSSRTPSDKPVAHVVAN-PQAEGQLQWLNRRANALLANGVELRDNQLV-VPSEGLYLIYSQVLFKG QGCPSTHVLLTHTISRIAVSY-QTKVNLLSAIKSPCQRETPEGAEAKPWYEPIYLGGV-FQLEKGDRL SAEINRPDYLDFAESGQVYFGIIAL (SEQ ID NO: 1, see also U.S. Pat. No. 7,662,367, incorporated herein by reference, and FIG. 11)

A DN-TNF-α protein has an amino acid sequence that differs from a wild type TNF-α sequence by at least 1 amino acid, such as 1, 2, 3, 4, 5, 6, 7, 8, 9 and 10 amino acids or greater. Expressed as a percentage, a DN-TNF-α protein can be greater than 90% identical to wild-type, such as greater than 95, 96, 97, 98 and 99% identical to a wild-type TNF-α. The percentage of amino acid sequence identity value can be determined by the number of matching identical residues divided by the total number of residues of a "longer" sequence in the aligned region. The "longer" sequence is the one having the most actual residues in the aligned region (gaps introduced by WU-Blast-2 to maximize the alignment score are ignored). In a similar manner, "percent nucleic acid sequence identity" with respect to a nucleic acid encoding the protein can be the percentage of nucleotide residues in a candidate sequence that are identical with the nucleotide residues in the coding sequence for TNF-α. One method utilizes the BLASTN module of WU-BLAST-2 set to the default parameters, with overlap span and overlap fraction set to 1 and 0.125, respectively. Expressed as a percentage, a nucleic acid encoding a DN-TNF-α protein can be greater than 90% identical to wild-type, such as greater than 95, 96, 97, 98 and 99% identical to a wild-type nucleic acid sequence encoding wild-type TNF-α.

In some embodiments, based on the human TNF-α sequence of SEQ ID NO: 1, a DN-TNF-α protein has at least about 1 amino acid that differs from the human wild-type TNF-α sequence, such as at least about 2, 3, 4, 5, 6, 7 or 8 different amino acids. In some embodiments, a DN-TNF-α protein has 3 to 8 amino acids that differ from SEQ ID NO: 1 or SEQ ID NO: 2. An exemplary alignment of one DN-TNF-α and a wild type TNF-α is presented in FIG. 11.

DN-TNF-α proteins can be fused, for example, to other therapeutic proteins or to other proteins, such as Fc or serum albumin, for therapeutic or pharmacokinetic purposes. In this embodiment, a DN-TNF-α protein is operably linked to another moiety. In some embodiments, the moiety provides an intended therapeutic or pharmacokinetic effect. Examples of moieties include, but are not limited to, Human Serum Albumin, a therapeutic agent, a cytotoxic or cytotoxic molecule, radionucleotide, and an Fc, etc. As used herein, an Fc fusion is synonymous with the terms "immunoadhesin", "Ig fusion", "Ig chimera", and "receptor globulin" as used in the prior art (Chamow et al, 1996, Trends Biotechnol 14:52-60; Ashkenazi et al, 1997, Curr. Opin. Immunol. 9: 195-200, both incorporated by reference). An Fc fusion combines the Fc region of an immunoglobulin with the target-binding region of a TNF-α protein, for example. See for example U.S. Pat. Nos. 5,766,883 and 5,876,969, both of which are incorporated by reference. A DN-TNF-α protein can be PEGylated.

In one embodiment, the DN-TNF-α includes amino acid substitutions at one or more of the following positions: amino acid 21, 23, 30, 31, 32, 33, 34, 35, 57, 65, 66, 67, 69, 75, 84, 86, 87, 91, 97, 101, 111, 112, 115, 140, 143, 144, 145, 146, and 147. Exemplary amino acid substitutions for each position, including the human TNF-α residues, are shown in the table below, from PCT Publication No. WO 2014/040076, incorporated herein by reference.

| Wild-type TNF amino acid | Wild-type TNF amino acid number | Mutants created |
| --- | --- | --- |
| Q | 21 | R |
| N | 30 | D |
| R | 31 | I, D, E |
| R | 32 | D, E, S |
| A | 33 | E |
| A | 35 | S |
| K | 65 | D, T, M, W, I, Q, S, N, V, E |
| G | 66 | Q, K |
| Q | 67 | D, W, Y, R, K, S |
| A | 111 | R, E |
| K | 112 | D, E |
| Y | 115 | Q, K, E, N, R, F, H, M, L, I, W, D, T, S |
| D | 140 | R, K |
| D | 143 | E, N, Q, S, R, K |
| F | 144 | N |
| A | 145 | R, D, K, N, H, T, Q, E, Y, M, S, F |
| E | 146 | N, K, R, S |
| S | 147 | R |

ALSO MADE DOUBLE MUTANTS K65E/D143K, K65E/D143R, K65D/D143K AND K65D/D143R

As disclosed in PCT Publication No. WO 2014/040076, for example, at position 143, amino acids are Glu, Asn, Gln, Ser, Arg, and Lys can be utilized. This PCT Publication discloses that amino acid substitutions include: VIM, Q21 C, Q21 R, E23C, R31C, N34E, V91E, Q21R, N30D, R31C, R31I, R31D, R31E, R32D, R32E, R32S, A33E, N34E, N34V, A35S, D45C, L57F, L57W, L57Y, K65D, K65E, K65I, K65M, K65N, K65Q, K65T, K65S, K65V, K65W, G66K, G66Q, Q67D, Q67K, Q67R, Q67S, Q67W, Q67Y, C69V, L75E, L75K, L75Q, A84V, S86Q, S86R, Y87H, Y87R, V91E, I97R, I97T, CIOIA, A1 1 1R, A11IE, K1 12D, K1 12E, Y1 15D, Y1 15E, Y1 15F, Y1 15H, Y1 15I, Y1 15K, Y1 15L, Y1 15M, Y1 15N, Y1 15Q, Y1 15R, Y1 15S, Y1 15T, Y1 15W, D140K, D140R, D143E, D143K, D143L, D143R, D143N, D143Q, D143R, D143S, F144N, A145D, A145E, A145F, A145H, A145K, A145M, A145N, A145Q, A145R, A145S, A145T, A145Y, E146K, E146L, E146M, E146N, E146R, E146S and S147R. These amino acid substitutions can be included individually or in any combination. In some embodiments, at least 1 to 8 amino acid substitutions are included in a DN-TNF-α protein. The DN-TNF-α can include 1, 2, 3, 4, 5, 6, 7, 8, 9, 10, 11, 12, 13, 14, 15, 16, 17, 18, 19 or 20 amino acid substitutions.

In some embodiments, DN-TNF-α can be XENP268 XENP344, XENP345, XENP346, XENP550, XENP551, XENP557, XENP1593, XENP1594, and XENP1595 as outlined in Example 3 of U.S. Pat. No. 7,662,367, which is incorporated herein by reference. In one embodiment the DN-TNF-α is XPRO™ 1595, a PEGylated protein comprising V1M, R31C, C69V, Y87H, C101A, and A145R, (for example "<001<-V001M-R031C-µ031Peg10-0069V-Y087H-C101A-A0145R->157>") mutations relative to the wild type human sequence. The amino acid sequence for XPRO™ 1595 is shown in SEQ ID NO: 2. A nucleic acid sequence (SEQ ID NO: 3), encoding XPRO™ 1595 (SEQ ID NO: 2), is shown below:

```
aa    1  M  R  S  S    S  R  T  P    S  D  K  P    V  A  H  V
nt    1  ATGCGCTCCTCC  TCCCGCACTCCG  TCCGACAAACCG  GTAGCTCACGTA aa   17  V  A  N  P    Q  A  B  G    Q  L  Q  W    L  N  C  R
nt   49  GTAGCTAACCCG  CAGGCTGAAGGT  CAGCTGCAGTGG  CTGAACTGCCGC aa   33  A  N  A  L    L  A  N  G    V  E  L  R    D  N  Q  L
nt   97  GCTAACGCTCTG  CTGGCTAACGGT  GTAGAACTGCGC  GACAACCAGCTG aa   49  V  V  P  S    E  G  L  Y    L  I  Y  S    Q  V  L  F
nt  145  GTAGTACCGTCC  GAAGGTCTGTAC  CTGATCTACTCC  CAGGTACTGTTC aa   65  K  G  Q  G    V  P  S  T    H  V  L  L    T  H  T  I
nt  193  AAAGGTCAGGGT  GTTCCGTCCACT  CACGTACTGCTG  ACTCACACTATC aa   81  S  R  I  A    V  S  H  Q    T  K  V  N    L  L  S  A
nt  241  TCCCGCATCGCT  GTATCCCACCAG  ACTAAAGTAAAC  CTGCTGTCCGCT aa   97  I  K  S  P    A  Q  R  E    T  P  E  G    A  E  A  K
nt  289  ATCAAATCCCCG  GCGCAGCGCGAA  ACTCCGGAAGGT  GCTGAAGCTAAA aa  113  P  W  Y  E    P  I  Y  L    G  G  V  F    Q  L  E  K
nt  337  CCGTGGTACGAA  CCGATCTACCTG  GGTGGTGTATTC  CAGCTGGAARAA aa  129  G  D  R  L    S  A  E  I    N  R  P  D    Y  L  D  F
nt  385  GGTGACCGCCTG  TCCGCTGAAATC  AACCGCCCGGAC  TACCTGGACTTC aa  145  R  E  S  G    Q  V  Y  F    G  I  I  A    L  *
nt  433  CGCGAATCCGGT  CAGGTATACTTC  GGTATCATCGCT  CTGTAA
```

This sequence has the following features that are distinct from native soluble TNF: (1) replacement of the N-terminal valine with methionine, to facilitate a uniform translation product in *E. coli*; (2) replacement of tyrosine-87 with histidine and alanine-145 with arginine, to prevent TNF receptor binding; (3) replacement of arginine-31 with cysteine, to serve as a specific pegylation site; and (4) replacement of cysteine-69 with valine and cysteine-101 with alanine, to avoid mixed disulfide formation and eliminate heterogeneous pegylation sites. Each of the three monomer subunits of XENP550 has a theoretical molecular weight of 17,340 Da, and a pI of approximately 6.9. XPRO™ 1595 is produced by covalent conjugation of XENP550 with a single linear chain of approximately 10 kDa mPEG-maleimide per monomer subunit. The stable thioether-linked conjugate subunit has an approximate molecular weight of 27 kDa (81 kDa for the three subunits of active XPRO™ 1595. This molecule can be PEGylated.

In some embodiments, a DN-TNF-α protein interacts with the wild type TNF-α to form mixed trimers incapable of activating receptor signaling. In some examples, a DN-TNF-α protein has 1, 2, 3, 4, 5, 6, 7 or 8 amino acid substitutions, as compared to wild type TNF-α protein. In some embodiments, these amino acid substitutions are selected from positions 1, 21, 23, 30, 31, 32, 33, 34, 35, 57, 65, 66, 67, 69, 75, 84, 86, 87, 91, 97, 101, 111, 112, 115, 140, 143, 144, 145, 146 and 147. In an additional embodiments, the DN-TNF-α proteins have one or more of the following amino acid substitutions: V1M, Q21C, Q21R, E23C, N34E, V91E, Q21R, N30D, R31 C, R31I, R31D, R31E, R32D, R32E, R32S, A33E, N34E, N34V, A35S, D45C, L57F, L57W, L57Y, K65D, K65E, K65I, K65M, K65N, K65Q, K65T, K65S, K65V, K65W, G66K, G66Q, Q67D, Q67K, Q67R, Q67S, Q67W, Q67Y, C69V, L75E, L75K, L75Q, A84V, S86Q, S86R, Y87H, Y87R, V91E, I97R, I97T, CIOIA, AMR, All IE, K1 12D, K112E, Y115D, Y115E, Y115F, Y115H, Y115I, Y115K, Y115L, Y115M, Y115N, Y115Q, Y115R, Y115S, Y115T, Y115W, D140K, D140R, D143E, D143K, D143L, D143R, D143N, D143Q, D143R, D143S, F144N, A145D, A145E, A145F, A145H, A145K, A145M, A145N, A145Q, A145R, A145S, A145T, A145Y, E146K, E146L, E146M, E146N, E146R, E146S and S147R. Thus the DN-TNF-α protein can have 1, 2, 3, 4, 5, 6, 7 or 8 of these amino acid substitutions.

These substitutions may be made either individually or in combination, with any combination being possible. In some embodiments, one or more substitutions at positions 31, 57, 69, 75, 86, 87, 97, 101, 115, 143, 145, and 146 can be utilized, to form double variants. In addition triple, quadruple, quintuple and the like, point mutations may be generated. Thus, in some embodiments, a DN-TNF-α protein comprising the amino acid substitutions A145R I97T is utilized in the methods disclosed herein. In other embodiments, a DN-TNF-α protein including the amino acid substitutions VIM, R31C, C69V, Y87H, C101A, and A145R is utilized. Any of the disclosed DN-TNF-α proteins can be PEGylated.

In some embodiments, a wild type TNF-α protein is modified, which modified regions are selected from the group consisting of the large domain (also known as II), small domain (also known as I), the DE loop, and the trimer interface. The large domain, the small domain and the DE loop are the receptor interaction domains. DN-TNF-α can include amino acid substitutions solely in one of these areas or in any combination of these areas. The large domain can include amino acid substitutions at positions 21, 30, 31, 32, 33, 35, 65, 66, 67, 111, 112, 115, 140, 143, 144, 145, 146 and/or 147. For the small domain, the DN-TNF-α can include amino acid substitutions at positions 75 and/or 97. For the DE Loop, the DN-TNF-α protein can include amino acid substitutions at positions 84, 86, 87 and/or 91. The trimer interface can include double variants such as at positions 34 and 91 as well as at position 57. In some embodiments, substitutions at multiple receptor interaction and/or trimerization domains may be combined in the DN-TNF-α.

Examples include, but are not limited to, simultaneous substitution of amino acids at the large and small domains (for example, A145R and I97T), large domain and DE loop (for example, A145R and Y87H), and large domain and trimerization domain (for example, A145R and L57F). Additional examples include any and all combinations, e.g., I97T and Y87H (small domain and DE loop). In specific embodiments, these amino acid changes can be in the form of single point variants, for example K112D, Y115K, Y115I, Y115T, A145E or A145R. These single point variants may be combined, for example, Y115I and A145E, or Y1 15I and A145R, or Y115T and A145R or Y115I and A145E; or any other combination.

The DN-TNF-α can include double point substitutions at positions 57, 75, 86, 87, 97, 1 15, 143, 145, and 146; in any combination. In addition, the DN-TNF-α protein can include double point mutations such as L57F and one of Y115I, Y115Q, Y115T, D143K, D143R, D143E, A145E, A145R, E146K or E146R. Other double variants are Y115Q and at least one of D143N, D143Q, A145K, A145R, or E146K; Y115M and at least one of D143N, D143Q, A145K, A145R or E146K; and L57F and at least one of A145E or 146R; K65D and either D143K or D143R, K65E and either D143K or D143R, Y115Q and any of L75Q, L57W, L57Y, L57F, I97R, I97T, S86Q, D143N, E146K, A145R and I97T, A145R and either Y87R or Y87H; N34E and V91E; L75E and Y1 15Q; L75Q and Y115Q; L75E and A145R; and L75Q and A145R.]

In addition, the DN-TNF-α protein can include a triple point substitution. In some embodiments, substitutions are made, for example, as positions include 34, 75, 87, 91, 1 15, 143, 145 and 146. Examples of triple point variants include V91E, N34E and one of Y115I, Y115T, D143K, D143R, A145R, A145E E146K, and E146R. Other triple point DN_TNF-α proteins include L75E and Y87H and at least one of Y115Q, A145R. Exemplary DN-TNF-α proteins include 1) L75K, Y87H and Y1 15Q; or 2) V91E, N34E and either A145R or A145E.

DN-TNF-α proteins may also be identified as being encoded by variant TNF-a nucleic acids. As will be appreciated by those in the art, due to the degeneracy of the genetic code, an extremely large number of nucleic acids may be made, all of which encode the DN-TNF-α proteins of interest. Thus, having identified a particular amino acid sequence, those skilled in the art could make any number of different nucleic acids, by simply modifying the sequence of one or more codons in a way which does not change the amino acid sequence of the DN-TNF-α protein.

Nucleic acids encoding a DN-TNF-α protein are also of use in the methods disclosed herein. The nucleic acid molecule can be a cDNA. Recombinant nucleic acid molecules encoding the disclosed antibodies and antigen binding fragments can readily be produced by one of skill in the art, using the amino acid sequences provided herein, and the genetic code. In addition, one of skill can readily construct a variety of clones containing functionally equivalent nucleic acids, such as nucleic acids which differ in sequence but which encode the same protein sequence. Thus, nucleic acid molecules encoding the disclosed DN-TNF-α proteins are provided herein.

Nucleic acid sequences encoding a DN-TNF-α protein can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids encoding a DN-TNF-α protein can be prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

Polynucleotide sequences encoding a DN-TNF-α protein can be operatively linked to expression control sequences. Additional polypeptide can be encoded, such as, but not limited to antigen polypeptides. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding a DN-TNF-α protein can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

In one embodiment, vectors are used for expression in yeast such as *S. cerevisiae* or *Kluyveromyces lactis*. Several promoters are known to be of use in yeast expression systems such as the constitutive promoters plasma membrane $H^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, many inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (2μ) or single copy (CEN) plasmids to give an additional level of control in expression level. The plasmids can include nutritional markers (such as URA3, ADE3, HIS1, and others) for selection in yeast and antibiotic resistance (such as AMP) for propagation in bacteria. Plasmids for expression on *K. lactis* are known, such as pKLAC1. Thus, in one example, after amplification in bacteria, plasmids can be introduced into the corresponding yeast auxotrophs by methods similar to bacterial transformation.

The DN-TNF-α proteins can be expressed in a variety of yeast strains. For example, seven pleiotropic drug-resistant transporters, YOR1, SNQ2, PDR5, YCF1, PDR10, PDR11, and PDR15, together with their activating transcription factors, PDR1 and PDR3, have been simultaneously deleted in yeast host cells, rendering the resultant strain sensitive to drugs. Yeast strains with altered lipid composition of the plasma membrane, such as the erg6 mutant defective in ergosterol biosynthesis, can also be utilized. Proteins that are highly sensitive to proteolysis can be expressed in a yeast strain lacking the master vacuolar endopeptidase Pep4, which controls the activation of other vacuolar hydrolases. Heterologous expression in strains carrying temperature-sensitive (ts) alleles of genes can be employed if the corresponding null mutant is inviable.

Viral vectors encoding the DN-TNF-α proteins disclosed herein can also be prepared. A number of viral vectors have been constructed, including polyoma, SV40 (Madzak et al., 1992, *J. Gen. Virol.* 73:15331536), adenovirus (Berkner, 1992, *Curr. Top. Microbiol. Immunol.* 158:39-6; Berliner et al., 1988, *BioTechniques* 6:616-629; Gorziglia et al., 1992, *J. Virol.* 66:4407-4412; Quantin et al., 1992, *Proc. Natl. Acad. Sci. USA* 89:2581-2584; Rosenfeld et al., 1992, *Cell* 68:143-155; Wilkinson et al., 1992, *Nucl. Acids Res.* 20:2233-2239; Stratford-Perricaudet et al., 1990, *Hum. Gene Ther.* 1:241-256), vaccinia virus (Mackett et al., 1992, *Biotechnology* 24:495-499), adeno-associated virus (Muzyczka, 1992, *Curr. Top. Microbiol. Immunol.* 158:91-123; On et al., 1990, *Gene* 89:279-282), herpes viruses including HSV and EBV (Margolskee, 1992, *Curr. Top. Microbiol. Immunol.* 158:67-90; Johnson et al., 1992, *J. Virol.* 66:2952-2965; Fink et al., 1992, *Hum. Gene Ther.* 3:11-19; Breakfield et al., 1987, *Mol. Neurobiol.* 1:337-371; Fresse et al., 1990, *Biochem. Pharmacol.* 40:2189-2199), Sindbis viruses (Herweijer et al., 1995, *Hum. Gene Ther.* 6:1161-1167; U.S. Pat. Nos. 5,091,309 and 5,2217,879), alphaviruses (Schlesinger, 1993, *Trends Biotechnol.* 11:18-22; Frolov et al., 1996, *Proc. Natl. Acad. Sci. USA* 93:11371-11377) and retroviruses of avian (Brandyopadhyay et al., 1984, *Mol. Cell Biol.* 4:749-754; Petropouplos et al., 1992, *J. Virol.* 66:3391-3397), murine (Miller, 1992, *Curr. Top. Microbiol. Immunol.* 158: 1-24; Miller et al., 1985, *Mol. Cell Biol.* 5:431-437; Sorge et al., 1984, *Mol. Cell Biol.* 4:1730-1737; Mann et al., 1985, *J. Virol.* 54:401-407), and human origin (Page et al., 1990, *J. Virol.* 64:5370-5276; Buchschalcher et al., 1992, *J. Virol.* 66:2731-2739). Baculovirus (Autographa californica multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

Thus, in one embodiment, the polynucleotide encoding a DN-TNF-α protein is included in a viral vector. Suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus and the like.

Viral vectors, such as poxviral vectors, that encode a DN-TNF-α protein include at least one expression control element operationally linked to the nucleic acid sequence encoding the a DN-TNF-α protein. The expression control elements are inserted in the viral vector to control and regulate the expression of the nucleic acid sequence. Examples of expression control elements of use in these vectors includes, but is not limited to, lac system, operator and promoter regions of phage lambda, yeast promoters and promoters derived from polyoma, adenovirus, retrovirus or SV40. Additional operational elements include, but are not limited to, leader sequence, termination codons, polyadenylation signals and any other sequences necessary for the appropriate transcription and subsequent translation of the nucleic acid sequence encoding the DN-TNF-α protein in the host system. The expression vector can contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (Ausubel et al., (1987) in "Current Protocols in Molecular Biology," John Wiley and Sons, New York, N.Y.) and are commercially available.

Basic techniques for preparing recombinant DNA viruses containing a heterologous DNA sequence encoding the one or more proteins are known in the art. Such techniques involve, for example, homologous recombination between the viral DNA sequences flanking the DNA sequence in a donor plasmid and homologous sequences present in the parental virus (Mackett et al., 1982, *Proc. Natl. Acad. Sci. USA* 79:7415-7419). In particular, recombinant viral vectors such as a poxviral vector can be used in delivering the gene. The vector can be constructed for example by steps known in the art, such as steps analogous to the methods for creating synthetic recombinants of the fowlpox virus described in U.S. Pat. No. 5,093,258, incorporated herein by reference. Other techniques include using a unique restriction endonuclease site that is naturally present or artificially inserted in the parental viral vector to insert the heterologous DNA.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or functional (antigen binding) fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Isolation and purification of recombinantly expressed polypeptide can be carried out by conventional means including preparative chromatography and immunological separations. Once expressed, the a DN-TNF-α protein can be purified according to standard procedures of the art, including ammonium sulfate precipitation, affinity columns, column chromatography, and the like (see, generally, R. Scopes, *Protein Purification*, Springer-Verlag, N.Y., 1982). Substantially pure compositions of at least about 90 to 95% homogeneity are disclosed herein, and 98 to 99% or more homogeneity can be used for pharmaceutical purposes. Once purified, partially or to homogeneity as desired, if to be used therapeutically, the polypeptides should be substantially free of endotoxin.

In addition to recombinant methods, a DN-TNF-α protein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A*. pp. 3-284; Merrifield et al., *J. Am. Chem. Soc.* 85:2149-2156, 1963, and Stewart et al., *Solid Phase Peptide Synthesis*, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N, N'-dicylohexylcarbodimide) are well known in the art.

Pharmaceutical Compositions and Methods of Use

Methods are disclosed herein for preventing carcinogenesis and/or inhibiting formation of a tumor, treating a tumor, or reducing the risk of developing a tumor. In some embodiments, methods are disclosed herein for preventing conversion of a benign to a malignant lesion, or preventing metastasis. Thus, the tumor can be benign or malignant. In some embodiments, the tumor is an inflammatory tumor. Methods are disclosed herein for treating a subject with a tumor.

The methods include administering to a subject a therapeutically effective amount of dominant negative tumor necrosis factor (DN-TNF)-α protein, and/or a nucleic acid encoding the DN-TNF-α protein. The nucleic acid encoding the DN-TNF-α protein can be included in an expression vector (see above). The method can include administering a pharmaceutical composition including the DN-TNF-α protein, and/or a nucleic acid encoding the DN-TNF-α protein, and a pharmaceutically acceptable carrier. Administration can be systemic or local. Any of the DN-TNF-α proteins disclosed above can be used in the disclosed methods. In specific, non-limiting embodiments, the DN-TNF-α protein comprises, or consists of, the amino acid sequence of SEQ ID NO: 2.

In some embodiments, methods are provided for inhibiting the development of tumor. These methods can include inhibiting an immunosuppressive response to the cancer in the subject. The immunosuppressive response can be expression of an immunosuppressive cytokine. The expression of the cytokine can be reduced, for example, by 20% 30%, 40%, 50%, 60%, 70%, 80%, 90%, or 95% as compared to a control. In specific, non-limiting examples, the cytokine is interleukin (IL)-1α, TGFβ and IL-10. The control can be the expression of the cytokine in the absence of administration of the DN-TNF-α, such as in a sample from a subject prior to administration of the DN-TNF-α. The control can be a standard value.

The immunosuppressive response can include myeloid derived suppressor cells (MDSC). Thus, in some embodiments, the disclosed methods reduce the number of MDSC. The number of MDSC can be reduced, for example, by 20% 30%, 40%, 50%, 60%, 70%, 80%, 90%, or 95% as compared to a control. The control can be the number of MDSC in the absence of administration of the DN-TNF-α, such as in a sample from a subject prior to administration of the DN-TNF-α. The control can be a standard value.

The immunosuppressive response can also include depletion or functional exhaustion of T helper and T cytotoxic cells. In some embodiments, the disclosed methods increase the number and/or function of T helper and T cytotoxic cells. The number and/or function (as measured, for example, by cytokine secretion and/or tumor killing) of T helper and T cytotoxic cells can be increased, for example, by 20%, 30%, 40%, 50%, 60%, 70%, 80%, 90%, or 95% as compared to control. The control can be the number of T helper and T cytotoxic cells in the absence of administration of the DN-TNF-α, such as in a sample from a subject prior to administration of the DN-TNF-α. The control can be a standard value.

In additional embodiments, inhibiting the development of the tumor comprises stimulating an immune response to the tumor in the subject. The immune response can include a Th1 response and/or cross-talk of natural killer (NK) cells and dendritic cells (DCs). In some embodiments, the "cross-talk" is the interaction between NK cells and DCs via membrane bound ligands such as transmembrane TNF and trans-presented IL-15, and secreted cytokines such as IL-12 and IFNγ, which reciprocally stimulate and activate these innate immunity effector cells. The immune response can include production of a cytokine, such as IL-1β, IL-12, IL-17 and/or IFNγ. The immune response can include an increased anti-cancer T cell response or B cell response. The immune response can be increased, for example, by 20% 30%, 40%, 50%, 60%, 70%, 80%, 90%, or 95% as compared to a control. The control can be the immune response, such as the NK cell/DC cross-talk, cytokine production or specific reactions to tumor antigens of B cells and T cells, in the absence of administration of the DN-TNF-α, such as in a sample from a subject prior to administration of the DN-TNF-α. The control can be a standard value.

In further embodiments, the method can include preventing the carcinogenesis and/or development of a tumor, or inhibiting the development of a tumor, such as a benign or malignant tumor. The method can include inhibiting the conversion of a benign tumor to a malignant tumor. In a specific, not limiting example, the size and number of tumors can be decreased in the subject as compared to a control. The tumors can be primary tumors and metastasis, including, but not limited to, micrometastasis. In additional, non-limiting examples, the control is an untreated subject or a subject treated with a carrier.

The methods disclosed herein include selecting a subject in need of treatment for the condition. In certain embodiments, the subject has a predisposition to develop the tumor, or is at risk of developing a tumor. In some embodiments, the subject is exposed to a carcinogen, the subject is exposed to radiation, or a subject has a premalignant condition. The subject can have or previously had a tumor, or have a predisposition to developing the tumor, such as due to their medical history. The subject can have a genetic predisposition to developing the tumor. In one embodiment, the method prevents or delays recurrence of the tumor in the subject. Additional agents optionally can be administered to the subject of interest. In several embodiments, methods are provided for decreasing the risk of developing a tumor in a subject exposed to a carcinogen, or preventing or delaying the development of a tumor.

Treatment can be prophylactic or, alternatively, can be initiated after the development of a condition, such as a precancerous lesion or a non-malignant tumor. Treatment that is prophylactic, for instance, can be initiated before a subject manifests symptoms of a condition. In a specific, non-limiting example, the subject can have polyps of the colon, but does not have colon cancer. In some examples, such as for skin cancer, treatment can be initiated before or during exposure to an agent that damages DNA, such as a result of an exposure to a carcinogen or UV light, oxidative stress, alkylation damage and deamination. In some examples, treatment can be following the exposure to the DNA damaging agent, a virus associated with cancer (for example, hepatitis C virus (HCV) and B viruses (HBV), human papilloma virus (HPV) or human immunodeficiency virus (HIV)) but before the appearance of a tumor. In some examples, treatment can be before or during exposure to a carcinogen, such as an occupational exposure, such as to asbestos and smoking, or to viral infections, such as to HBV, HCV, HPV and HIV, such as for a subject at risk of lung cancer, liver cancer, cervical cancer and laryngeal cancer or Kaposi's sarcoma, respectively. Treatment can be before the development of a condition, such as, but not limited to, a subject with a BRCA1 and/or BRCA2 mutation who is at risk of developing breast cancer. Treatment prior to the development of the condition is referred to herein as treatment of a subject that is "at risk" of developing the condition. Accordingly, administration of a composition can be performed before, during, or after the occurrence of the conditions described herein. In some embodiments, the disclosed methods reduce the risk of developing a tumor.

Non-limiting examples of subjects particularly suited to receiving the DN-TNF-α are those who may be exposed to natural or artificial UV irradiation, subjects who are exposed to a carcinogen due to an occupational exposure to an industrial chemical, or due to smoking. The subject can be exposed to asbestos or silica, and thus be at risk for mesothelioma. In some examples, these subjects have not yet developed tumors. Examples of subjects suited to treatment are smokers who have not developed lung cancer. Examples of subjects suited to treatment also are those exposed to large amounts of UV light, but who have not developed skin cancer, such as a melanoma or a basal cell carcinoma. Additional examples of subjects suited to treatment are those subjects who have or will have an occupational exposure to a carcinogen, such as asbestos.

The disclosed methods can be used to treat metastatic cancer, such as to inhibit metastases or prevent additional metastasis. In some embodiments, the disclosed methods can be used to reduce the development of a tumor or additional tumors in a subject, such as to reduce the volume and number of lesions. The methods are of use to inhibit or prevent the development of metastasis, or to decrease the number of micrometastases, such as micrometastases to the regional lymph nodes (see Goto et al., *Clin. Cancer Res.* 14(11):3401-3407, 2008). Treatment initiated after the development of an initial tumor condition may result in decreasing the severity of the symptoms of one of the conditions, or completely removing the symptoms, or reducing metastasis, tumor volume or number of tumors. In some examples, these subjects have an existing benign tumor that can convert into a malignant or even metastatic lesion. In this aspect of the disclosure, the formation of tumors are delayed, prevented or decreased. In some embodiments, the disclosed methods can be used to prevent development of metastatic cancer.

The tumor can be any tumor of interest, including solid tumors and hematological tumors. Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma). Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia. In specific, non-limiting examples, the tumor is a breast cancer, prostate cancer, lung cancer, liver cancer, cervical cancer, head and neck cancer, melanoma, renal cell carcinoma, Kaposi's sarcoma or colon cancer.

The presence of a tumor can be determined by methods known in the art, and typically include cytological and morphological evaluation. The cells can be in vivo or ex vivo, including cells obtained from a biopsy.

Any DN-TNF-α protein disclosed herein, and/or a nucleic acid encoding the DN-TNF-α, can be used in any of the disclosed methods. In specific, non-limiting examples, the DN-TNF-α protein comprises or consists of the amino acid sequence set forth as SEQ ID NO: 2. The DN-TNF-α protein, and/or nucleic acid encoding the DN-TNF-α protein, can be formulated in a variety of ways for administration to a subject to inhibit, prevent, reduce the risk of developing any tumor of interest. The DN-TNF-α protein disclosed herein, and/or a nucleic acid encoding the DN-TNF-α, can be administered in a pharmaceutically acceptable carrier.

The DN-TNF-α protein and/or nucleic acid encoding the DN-TNF-α protein, can be administered alone or in conjunction with additional agents. Pharmaceutical compositions can include DN-TNF-α protein and/or nucleic acid encoding the DN-TNF-α protein as disclosed herein as an active ingredient, or include both a DN-TNF-α protein and/or nucleic acid encoding the DN-TNF-α protein and an additional agent, such as an additional anti-inflammatory, anti-immunosuppression agent (for example, an anti-PD-1 antibody, an anti-CTLA-4 blocking antibody, Treg-reducing cyclophosphamide and/or an anti-IL-2Rα antibody), immunostimulating agent (for example, anti-epidermal growth factor receptor (EGFR) antibodies, OX40 agonists, CD40 agonists, a vaccine and/or a cytokine such as IFNα, IL-2), immuno-restoring agent (for example, stem cell factor (SCF), granulocye macrophage colony stimulating factor (GM-CSF), macrophage colony stimulating factor (M-CSF), Fms related tyrosine kinase (Flt)3-ligand, interleukin (IL)-7 and/or stem cells) or chemotherapeutic agent. Exemplary chemotherapeutic agents are small molecule inhibitors or antibodies targeting mutated $BRAF^{V600E}$ or MEK. However, the chemotherapeutic agent can be any chemotherapeutic agent of interest, such as cisplatin, carboplatin, gemcitabine, dacarbazine, temozolomide, paclitaxel and others.

Pharmaceutical compositions are thus provided for both local (such as topical, intra-tumoral, or inhalational) use and for systemic (such as oral or intravenous) use. Therefore, the disclosure includes within its scope pharmaceutical compositions comprising at a DN-TNF-α protein and/or nucleic acid encoding the DN-TNF-α protein formulated for use in human or veterinary medicine. While the DN-TNF-α protein and/or nucleic acid encoding the DN-TNF-α protein will typically be used to treat human subjects they may also be used to treat similar or identical diseases in other vertebrates, such as other primates, dogs, cats, horses, and cows. A suitable administration format may best be determined by a medical practitioner for each subject individually. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42: 2S, 1988. The dosage form of the pharmaceutical composition will be determined by the mode of administration chosen.

In one embodiment, a therapeutically effective amount of a DN-TNF-α protein and/or nucleic acid encoding the DN-TNF-α protein is formulated for administration to the skin. Formulations suitable for topical administration can include dusting powders, ointments, creams, gels or sprays for the administration of the active compound to cells, such as skin cells. Such formulations may optionally include an inorganic pigment, organic pigment, inorganic powder, organic powder, hydrocarbon, silicone, ester, triglyceride, lanolin, wax, cere, animal or vegetable oil, surfactant, polyhydric alcohol, sugar, vitamin, amino acid, antioxidant, free radical scavenger, ultraviolet light blocker, sunscreen agents, preservative, fragrance, thickener, or combinations thereof. Additives can be included such as, for example, preservatives, bactericides, perfumes, antifoams, dyes, pigments which have a coloring action, surfactants, thickeners, suspending agents, fillers, moisturizers, humectants, fats, oils, waxes or other customary constituents of a cosmetic formulation, such as alcohols, polyols, polymers, foam stabilizers, electrolytes, organic solvents, or silicone derivatives.

The DN-TNF-α protein and/or nucleic acid encoding the DN-TNF-α protein can be formulated for administration by inhalation, such as, but not limited to, formulations for the treatment of lung or esophageal cancer. Inhalational preparations include aerosols, particulates, and the like. In general, the goal for particle size for inhalation is about 1 μm or less in order that the pharmaceutical reach the alveolar region of the lung for absorption. However, the particle size can be modified to adjust the region of disposition in the lung. Thus, larger particles can be utilized (such as about 1 to about 5 μm in diameter) to achieve deposition in the respiratory bronchioles and air spaces. In addition, oral formulations may be liquid (e.g., syrups, solutions, or suspensions), or solid (e.g., powders, pills, tablets, or capsules).

For administration by inhalation, the compounds can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

The compositions or pharmaceutical compositions also can be administered by any route, including parenteral administration, for example, intravenous, intraperitoneal, intramuscular, intraperitoneal, intrasternal, intrathecal, or intraarticular injection or infusion, or by sublingual, oral, topical, intranasal, or transmucosal administration. When a DN-TNF-α protein and/or nucleic acid encoding the DN-TNF-α protein is provided as parenteral compositions, e.g. for injection or infusion, they are generally suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate-acetic acid buffers. A form of repository or "depot" slow release preparation may be used so that therapeutically effective amounts of the preparation are delivered into the bloodstream over many hours or days following transdermal injection or delivery.

A DN-TNF-α protein and/or nucleic acid encoding the DN-TNF-α protein are also suitably administered by sustained-release systems. Suitable examples of sustained-release formulations include suitable polymeric materials (such as, for example, semi-permeable polymer matrices in the form of shaped articles, e.g., films, or mirocapsules), suitable hydrophobic materials (such as, for example, an emulsion in an acceptable oil) or ion exchange resins, and sparingly soluble derivatives (such as, for example, a sparingly soluble salt). Sustained-release compositions can be administered orally, rectally, parenterally, intracistemally, intravaginally, intraperitoneally, topically (as by powders, ointments, gels, drops or transdermal patch), bucally, or as an oral or nasal spray.

Preparations for administration can be suitably formulated to give controlled release of a DN-TNF-α protein and/or nucleic acid encoding the DN-TNF-α protein over an extended period of time. For example, the pharmaceutical compositions may be in the form of particles comprising a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features which allow a controlled release of the active substance. See U.S. Pat. No. 5,700,486.

For oral administration, the pharmaceutical compositions can take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring, and sweetening agents as appropriate. For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

The pharmaceutically acceptable carriers and excipients of use are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

Generally, the formulations are prepared by contacting the DN-TNF-α protein and/or the nucleic acid encoding the DN-TNF-α protein uniformly and intimately with liquid carriers or finely divided solid carriers or both. Then, if necessary, the product is shaped into the desired formulation. Optionally, the carrier is a parenteral carrier, and in some embodiments it is a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

Additionally, contacting the DN-TNF-α protein and/or the nucleic acid encoding the DN-TNF-α protein can be administered by implanting (either directly into an organ (e.g., intestine or liver) or subcutaneously) a solid or resorbable matrix which slowly releases the compound into adjacent and surrounding tissues of the subject. For example, for the treatment of gastrointestinal precancerous lesions, the compound may be administered systemically (e.g., intravenously, rectally or orally) or locally (e.g., directly into a tumor. Alternatively, the DN-TNF-α protein and/or a nucleic acid encoding the DN-TNF-α protein can be impregnated into a wafer or resorbable sponge and placed in direct contact with tissue, such as gastric tissue. The contacting the DN-TNF-α protein and/or the nucleic acid encoding the DN-TNF-α protein is slowly released in vivo by diffusion of from the wafer and erosion of the polymer matrix. As another example, viral infection of the liver (i.e., hepatitis) is treated by infusing into the liver vasculature a solution containing the contacting the DN-TNF-α protein and/or the nucleic acid encoding the DN-TNF-α protein.

Where the therapeutic compound is a nucleic acid encoding a DN-TNF-α protein, the nucleic acid can be administered in vivo to promote expression of the encoded protein, by constructing it as part of an appropriate nucleic acid expression vector and administering it so that it becomes intracellular, such as by use of a retroviral vector, by direct injection, by use of microparticle bombardment, by coating with lipids or cell-surface receptors or transfecting agents, or by administering it in linkage to a homeobox-like peptide which is known to enter the nucleus (See, e.g., Joliot, et al., Proc Natl Acad Sci USA 88:1864-1868, 1991), and the like. Alternatively, a nucleic acid therapeutic is introduced intracellularly and incorporated within host cell DNA for expression, by homologous recombination or remain episomal.

For local administration of DNA, standard gene therapy vectors can be used. Such vectors include viral vectors, including those derived from replication-defective hepatitis viruses (such as HBV and HCV), retroviruses (see, PCT Publication No. WO 89/07136; Rosenberg et al., N. Eng. J. Med. 323(9):570-578, 1990, adenovirus (see, Morsey et al., J. Cell. Biochem., Supp. 17E, 1993), adeno-associated virus (Kotin et al., Proc. Natl. Acad. Sci. USA 87:2211-2215, 1990), replication defective herpes simplex viruses (HSV; Lu et al., Abstract, page 66, Abstracts of the Meeting on Gene Therapy, September 22-26, Cold Spring Harbor Laboratory, Cold Spring Harbor, N.Y., 1992), and any modified versions of these vectors. Any of the vectors disclosed above can be utilized, or any other delivery system that accomplishes in vivo transfer of nucleic acids into eukaryotic cells. For example, the nucleic acids may be packaged into liposomes, such as cationic liposomes (Lipofectin), receptor-mediated delivery systems, non-viral nucleic acid-based vectors, erythrocyte ghosts, or microspheres (such as microparticles; see, e.g., U.S. Pat. Nos. 4,789,734; 4,925, 673; 3,625,214). Naked DNA may also be administered.

Dosage for any given patient depends upon many factors, including the patient's size, body surface area, age, the particular compound to be administered, sex, time and route of administration, general health, and other drugs being administered concurrently. Dosages may vary, but a preferred dosage for intravenous administration of DNA is approximately 106 to 1022 copies of the DNA molecule.

Typically, plasmids are administered to a mammal in an amount of about 1 nanogram to about 5000 micrograms of DNA. Desirably, compositions contain about 5 nanograms to 1000 micrograms of DNA, 10 nanograms to 800 micrograms of DNA, 0.1 micrograms to 500 micrograms of DNA, 1 microgram to 350 micrograms of DNA, 25 micrograms to 250 micrograms of DNA, or 100 micrograms to 200 micrograms of DNA. Alternatively, administration of recombinant viral vectors, such as adenoviral vectors, encoding the PD-1 antagonist into a mammal may be administered at a concentration of at least 105, 106, 107, 108, 109, 1010, or 1011 plaque forming unit (pfu).

The pharmaceutical compositions that includes a DN-TNF-α protein and/or a nucleic acid encoding the DN-TNF-α protein, in some embodiments, can be formulated in unit dosage form, suitable for individual administration of precise dosages. The amount of active compound (s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated. Multiple treatments are envisioned, such as over defined intervals of time, such as daily, bi-weekly, weekly, bi-monthly or monthly, such that chronic administration is achieved. As disclosed herein, therapeutically effective amounts of a DN-TNF-α protein and/or a nucleic acid encoding the DN-TNF-α protein are of use preventing formation of a tumor, preventing conversion of a benign to a malignant lesion, decreasing the risk of developing a tumor, or preventing metastasis. Administration may begin whenever the suppression or prevention of disease is desired, for example, at a certain age of a subject, or prior to an environmental exposure. Suitable doses are disclosed, for example, in U.S. Pat. No. 7,662,367, which is incorporated herein by reference. The exact dose is readily determined by one of skill in the art based on the potency of the specific compound (such as the DN-TNF-α protein utilized), the age, weight, sex and physiological condition of the subject.

Methods for measuring the immune response following treatment using the methods disclosed herein are well known in the art. The activity of immune cells can be assessed, for example, by assays that detect cytokine production; assays measuring antigen-stimulated $CD8^+$ and $CD4^+$ T cell number, proliferation, cytotoxicity and cytokine production; and assays that measure number and functions of MDSCs. Exemplary assays are disclosed below, and, for example, in U.S. Pat. No. 6,808,710 and U.S. Patent Application Publication Nos. 2004/0137577, 2003/0232323, 2003/0166531, 2003/0064380, 2003/0044768, 2003/0039653, 2002/0164600, 2002/0160000, 2002/0110836, 200/20107363, and 2002/0106730.

A therapeutically effective amount of a DN-TNF-α protein and/or a nucleic acid encoding the DN-TNF-α protein can be administered with a therapeutically effective amount of another agent. The administration can be simultaneous or sequential. It should be noted that, while the paragraphs below disclose the agents individually, any combination of these agents can be utilized.

The agent can be, for example, a chemotherapeutic agent (such as, but not limited to, inhibitors targeting $BRAF^{V600E}$ and/or Mitogen-activated protein kinase kinase (MEK)), radiation, a cytokine, a chemokine, an antibody, cells (activated NK cells, dendritic cells, antigen specific CD8 or CD4 T cells, hematopetic stem cells) or an immunostimulatory agent (OX40 agonists, CD40 agonists, or an anti-EGFR antibody). In some examples, the agent can be with surgical treatment. The agent can be a cytokine, including, but not limited to, IL-2, IL-7, IL-15, or an interferon (IFN), such as IFN-α or IFN-γ.

A therapeutically effective amount of a DN-TNF-α protein and/or a nucleic acid encoding the DN-TNF-α protein can be administered with a therapeutically effective amount of an antibody, such as an anti-programmed death (PD)-1 antibody, an anti-programmed death ligand (PD-L)1 antibody, an anti-PD-L2 antibody, an anti-lymphocyte activation gene (LAG3) antibody, an anti-T cell immunoglobulin and mucin protein (TIM)-3 antibody, an anti-T cell immunoreceptor with Ig and ITIM domains (TIGIT) (see Johnson et al., Cancer Cell. 2014 Dec. 8; 26(6):923-37. doi: 10.1016/j.ccell.2014.10.018, incorporated by reference herein), or an anti-cytotoxic T-lymphocyte-associated protein 4 (CTLA-4) antibody. Antibodies include monoclonal antibodies, humanized antibodies, deimmunized antibodies, and immunoglobulin (Ig) fusion proteins.

The amino acid sequence of antibodies that bind PD-1 are disclosed, for example, in U.S. Patent Publication No. 2006/0210567, which is incorporated herein by reference. Antibodies that bind PD-1 are also disclosed in U.S. Patent Publication No. 2006/0034826, which is also incorporated herein by reference. The antibody can be KEYTRUDA® (pembrolizumab). The antibody can be an anti-PD-1 antibody such as Nivolumab (ONO-4538/BMS-936558) or OPDIVO® from Ono Pharmaceuticals. In several examples, the antibody specifically binds PD-1 or a PD-L1 or PD-L2 with an affinity constant of at least $10^7$ $M^{-1}$, such as at least $10^8$ $M^{-1}$ at least $5 \times 10^8$ $M^{-1}$ or at least $10^9$ $M^{-1}$. The antibody can be an anti-CTLA-4 antibody, such as Ipilmumab (also known as MDX-010 and MDX-101 and YERVOY®). The antibody can be an anti-TIM-3 antibody, anti-LAG3 antibody or anti-TIGIT antibody. The additional agent can stimulate OX40 and/or CD40. The additional agent can be an antibody that stimulates OX40, such as an anti-OX40 antibody. In one example, the antibody available from AgonOX. The agent can be an antibody that stimulates CD40, such as CP-870 or CP-893 (Pfizer). The antibody can be an antibody that specifically binds CD40 ligand. The agent can be an antibody that specifically binds CD137, (4-1BB; an inducible costimulatory target).

The DN-TNF-α protein, or nucleic acid encoding the DN-TNF-α protein, can be administered with a vaccine, such as a tumor vaccine. The vaccine can be a synthetic peptide vaccine, a recombinant protein vaccine, a tumor lysate vaccine, or a nucleic acid (DNA or RNA) vaccine. A vaccine can include a bacterial adjuvant, a viral adjuvant or cell adjuvant (e.g. dendritic cells). The vaccine can include, for example, a whole-length MUC-1 protein, a lysed tumor cell that contains MUC-1, a MUC-1 polypeptide, a nucleic acid sequence encoding a MUC-1 polypeptide, or a dendritic cell loaded with any MUC-1 format. Tumor vaccines include, but are not limited to, BIOVAXID® (prostate, dasiprotimut-T), PROVENGE® (sipuleucel-T), Oncophage, PROSTVAC® (PSA-TRICOM®, Bavarian Nordic), CV-301 (colon, bladder and breast, Bavarian Nordic), MVA-BN PRO, MVA-BN HER2, or MVA-BN Brachyury (see the Bavarian Nordic website). Tumor vaccines also include: a) CDX-1401 (NCI) (DEC-205/NY-ESO-1 fusion protein vaccine for melanoma; ovarian, fallopian tube or primary peritoneal cancer in remission; myelodysplastic syndrome and acute myeloid leukemia); b) PANVAC (NCI) (MUC1 and CEA vaccine; non-muscle invasive bladder cancer, pancreatic cancer, breast cancer); c) MAGE-A3 (GSK) (melanoma and non-small cell lung carcinoma); d) PRAME (GSK) (non-small cell lung carcinoma, metastatic skin cancer); e) ISA101 (ISA Pharmaceuticals) (HPV16 synthetic long peptide vaccine for cervical cancer; f) ISA203 (ISA Pharmaceuticals) (PRAME (Preferentially expressed Antigen in Melanoma)).

The vaccine can include MUC-1 (or a nucleic acid encoding MUC-1). MUC-1 is a high-molecular-weight glycoprotein that is densely glycosylated with O-linked carbohydrates. It is produced in few isoforms including both a transmembranal and its cleavage truncated secreted (soluble) product. MUC-1 is normally expressed polarized to the apical surface of glandular epithelial cells at low levels. In cancers, MUC-1 loses polarity and is highly increased and decreases its glycosylation. MUC-1 is expressed by more than 90% of solid epithelial tumor cancers as well as most common non-solid tumors including colon, lung, pancreas, breast, ovarian, prostate, kidney, stomach and head and neck cancers. Due to its low glycosylation, tumor MUC-1 is recognized by the immune system and induces immune response leading to production of MUC-1 specific antibodies and cytotoxic T cells. The tumor variant of MUC-1 and its peptides have been used as antigens for anti-cancer vaccines, see Kimura and Finn. Expert Opin. Biol. Ther. 13(1): 35-49, 2013; Kimura et al., Cancer Prev. Res. (Phila) 6(1):18-26. Epub 2012 Dec. 17. Additional suitable antigens are disclosed in the table below.

The DN-TNF-α protein, or nucleic acid encoding the DN-TNF-α protein, can be administered with a chemotherapeutic agent or radiation therapy. Examples of chemotherapeutic agents are alkylating agents, antimetabolites, natural products, hormones and their antagonists or small molecule inhibitors of signaling molecules. Examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine). Examples of antimetabolites include folic acid analogs (such as methotrexate), pyrimidine analogs (such as 5-FU or cytarabine), and purine analogs, such as mercaptopurine or thioguanine. Examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase). Examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide). Examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of small molecule inhibitors include vemurafenib (ZELBORAF®), dabrafenib (TAFINLAR®) and Trametinib (MEKINIST®) that have been FDA-approved for the treatment of human cancers harboring $BRAF^{V600E}$ mutation. Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (GEMZAR®), HERCEPTIN®, Irinotecan (Camptosar, CPT-11), LEUSTATIN®, NAVELBINE®, RITUXAN® STI-571, TAXOTERE®, Topotecan (HYCAMTIN®), XELODA® (Capecitabine), ZEVELIN® and calcitriol.

The DN-TNF-α protein, or nucleic acid encoding the DN-TNF-α protein, can be administered in conjunction with a steroidal anti-inflammatory agent or a non-steroidal anti-inflammatory agents. Steroidal anti-inflammatory agents include glucocorticoids, dexamethasone, prednisone, and hydrocortisone. Non-steroidal anti-inflammatory agents include salicylates (such as Acetylsalicylic acid (Aspirin), amoxiprin, benorylate/benorilate, choline magnesiu salicylate, diflunisal, ethenzamide, faislamine, methyl salicylate, magnesium salicylate, salicyl salicylate, salicylamide) arylalkanoic acids (such as diclofenac, aceclofenac, acemethacin, alclofenac bromfenac, etodolac, indomethacin, nabumetone, oxametacin, proglumetacin, sulindac, tolmetin), 2-arylpropionic acids (such as ibuprofen, alminoprofen, carprofen, dexibuprofen, dexketoprofen, fenbufen, fenoprofen, flunoxaprofen, flurbiprofen, ibuproxam, indoprofen, ketorolac, loxoprofen, naproxen, oxaprozin, pirprofen, suprofen, tiaprofenic acid), N-arylanthranilic acids (such as mefenamic acid, flufenamic acid, meclofenamic acid, tolfenamic acid) pyrazolidine derivatives (such as phenylbutazone, ampyrone, azapropazone, clofezone, kebuzone, metamizole, mofebutazone, oxyphenbutazone, phenazone, sulfinpyrazone) oxicams (such as piroxicam, droxicam, lornoxicam, meloxicam, tenoxicamo or COX-2 inhibitors.

In some embodiments, the methods include the administration of a therapeutically effective amount of T cells, such as cytotoxic T cells specific for an antigen of interest, such as a tumor antigen. In one example, the method includes isolating from the donor a population of cells that include T cells (such as peripheral blood mononuclear cells, tumor-infiltrating lymphocytes (TILs), or lymph node) and stimulating these cells with a population of antigen presenting cells (APCs) from the donor that are presenting an antigen of interest, thereby producing a population of donor cells comprising activated donor $CD4^+$ and/or $CD8^+$ T cells depleted for alloreactive T cells that recognize a tumor antigen of interest. A therapeutically effective amount of the population of donor activated CD4+ and/or CD8+ cells is infused, optionally with IL-2, into the recipient, thereby producing an immune response to the antigen of interest. The method can induce an antitumor reaction in the recipient. Thus, an immune response is produced in the recipient against the antigen of interest, such as a tumor antigen.

Any antigenic peptide (such as an immunogenic fragment) from an antigen of interest can be used to generate a population of T cells specific for that antigen of interest. Numerous such antigenic peptides are known in the art, see, for example, the Table below. This disclosure is not limited to using specific antigens. Particular examples of antigens of interest, include, but are not limited to, those antigens that are tumor antigens, such as those shown in the table. Additional antigenic proteins are known in the art (for example see Novellino et al., *Cancer Immunol. Immunother.* 54(3):187-207, 2005, and Chen et al., *Cytotherapy,* 4:41-8, 2002, both herein incorporated by reference).

| Exemplary tumors and their tumor antigens | |
|---|---|
| Tumor | Tumor Antigens |
| Acute myelogenous leukemia | Wilms tumor 1 (WT1), preferentially expressed antigen of melanoma (PRAME), PR1, proteinase 3, elastase, cathepsin G, PRAME |
| Chronic myelogenous leukemia | WT1, PRAME, PR1, proteinase 3, elastase, cathepsin G, PRAME |
| Myelodysplastic syndrome | WT1, PRAME, PR1, proteinase 3, elastase, cathepsin G, PRAME |

Exemplary tumors and their tumor antigens

| Tumor | Tumor Antigens |
|---|---|
| Acute lymphoblastic leukemia | PRAME |
| Chronic lymphocytic leukemia | Survivin, PRAME |
| Non-Hodgkin's lymphoma | Survivin, PRAME |
| Multiple myeloma | New York esophageous 1 (NY-ESO-1), PRAME |
| Malignant melanoma | MAGE, MART, Tyrosinase, PRAME, GP100, Survivin, NY-ESO-1, PRAME |
| Breast cancer | WT1, herceptin, MUC-1, Survivin, MAGE, NY-ESO-1, PRAME |
| Lung cancer | WT1, MUC-1, Survivin, NY-ESO-1, PRAME |
| Prostate cancer | Prostate-specific antigen (PSA), Prostate-specific membrane antigen (PSMA), MUC-1, Survivin, NY-ESO-1, PRAME |
| Colon cancer | Carcinoembryonic antigen (CEA), MUC-1, PRAME, Survivin, NY-ESO-1 |
| Renal cell carcinoma (RCC) | Fibroblast growth factor 5 (FGF-5), MUC-1, Survivin, NY-ESO-1, PRAME |
| Hepatocellular carcinoma (HCC) | AFP, MUC-1, WT1, MAGE, Survivin, NY-ESO-1, PRAME |

Although the table discloses full-length antigens of interest, one skilled in the art will recognize that fragments or the full-length protein can also be used in the methods disclosed herein. In one example, an antigen of interest is an "immunogenic fragment" of a full-length antigen sequence. An "immunogenic fragment" refers to a portion of a protein which, when presented by a cell in the context of a molecule of the MHC, can in a T-cell activation assay, activate a T-cell against a cell expressing the protein. Typically, such fragments that bind to MHC class I molecules are 8 to 12 contiguous amino acids of a full length antigen, although longer fragments may of course also be used. In some examples, the immunogenic fragment is one that can specifically bind to an MHC molecule on the surface of an APC, without further processing of the epitope sequence. In particular examples, the immunogenic fragment is 8-50 contiguous amino acids from a full-length antigen sequence, such as 8-20 amino acids, 8-15 amino acids, 8-12 amino acids, 8-10 amino acids, or 8, 9, 10, 11, 12, 13, 14, 15 or 20 contiguous amino acids from a full-length antigen sequence. In some examples, APCs are incubated with the immunogenic fragment under conditions sufficient for the immunogenic fragment to specifically bind to MHC molecules on the APC surface, without the need for intracellular processing.

Generally, the APCs and the T cells are autologous. In specific, non-limiting examples, the APCs and the responder T cells are from the same individual. However, the APCs and the responder T cells can be syngeneic. The APC can be used to present any antigen to a population of autologous T cells. One of skill in the art will appreciate that antigenic peptides that bind to MHC class I and II molecules can be generated ex vivo (for example instead of being processed from a full-length protein in a cell), and allowed to interact with (such as bind) MHC I and II molecules on a cell surface. Generally, APCs present antigen in the context of both MHC class I and II.

In one example, the antigen of interest incubated with the APCs is a fusion protein that includes an amino acid sequence from the antigen of interest (such as 8-50 contiguous amino acids, for example 8-15 or 8-12 contiguous amino acids from the antigen of interest). Thus, a series of MHC binding epitopes can be included in a single antigenic polypeptide, or a single chain trimer can be utilized, wherein each trimer has an MHC class I molecule, a b2 microglobulin, and an antigenic peptide of interest (see Nature 2005; vol. 436, page 578). In some examples, only a single antigen is used, but in other embodiments, more than one antigen is used, such as at least 2 different antigens, at least 3 different antigens, at least 4 different antigens, at least 5 different antigens, at least 10 different antigens, at least 15 different antigens, at least 20 different antigens, or even at least 50 different antigens.

A therapeutically effective amount of antigen-specific T cells can be administered to the subject in addition to the DN-TNF-α protein or a nucleic acid encoding the DN-TNF-α protein. Specific, non-limiting examples of a therapeutically effective amount of purified antigen-specific T cells include purified antigen-specific T cells administered at a dose of about $1\times10^5$ cells per kilogram of subject to about $1\times10^9$ cells per kilogram of subject, such as from about $1\times10^6$ cells per kilogram to about $1\times10^8$ cells per kilogram, such as from about $5\times10^6$ cells per kilogram to about $75\times10^6$ cells per kilogram, such as at about $25\times10^6$ cells per kilogram, or at about $50\times10^6$ cells per kilogram. Purified antigen-specific T cells can be administered in single or multiple doses as determined by a clinician. For example, the cells can be administered at intervals of approximately two weeks depending on the response desired and the response obtained. The administration can be local or systemic.

The disclosure is illustrated by the following non-limiting Examples.

EXAMPLES

Tumor necrosis factor (TNF) is a potent promoter of carcinogenesis and potentially important target for cancer prevention. TNF is produced as functionally distinct transmembrane and soluble molecules (tmTNF and sTNF, respectively). The participation of tmTNF and sTNF in chemically induced carcinogenesis in mice was investigated (Sobo-Vujanovic, A. et al., 2016, *Cancer Immunol Res.* 4(5):441-51, incorporated herein by reference). It was determined that intraperitoneal injection of XPRO™ 1595, a dominant-negative TNF biologic (DN-TNF) and specific antagonist of sTNF, strikingly decreased tumor incidence and growth, and prolonged survival of 3-methylcholanthrene (MCA)-injected mice. Similar results were obtained following the exclusion of both TNF forms by either TNF-receptor 2-Fc fusion protein (TNFR2-Fc) treatment or TNF-gene deletion. In addition, gene-deletion of TNFR1, which preferentially interacts with sTNF, temporarily blocked, whereas gene-deletion of TNFR2, which preferentially interacts with tmTNF, enhanced MCA-induced carcinogenesis. Concomitantly with carcinogenesis induction, MCA enhanced circulating IL-1α levels, and expansion of myeloid-derived suppressor-cells (MDSCs), STAT5 phosphorylation and immunosuppressive activity among splenocytes. In sharp contrast, DN-TNF treatment dramatically decreased IL-1α, and increased the central immunoregulatory cytokines IL-1β, IL-12p70 and IL-17 in the peripheral blood of MCA-injected mice. Furthermore, DN-TNF treatment, TNFR2-Fc treatment and/or gene deletion of TNF or TNFR1, but not of TNFR2, prevented MDSC expansion, STAT3 phosphorylation and immunosuppression in MCA-injected mice. It was determined that sTNF is both a pivotal regulator of MDSCs and an essential promoter of carcinogenesis; and indicate that sTNF could be a significant target for cancer prevention. See also Vjuanovic et al., Cancer Immunol. Res. 4: 441-451, 2016, DOI: 10.1158/2326-6066.CIR-15-0104, incorporated herein by reference.

Example 1

Materials and Methods

Mice

Eight-week-old wild-type C57BL/6 (B6), T-cell/B-cell-deficient SCID (B6;129S7-Rag1$^{tm1mom}$/J), TNF-deficient (TNFko, B6;129S-Tnf$^{m1Gkl}$/J), TNFR1-deficient (TNFR1ko, B6;129S-Tnfrsf1a$^{tm11mx}$ Il1r1$^{tm11mx}$/J) and TNFR2-deficient (TNFR2ko, B6.129S2-Tnfrsf1b$^{tm1Mwm}$/J) female mice were purchased from The Jackson Laboratory (Bar Harbor, Me.). Mice were housed in an internationally accredited animal facility. The animal studies were performed in accordance with approved protocols.

Reagents

The following reagents, antibodies and kits were used in the present study: recombinant human interleukin-2 (IL-2) (Chiron Corp., Emeryville, Calif.); TLR4 ligand, *Escherichia coli* lipopolysaccharide (LPS) (Lonza, Walkersville, Md.); human TNFR2-Fc fusion protein (etanercept, ENBREL; Amgen, Thousand Oaks, Calif.); XPRO™ 1595 dominant negative TNF construct (DN-TNF; Xencor, Monrovia, Calif.); fluorescein isothiocyanate (FITC)-conjugated anti-CD3, anti-CD4 anti-CD11b and anti-CD45R monoclonal antibodies (mAbs); phycoerythrin (PE)-conjugated anti-CD3, anti-Gr1 (Ly-6G), anti-CD25, anti-NK1.1 (Ly55), anti-NKp46 (CD335), anti-CD11c and anti-F4/80 mAbs; allophycocyanin (APC)-conjugated anti-Ly6C, anti-FoxP3 and anti-CD8 mAbs (all against mouse CDs); and corresponding fluorochrome-conjugated isotype control mAbs (all mAbs from eBioscience Inc., San Diego, Calif.); PE-conjugated IgG2a mAbs to phosphorylated pSTAT3 (STAT3 Tyr705, pSTAT3 Ser727) and isotype control mAbs (BD Biosciences, San Jose, Calif.); mouse Quantikine IFN-γ enzyme-linked immunosorbent assay (ELISA) kit (R&D Systems); and Millipore mouse 32-plex cytokine kit (Billerica, Mass.).

Induction, Treatment and Measurement of Carcinogenesis In Vivo

Wild-type and TNF-, TNFR1- and TNFR2-deficient B6 mice were injected subcutaneously (s.c.), in the shaved dorsal region, with 0.1 mg 3-methylcholanthrene (MCA) dissolved in 0.1 mL sesame oil (Sigma, St. Louis, Mo.). The wild-type B6 mice were then divided by randomization into groups of 10-15 mice each, as noted in Results. PBS, XPRO™ 1595-DN-TNF and TNFR2-Fc-ENBREL (200 µg/0.5 mL PBS/mouse) were injected intraperitoneally (i.p.) twice a week, for 12 weeks, starting on the day of MCA injection. The appearance of 2-mm diameter tumors was detected by palpation twice weekly. The subsequent tumor growth was determined by measuring two perpendicular tumor-diameters with calipers twice weekly. The data are presented as multiplications of two tumor diameters of established individual tumors and their mean values. The survival of mice was scored daily.

In Vitro Assessment of DC/NK-Cell Crosstalk Suppression

Endogenous DC/NK-cell crosstalk was assessed as follows. Splenocytes ($2\times10^6$/mL) of untreated and treated wild-type mice were resuspended in complete cell-culture medium (CM) consisted of RPMI-1640 medium, 0.1 mM nonessential amino acids, 2 mM sodium pyruvate, 1 mM L-glutamine, 100 µg/ml streptomycin, 100 U/mL penicillin, 10% fetal calf serum (FCS, Life Technologies, Grand Island, N.Y.) and 50 µM 2-mercaptoethanol (Bio-Rad, Hercules, Calif.); and supplemented with 1 µg/mL LPS and 6,000 IU/mL IL-2. The cell suspensions (100,000 cells/200 µL/well) were seeded in a 96-well round bottom plate (BD Biosciences, San Jose, Calif.) and incubated at 37° C., for 24 h.

The assessment of cell-mediated suppression of DC/NK-cell crosstalk was performed as follows: Suspensions of SCID-mouse splenocytes (100,000/well, mixture of 50% NK1.1$^+$NKp46$^+$CD3$^-$NK cells and 30% CD11c$^+$ iDCs, and 20% F4/80$^+$ monocytes/macrophages) and splenocytes of untreated or treated wild-type mice (100,000 and 300,000/well) in CM supplemented with LPS (1 µg/mL) and IL-2 (6,000 IU/mL) were mixed seeded in 96-well round bottom plates, and incubated at 37° C., for 24 hours (h). The assays were performed in triplicates. Following the incubations, cell-free supernatants were collected and examined for the presence of IFN-γ using ELISA.

Flow Cytometry

Standard cell-surface flow cytometry with fluorochrome-conjugated antibodies was performed as previously described (17). B cells (CD45R$^+$F4/80$^-$), macrophages (CD45R$^-$F4/80$^+$), NK cells (CD3$^-$NK.1.1$^+$ or CD3$^-$NKp46$^+$) and DCs (CD11b$^\pm$CD11c$^+$), CD4 (CD3$^+$CD4$^+$CD8$^-$) and CD8 (CD3$^+$CD4$^-$CD8$^+$) T cells, monocytic (CD11b$^+$Gr$^{lo/-}$Ly6C$^{+/hi}$) and granulocytic (CD11b$^+$Gr$^{hi}$Ly6C$^+$) MDSCs were examined using direct multi-color cell surface staining Treg (CD4$^+$Foxp3$^+$CD25$^{hi}$) were examined per Treg-kit manufacturer protocol (Biolegend, San Diego, Calif.). Phosphorylated STAT5 was investigated as previously described (21). Cells were analyzed on Cyan Blue flow cytometer (Beckman Coulter, Brea, Calif.). Analyses of the flow-cytometry data were performed using Summit 4.3 software (Beckman Coulter).

Quantification of Cytokines

Cytokines were quantified in peripheral-blood sera using Millipore multiplex-mouse-cytokine kit, as recommended by the company. IFN-γ was measured in the cell-culture-conditioned media using Quantikine mouse-IFN-γ ELISA kit (R&D). The amounts of cytokines in 1 mL sera or cell-culture-conditioned media were determined.

Statistics

Data were statistically evaluated using the SPSS (version 10.0 SPSS Inc., Chicago, Ill.) and R (version 3.0.2. see the R-project.org website) program packages. The data are reported as means±SD. Statistical significance of data was assessed using the Student's t test. In addition, the Kaplan-Meier method was used to analyze the time to cancer appearance (cumulative hazard for tumor development) and survival. Exact-log-rank tests were used to compare the time-to-cancer appearance and survival curves of experimental and control groups. p values≤0.05 were considered significant.

Example 2

MCA-Induced Carcinogenesis is Prevented by Selective Sequestration of Soluble TNF DN-TNF selectively sequesters sTNF without affecting tmTNF, and inhibits the inflammatory reactions without impacting the major immune mechanisms that control intracellular pathogens and cancer (Vujanovic, Immunol. Res. 2011; 50:159-74; Van Hauwermeiren et al., Cytokine & Growth Factor Reviews 2011; 22:311-9). In contrast, TNFR2-Fc neutralizes both sTNF and tmTNF, and inhibits both the inflammatory reactions and major immune mechanisms (Xu et al., Blood 2007; 109:3333-41; Vujanovic et al., Blood 2010; 116:575-583; Vujanovic, Immunol. Res. 2011; 50:159-74; Van Hauwermeiren et al., Cytokine & Growth Factor Reviews 2011; 22:311-9). The impact of DN-TNF-XPRO™ 1595 and TNFR2-Fc-ENBREL was initially examined on MCA-induced carcinogenesis in wild-type B6 mice (FIG. 1A). It was found that small 4 mm² tumors began to appear in all mice regardless of treatment on week 4 after MCA injection. The incipient tumors were strikingly more frequent in PBS-treated than in ENBREL-treated and, especially, DN-TNF-treated mice. The differences in tumor frequencies between PBS-treated and ENBREL-treated, PBS-treated and DN-TNF-treated, or ENBREL-treated and DN-TNF-treated mice were significant ($p=0.009$, $p<0.00005$, and $p=0.027$, respectively).

Figure 1B:
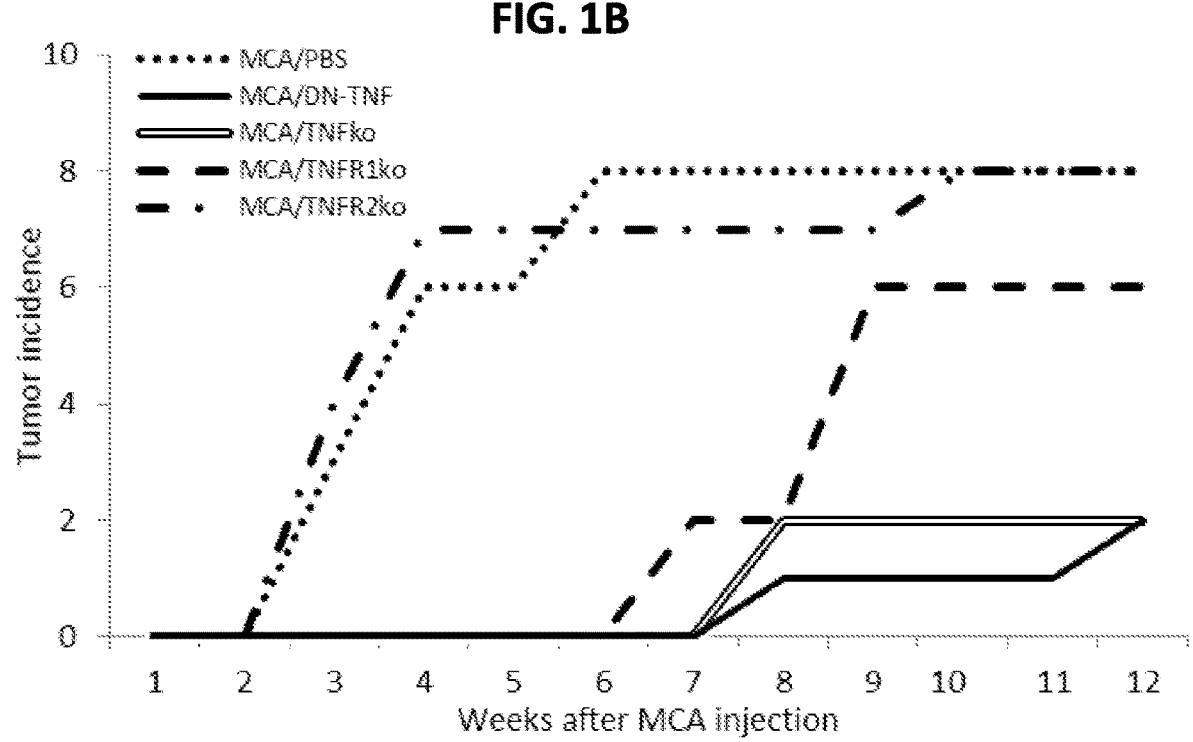

To confirm the initial findings and to evaluate deeper the roles of sTNF and tmTNF in chemically induced carcinogenesis, the effects of phosphate buffered saline (PBS)- and DN-TNF-treatment (sTNF-sequestration) was examined in wild-type mice with the effects of TNF, TNFR1 and TNFR2 deletion (exclusions: sTNF and tmTNF, sTNF-receptor and tmTNF-receptor, respectively) in the gene-deficient mice on MCA-induced carcinogenesis. In this experiment, tumor incidence (FIG. 1B), tumor size (FIG. 1C) and survival (FIG. 1D) were monitored. The time and incidence of tumor occurrence varied between the experimental groups (FIG. 1B). In PBS-treated wild-type and untreated TNFR2-deficient mice, 4 mm² incipient tumors appeared early and in the majority of animals (week 4: 6/10 and 7/10 mice, respectively). In these test groups, the tumor incidence reached maximum (8/10 mice) on weeks 6 and 10, respectively. In sharp contrast, the specific sequestration of sTNF by DN-TNF in wild-type mice, exclusion of sTNF activity by knocking-out TNFR1, or exclusion of both sTNF and tmTNF by knocking-out TNF led to a delayed (3 to 4 weeks) and infrequent (1/10, 2/10 and 2/10 mice, respectively) occurrence of tumors. While the low tumor incidence remained unchanged in TNF-deficient and DN-TNF-treated mice, it notably increased in TNFR1-deficient mice (from 2/10 to 6/10 mice) on week 9 after MCA injection. The differences in tumor frequencies between PBS-treated and DN-TNF-treated, TNF-deficient or TNFR1-deficient mice were significant ($p=0.0007$, $p=0.0016$, and $p=0.031$, respectively). Similarly, the differences in tumor frequencies between TNFR2-deficient and DN-TNF-treated, TNF-deficient or TNFR1-deficient mice were also significant ($p=0.0013$, $p=0.0026$ and $p=0.029$, respectively).

Figure 1C:
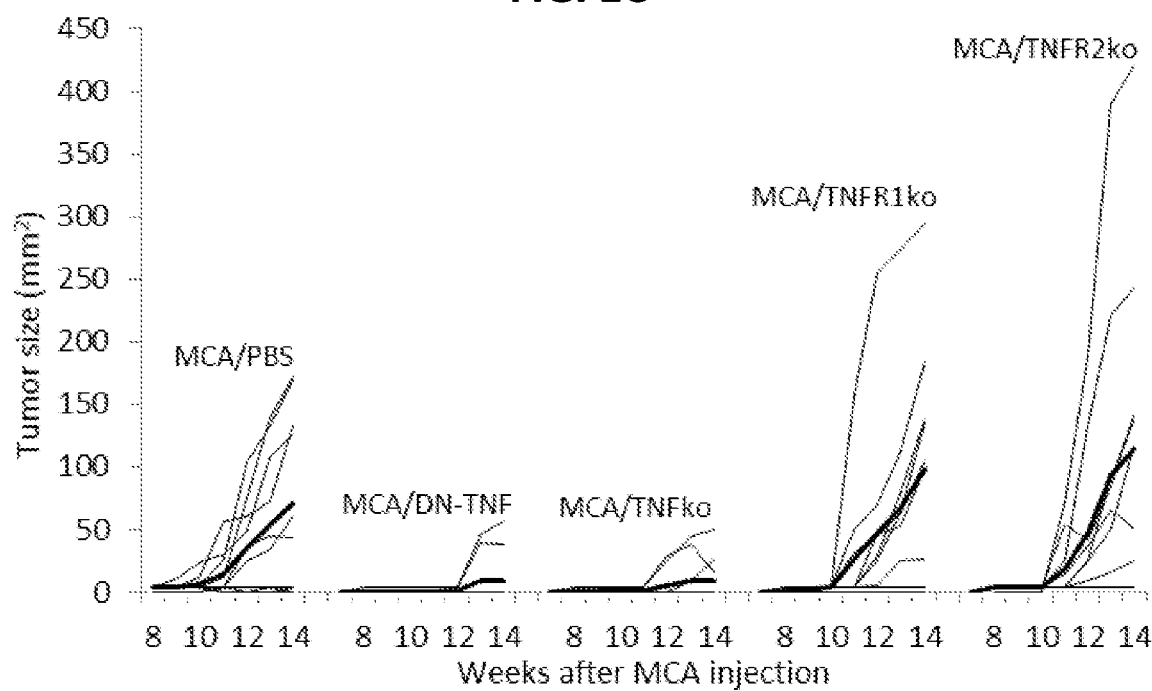

Tumors grew slowly or remained dormant in all groups of mice until week 10 after MCA-injection. Afterwards, in the test groups with frequent tumors (PBS-treated wild-type and TNFR1- and TNFR2-deficient mice), the tumors grew with a variable velocity and differed widely in size within each group, at all-time points of their measurements. In sharp contrast, the infrequent tumors in DN-TNF-treated and TNF-deficient mice remained small (4-9 mm²) and dormant until week 12 after MCA injection. Thus, between weeks 10 and 14 after MCA injection, tumors were significantly larger in PBS-treated, TNFR1-deficient and TNFR2-deficient mice than in DN-TNF-treated and TNF-deficient mice (vs DN-TNF: $p=0.017$, $p=0.023$ and $p=0.029$; vs TNF-knockout: $p=0.027$, $p=0.031$ and $p=0.036$, respectively) (FIG. 1C).

Figure 1D:
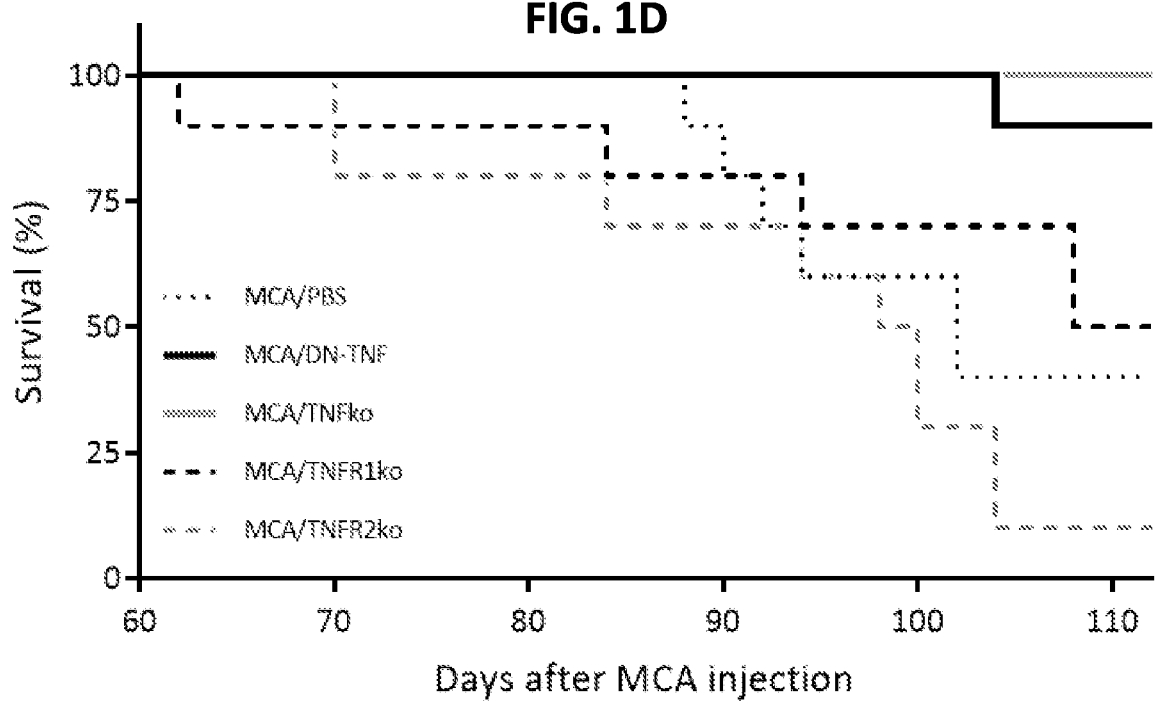

The strikingly lower tumor frequency and slower tumor growth in DN-TNF-treated wild-type and TNF-deficient mice than in PBS-treated wild-type, TNFR1-deficient and TNFR2-deficient mice resulted in significant prolongation of mouse survival. At the end point of the experiment, day 112 (week 16) after MCA injection, 9/10 DN-TNF-treated wild-type and 10/10 TNF-deficient mice were alive. In sharp contrast, only 5/10 TNFR1-deficient (vs DN-TNF and TNFko: $p=0.001$, $p=0.003$, respectively), 4/10 PBS-treated (vs DN-TNF and TNFko: $p=0.0026$, $p=0.0037$, respectively) and 1/10 TNFR2-deficient (vs DN-TNF and TNFko: $p=0.00033$, $p=0.00012$, respectively) mice were alive (FIG. 1D).

These findings demonstrate that sTNF is critical for MCA-induced carcinogenesis, while tmTNF is dispensable. They also indicate that tmTNF, in contrast to sTNF, can have a protective role in carcinogenesis.

Example 3

Sequestration of sTNF Modulates Immunoregulatory Cytokines in MCA-Injected Mice

Figure 2A:
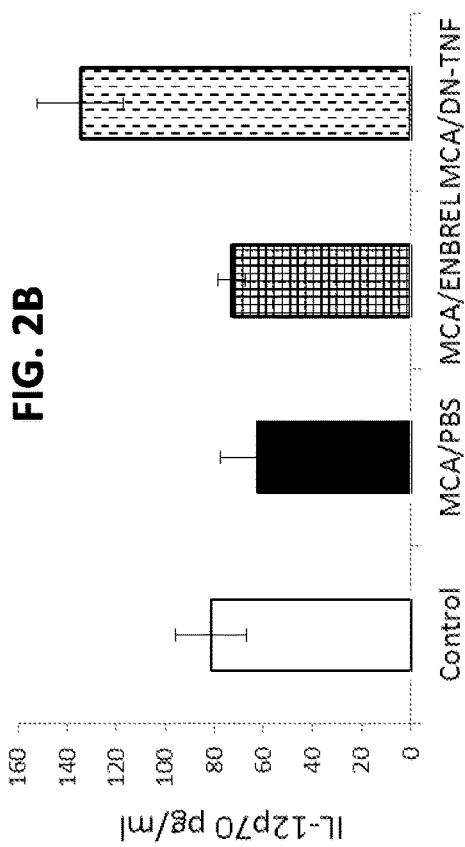
FIGS. 2A-2D. Sequestration of sTNF with XPRO™ 1595 DN-TNF and neutralization of both sTNF and tmTNF by TNFR2-Fc affect secretion of immunoregulatory cytokines in MCA-injected mice. Healthy/untreated (Control), MCA-injected/PBS-treated (MCA), MCA-injected/TNFR2-Fc-treated (MCA/ENBREL) and MCA-injected/XPRO™ 1595-treated (MCA/DN-TNF) wild-type mice (3 mice per each group) were sacrificed and their sera obtained 14 days after MCA-injection. The sera were examined for the presence of IL-1β (FIG. 2A), IL-12p40/70 (FIG. 2B), IL-17 (FIG. 2C) and IL-1α (FIG. 2D) using the LUMINEX® assay. The data represent mean values of triplicates+SE.
Figure 2B:
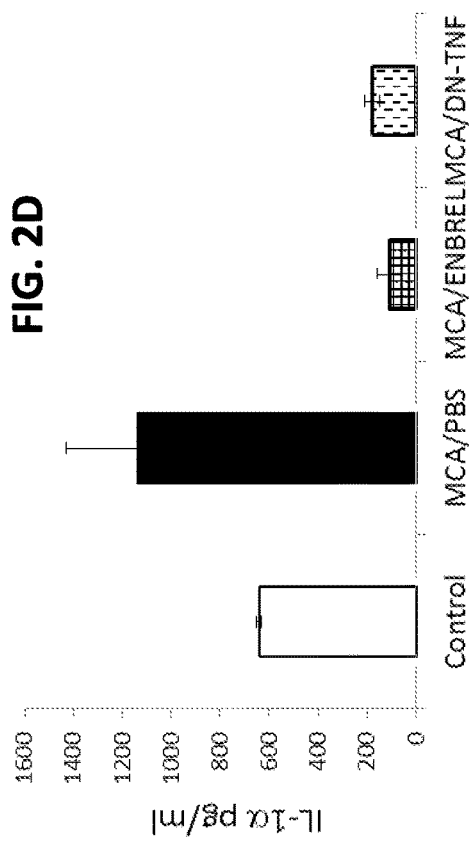
Figure 2C:
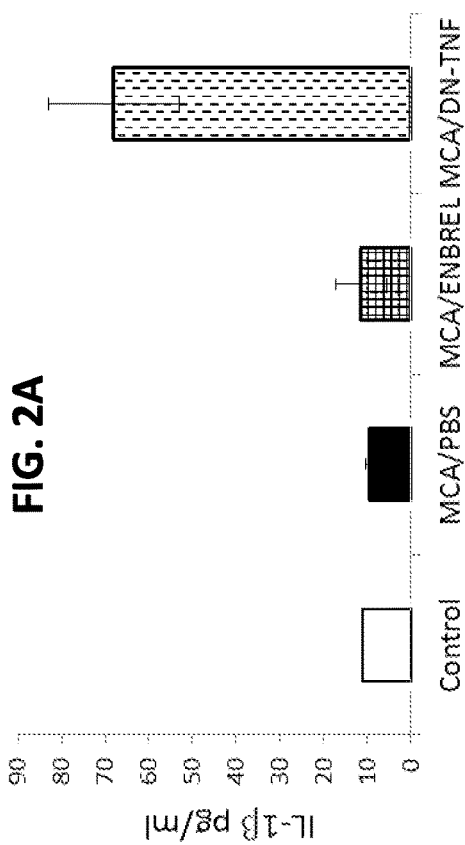
Figure 2D:
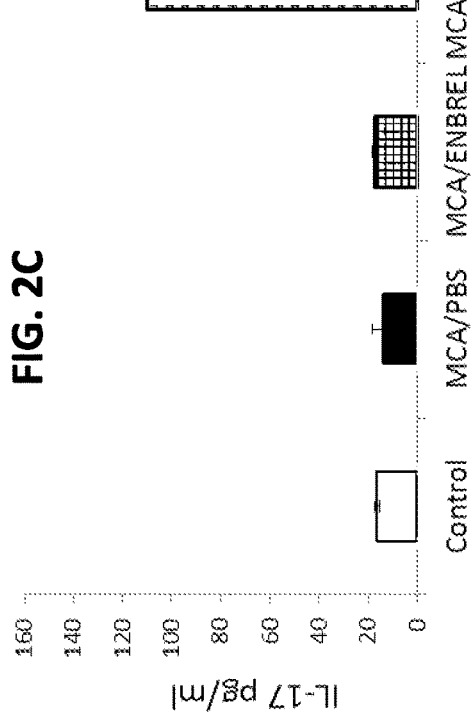

MCA-induced cancers are immunogenic (Cicinnati et al., Int J Cancer 2005; 13:961-70). Therefore, a modified and/or enhanced anti-tumor immune response could cause the increased resistance to MCA-induced carcinogenesis after sTNF exclusion. Type and quantity of secreted cytokines define type and effectiveness of anti-tumor immune responses. Levels of cytokines were examined in the sera of healthy/untreated (Control) and MCA-injected/PBS-, ENBREL- or DN-TNF-treated mice, two weeks after MCA injection (FIG. 2). In MCA-injected/PBS-treated mice, the central proinflammatory, Th1 and Th17 cytokines, IL-1β, IL-12p40/p70 and IL-17, respectively, were either unchanged (IL-1β, IL-17; FIGS. 2A, 2C) or slightly decreased (IL-12p40/p70, FIG. 2B) relative to control mice. In sharp contrast, the levels of these cytokines significantly increased in MCA-injected/DN-TNF-treated mice (IL-1β: $p=0.026$; IL-12p40/70: $p=0.05$; IL-17; $p=0.039$). The cytokines did not change in MCA-injected/ENBREL-treated mice. In contrast, IL-1α levels were high in control mice, notably increased in MCA-injected/PBS-treated mice, but strongly decreased below control levels by ENBREL ($p=0.012$) or DN-TNF ($p=0.023$) treatment. These findings indicate that sTNF suppresses and sTNF-sequestration enables inflammasome (IL-1β), Th1 (IL-12) and Th17 (IL-17) responses in MCA-injected mice. Because these responses did not differ in healthy/untreated control and MCA-injected/ENBREL-treated mice (neutralized both sTNF and tmTNF), the increased responses after sTNF-sequestration could be mediated by tmTNF. In addition, the high baseline and MCA-induced augmentation of IL-1α, which were strongly suppressed by ENBREL or DN-TNF, indicates that sTNF up-regulates IL-1α. Intriguingly, at this early stage of carcinogenesis, sTNF was not detectable in the sera of MCA-injected/untreated or treated mice. Thus, sTNF could be initially present in biologically significant quantities only in target tissues.

Example 4

MCA Induces and sTNF Sequestration Averts MDSC Expansion

Figures 3A, 3B:
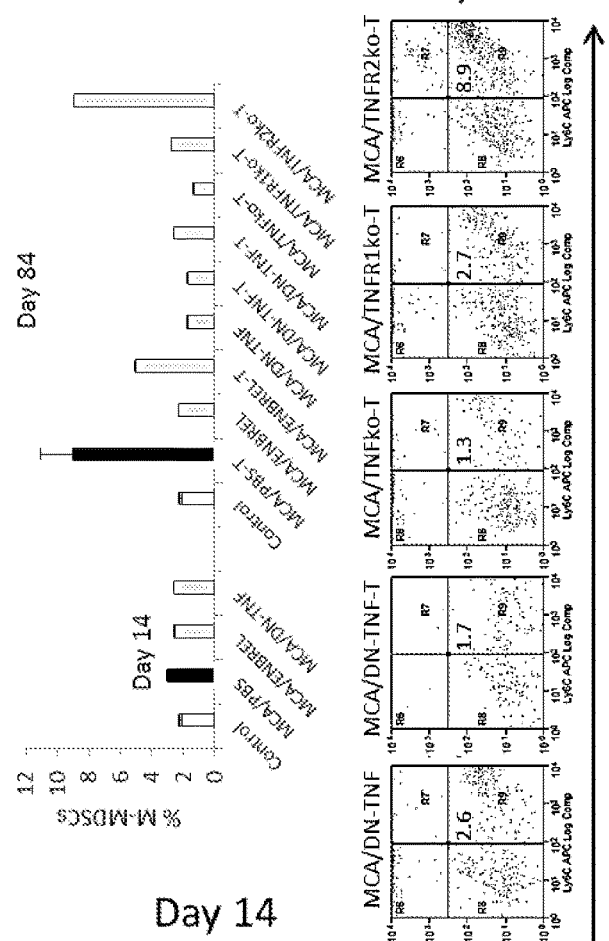
FIGS. 3A-3D. sTNF exclusion with XPRO™ 1595 averts MCA-induced myeloid derived suppressor cell (MDSC) expansion. Similar experimental groups were set up as described in FIG. 1 legend. Both tumor-free and tumor-bearing (T) wild-type mice were examined, including healthy/untreated control (Control); MCA-injected: PBS-treated (tumor-free: MCA/PBS; tumor-bearing: MCA/PBS-T), TNFR2-Fc-treated (tumor-free: MCA/ENBREL; tumor-bearing: MCA/ENBREL®-T), XPRO™ 1595-treated (tumor-free: MCA/DN-TNF; tumor-bearing: MCA/DN-TNF-T; and/or tumor-bearing MCA-injected/TNFko (MCA/TNFko-T), TNFR1ko (MCA/TNFR1ko-T) and TNFR2ko-T (MCA/TNFR2ko-T) mice. Splenocytes were obtained from the listed groups of mice on days 14 (FIGS. 3A, 3B) and/or 84 (FIGS. 3C, 3D) following MCA injection, and stained with fluorochrome-conjugated antibodies to CD11b, Gr1, and Ly6C. Stained splenocytes were analyzed by three-color flow cytometry. The gating/analysis strategy is presented in FIG. 6. $CD11b^+Gr1^{lo/-}Ly6C^{+/hi}$ m monocytic MDSCs (FIGS. 3A, 3B), and $CD11b^+Gr1^{hi}Ly6C^+$ granulocytic MDSCs (FIGS. 3C, 3D) were scored. Dot-plot data present non-granular $Gr1^- Ly6C^+CD11b^+$ (FIG. 3A), and granular $Gr1^+Ly6C^+CD11b^+$ (FIG. 3C) cells. Histograms show individual and mean (2-3 replicates±SD: Control, MCA/PBS-T and DN-TNF-T) percentages of monocytic (FIG. 3B) and granulocytic (FIG. 3D) MDSCs.
Figures 3C, 3D:
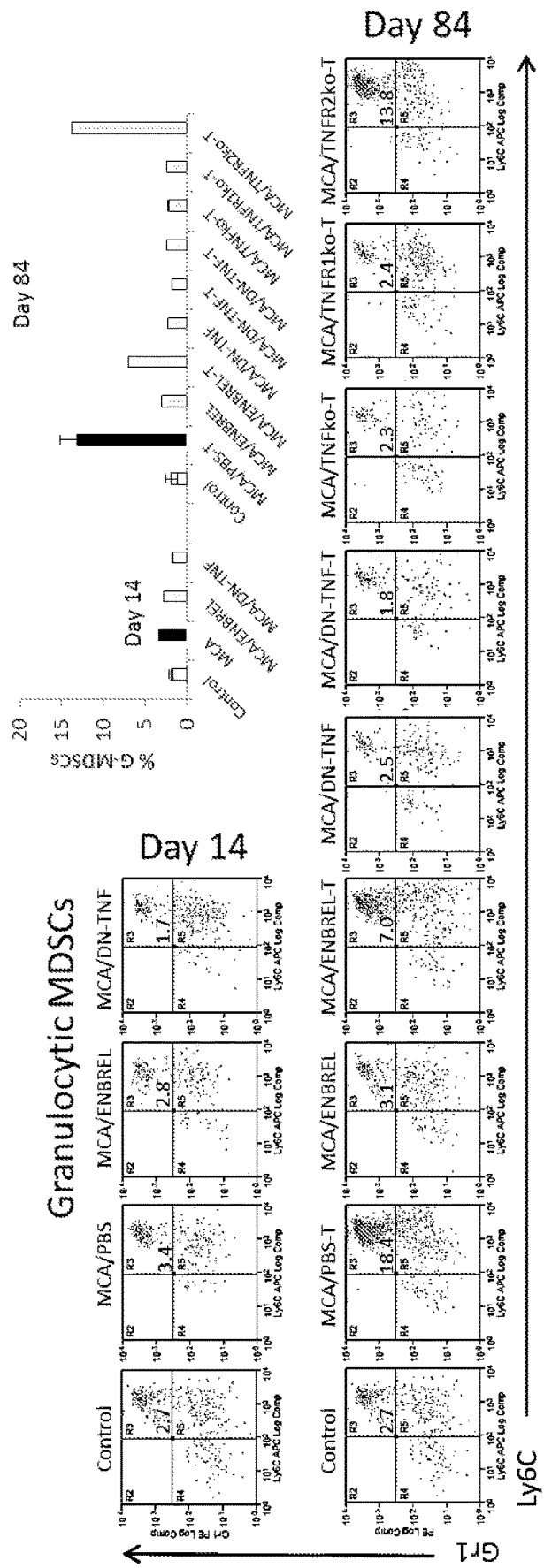
Figure 4A:
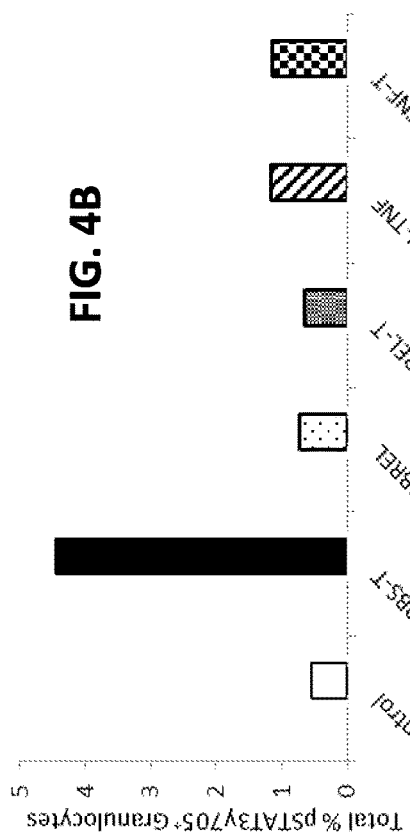
FIGS. 4A-4D. sTNF-sequestration with XPRO™ 1595 prevents MCA-induced activation of STAT3 in myeloid cells. Splenocytes of healthy/untreated control (Control) and MCA-injected/PBS-treated (tumor-bearing: MCA-T), TNFR2-Fc-treated (tumor-free: MCA/ENBREL; and tumor-bearing: MCA/ENBREL-T), and XPRO™ 1595-treated (tumor-free: MCA/DN-TNF; and tumor-bearing: MCA/DN-TNF-T) wild-type mice were obtained on day 84 after MCA injection, and examined by flow cytometry for intracellular presence of the phosphorylated STAT3 y705 (FIGS. 4A, 4B) and STAT3 s727 (FIG. 4C, 4D). The analyses of gated large non-granular mononuclear cells (Monocytes) (FIG. 4A, 4C) and middle-size granular cells (Granulocytes) (FIG. 4B, 4D) were performed as shown in FIG. 8. Data represent total percentages of stained monocytes and granulocytes.
Figure 4B:
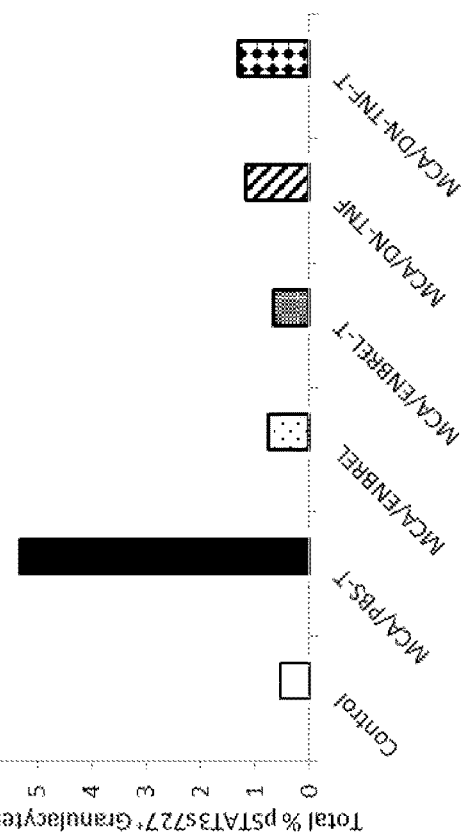
Figure 4C:
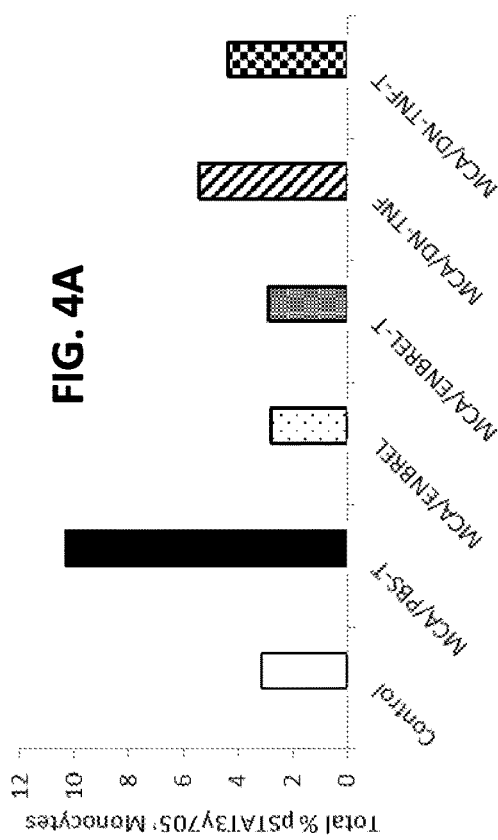
Figure 4D:
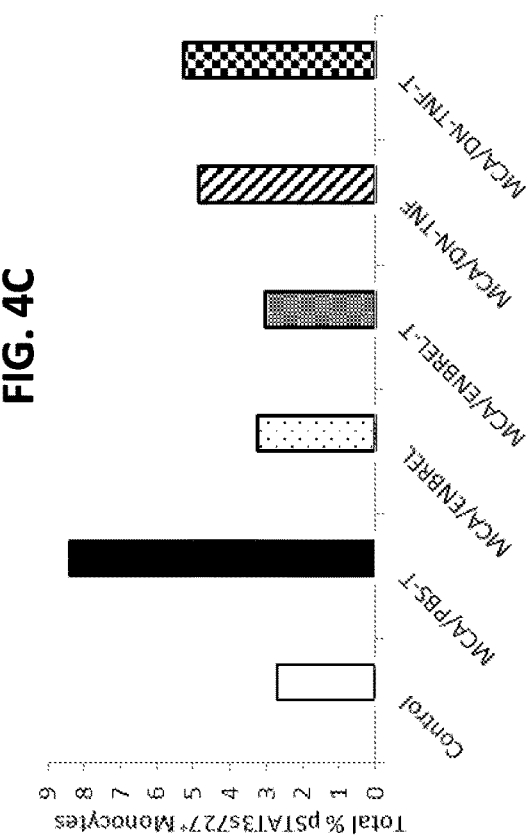

Both carcinogens and cancer induce strong immunosuppression, which may enable cancer development and growth (Wojdani and Alfred, Cancer Res 1984; 44:942-5; Horiguchi et al., Cancer Res 1999; 59:2950-6; Baskic et al., Head & Neck 2013; 35:388-98). MDSCs are a heterogeneous population of immature myeloid cells that strongly suppress major immune functions (Gabrilovich and Nagaraj, Nat Rev Immunol 2009; 9:162-174; Nagaraj and Gabrilovich, Cancer J 2010; 16:348-53). While MDSCs are rare in healthy organisms, their frequency and activity highly increase in cancer-host bone marrow, peripheral lymphoid tissue and tumor. It is believed that MDSCs contribute to tumor immune-escape and failure of immunotherapy. However, MDSC presence and role in chemically-induced carcinogenesis and immunosuppression are unexplored (Nagaraj and Gabrilovich, Cancer J 2010; 16:348-53). Induction of carcinogenesis by MCA injection and/or prevention of carcinogenesis by exclusion of sTNF and/or tmTNF led to changes in the frequency of MDSCs (FIG. 6, FIGS. 3A-3D) and/or macrophages (FIG. 7). MCA-induced increases of monocytic ($CD11b^+Gr1^{lo/-}Ly6C^{+/hi}$, FIGS. 3A, 3B) and granulocytic ($CD11b^+Gr1^{hi}Ly6C^+$, FIGS. 3C, 3D) MDSCs in the spleens of wild-type mice. The increased frequencies of MDSCs were notable at the cancer-initiation stage (day 14: 1.4- and 1.3-fold, respectively), and highly augmented in the established tumor stage (day 84: 6.7- and 6.8-fold, respectively) of MCA-induced carcinogenesis. In contrast, frequency of splenic $F4/80^+$ macrophages did not significantly change after MCA injection (FIGS. 7C, 7D). However, neutralization of both TNF forms by TNFR2-Fc-ENBREL decreased frequencies of both monocytic and granulocytic MDSCs as well as macrophages at both time-points in tumor-free and tumor-bearing MCA-injected mice. Remarkably, sequestration of sTNF by DN-TNF-XPRO™ 1595 invariably and strongly decreased frequencies of monocytic MDSCs, granulocytic MDSCs and macrophages to or below their normal/untreated-control levels, at both time-points, in both tumor-free and tumor-bearing MCA-injected mice. The DN-TNF-induced reductions in MDSC frequencies were more prominent than those induced by ENBREL. Similar decreases of MDSC and macrophage frequencies were observed in MCA-injected tumor-bearing TNF-deficient mice lacking both TNF forms, and TNFR1-deficient mice lacking sTNF-receptor. In sharp contrast to MCA-injected DN-TNF- or ENBREL-treated wild-type and TNF- or TNFR1-deficient mice, and similar to MCA-injected PBS-treated wild-type mice, MCA-injected TNFR2-deficient mice lacking tmTNF-receptor possessed highly increased frequencies of both monocytic and granulocytic MDSCs, and unchanged frequencies of macrophages, relative to healthy/untreated control mice. Surprisingly, $FoxP3^+CD4^+CD25^+$ Treg frequencies were found unchanged in all MCA-injected groups of mice. These data show that MCA induces MDSC expansion during carcinogenesis. Remarkably, they also evidence that sTNF, but not tmTNF, is required for the MCA-induced expansion of MDSCs and maintenance of the macrophage population, and that treatment with the selective sTNF inhibitor DN-TNF-XPRO™ 1595 efficiently prevents MDSC expansion.

Example 5

MCA Induces sTNF-Dependent STAT3 Activation in Myeloid Cells

Figure 6:
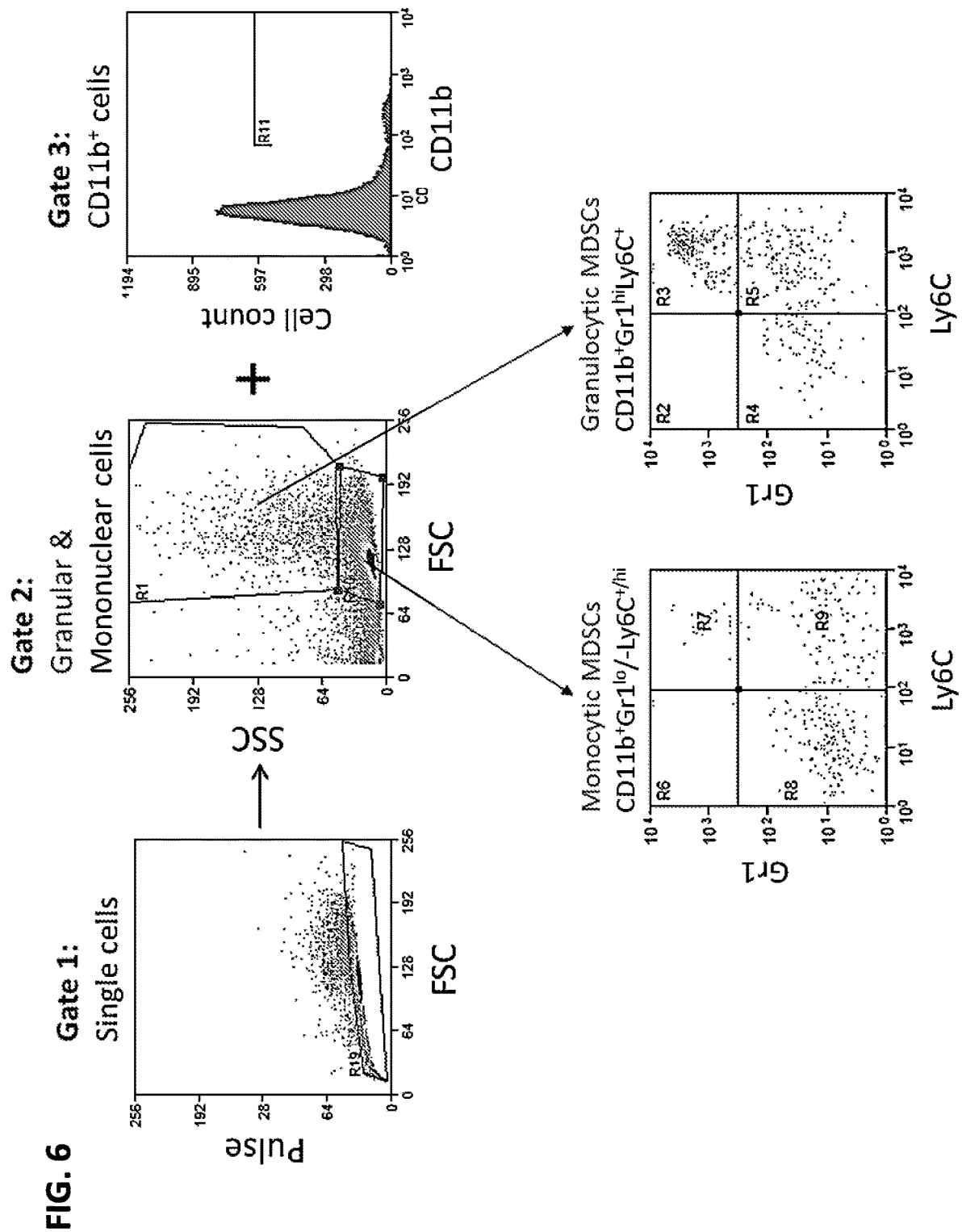
FIG. 6. Gating strategy for three-color flow cytometry analysis of splenic MDSCs. Splenocytes were simultaneously stained with anti-CD11b-FITC, anti-Gr1-PE and anti-Ly6C-APC antibodies or with the corresponding isotype control antibodies and analyzed by flow cytometry as follows. Gate 1: single cells were gated and cell aggregates were excluded. Gate 2: using forward scatter (FSC) and side scatter (SSC), non-granular, mononuclear, and granular cells were gated. Finally, $CD11b^+$ non-granular-mononuclear and granular cells were gated (Gate 3), and analyzed for Gr1 and Ly6 expression.
Figure 8:
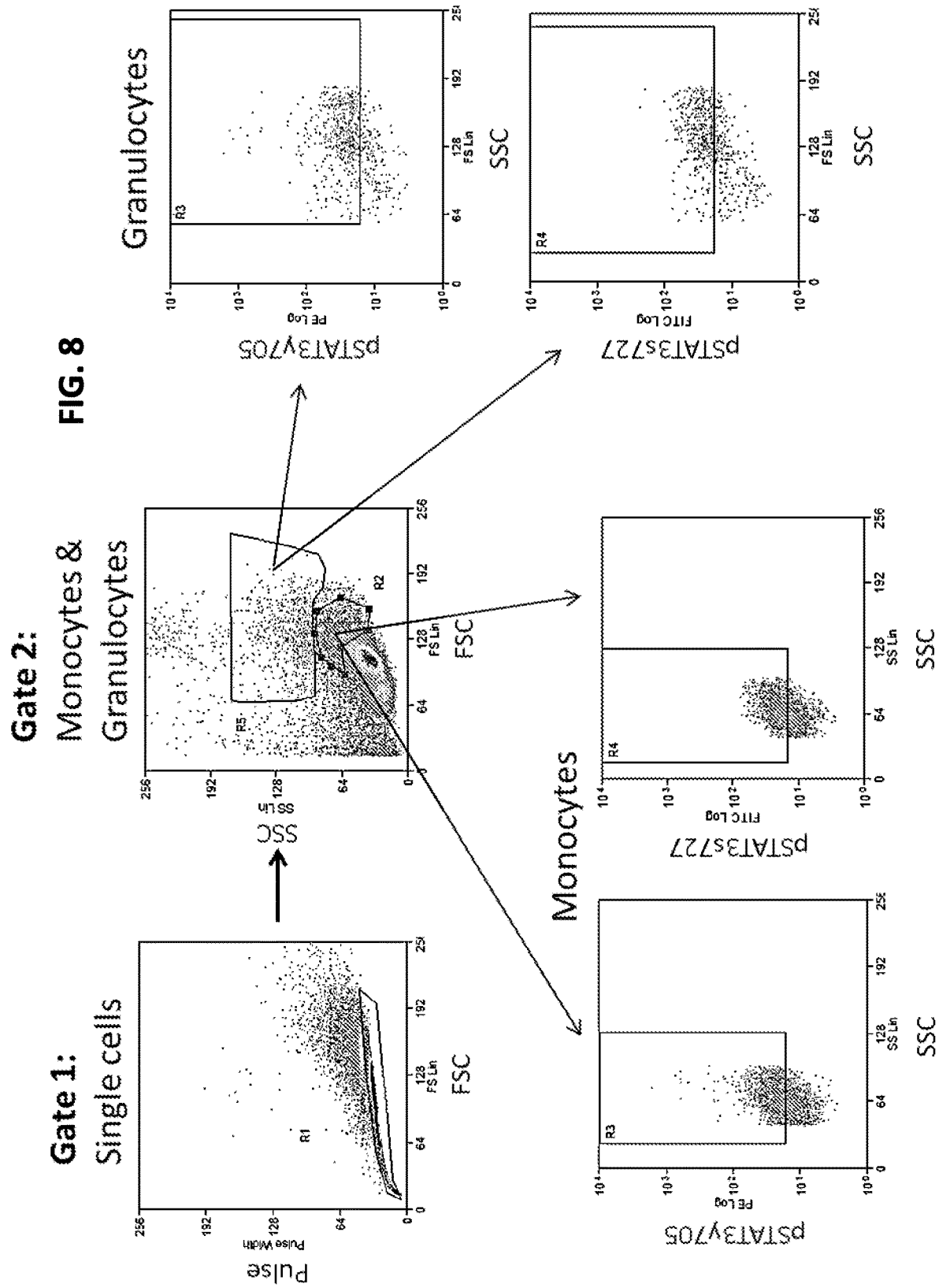
FIG. 8. Gating strategy for STAT3 single-color flow cytometry analysis of splenic monocytes and granulocytes. Splenocytes were fixed, permeabilized, stained with IgG control or anti-pSTAT3 antibodies, and gated similarly to FIG. 6 Gate 1, on single cells; Gate 2, on large non-granular (Monocytes) and granular (Granulocytes) splenocytes. Thus gated leukocytes were examined by single-color flow cytometry for the intracellular expression pSTAT3 y705 and pSTAT3 s727.

STAT3 is a transcription factor that plays an essential role in regulation of MDSC development and function (Nagaraj and Gabrilovich, Cancer J 2010; 16:348-53; Vasquez-Dunddel et al., J Clin Invest 2013; 123:1580-9). Its phosphorylated active form (pSTAT3) is considered a hallmark of MDSCs. To validate the carcinogen-induced sTNF-dependent expansion of MDSCs, it was investigated whether MCA induces sTNF-dependent pSTAT3 in myeloid cells. Splenocytes of healthy/untreated-control and MCA-injected/PBS-, ENBREL- or DN-TNF-treated wild-type mice were harvested on day 84 after MCA injection and examined by flow cytometry for the presence of pSTAT3y705 and pSTAT3s727 residues (FIG. 4). Monocytes and granulocytes were defined by forward scatter (size) and side scatter (granularity), as non-granular/large- and granular/medium-size cells, respectively (FIG. 8). The identities of cell populations were confirmed using their labeling with fluorochrome-conjugated antibodies to Gr-1, CD11b, Ly6C and F4/80 (FIGS. 6 and 7). In control mice, the frequencies of splenic monocytes and granulocytes expressing pSTAT3 were low (FIG. 4). In sharp contrast, frequencies of $STAT3y705^+$ (FIGS. 4A, 4B) and $pSTAT3s727^+$ (FIGS. 4C, 4D) monocytes (FIGS. 4A, 4C) and granulocytes (FIGS. 4B, 4D) were highly and similarly increased in MCA-injected/PBS-treated mice. The MCA-induced increases in $pSTAT3^+$ cell frequencies were prevented in both tumor-free and tumor-bearing mice by TNFR2-Fc-ENBREL or DN-TNF-XPRO™ 1595 treatment. These data show that MCA and/or MCA-induced tumors activate the essential MDSC transcription factor STAT3 in myeloid cells, which parallels and correlates with MDSC expansion. They also show that sTNF is not only important for MCA-induced expansion of MDSCs but also for MCA-induced activation of STAT3 in myeloid cells.

Example 6

MCA Induces and sTNF Inhibition Averts Cell-Mediated Suppression of NK Cell/DC Crosstalk NK-cell/DC crosstalk is a central immunoregulatory mechanism that defines type and extent of innate and adaptive immune responses (Moretta, Nature Rev Immunol 2002; 2:957-64; Cooper et al., TRENDS Immunol 2004; 25:47-52; Walzer et al., Blood 2005; 106:2252-8). It was previously determined that the crosstalk leading to a high Th1 response, which efficiently controls cancer growth, is mainly mediated via cell-to-cell contact and tmTNF (Xu et al., Blood 2007; 109:3333-41; Vujanovic et al., Blood 2010; 116:575-583; Vujanovic, Immunol Res 2011; 50:159-74, Makarenkova et al., J Leukoc Biol 2005; 77:408-13). Carcinogens and tumors suppress NK cells and/or DCs (Horiguchi et al., Cancer Res 1999; 59:2950-6.; Baskic et al., Head & Neck 2013; 35:388-98; Gorelik et al., J Natl Cancer Inst 1981; 67:1317-22; Gabrilovich et al., Cell Immunol 1996; 170:101-10; Gabrilovich et al., Clin Cancer Res 1997; 3:483-90) that may disable NK-cell/DC crosstalk and allow carcinogenesis and tumor growth. Because MCA concomitantly induced sTNF-dependent carcinogenesis, suppression of central immunoregulatory cytokines that are up-regulated in NK-cell/DC crosstalk, and expansion of MDSCs, it was examined whether MDSC-mediated suppression of NK cell/DC crosstalk is an MCA-induced immunosuppression mechanism (FIG. 5). The endogenous NK-cell/DC crosstalk among splenocytes of healthy/untreated-control and MCA-injected/PBS-, ENBREL- and DN-TNF-treated wild-type mice was initially assessed (FIGS. 5A, 5B). Splenocytes were stimulated with IL-2 and LPS, to activate NK cells and DCs, respectively, and promote their crosstalk and IFNγ secretion (Xu et al., Blood 2007; 109:3333-41; Vujanovic et al., Blood 2010; 116:575-583). IL-2/LPS stimulation induced enhanced NK-cell/DC crosstalk and IFNγ secretion in control splenocytes (Control 2) relative to their unstimulated counterpart (Control 1). Both 14 and 84 days after carcinogen injection, the IL-2/LPS-stimulated splenocytes of all MCA-injected mice regardless of treatment, except of DN-TNF-treated tumor-free mice 84 days after MCA, showed significantly decreased Th1 response (FIGS. 5A, 5B). The activity decrease was notably pronounced in splenocytes of ENBREL-treated mice. These findings show that NK cell/DC crosstalk is suppressed throughout MCA-induced carcinogenesis. The enhanced suppression of NK-cell/DC-crosstalk in all ENBREL-treated mice, and lack of suppression in DN-TNF-treated tumor-free mice day 84 after MCA, confirm that endogenous NK-cell/DC crosstalk is mediated by tmTNF (Xu et al., Blood 2007; 109:3333-41; Vujanovic et al., Blood 2010; 116:575-583; Vujanovic, Immunol Res 2011; 50:159-74), and indicate a potential participation of sTNF in MCA-induced suppression.

It was directly assessed whether MCA-induced MDSCs could suppress NK cell/DC crosstalk. In these experiments, the responder cells (Responders) were SCID-mouse splenocytes, which are composed of 50% NK cells, 30% DCs and 20% monocytes/macrophages. The stimulator/suppressor cells (Stimulators/Suppressors) were splenocytes of healthy/untreated (Control), MCA-injected/PBS-treated (tumor-free: MCA/PBS; tumor-bearing: MCA/PBS-T), MCA-injected/ENBREL-treated (tumor-free: MCA/EN; tumor-bearing: MCA/EN-T) and MCA-injected/DN-TNF-treated (tumor-free: MCA/DN; tumor-bearing: MCA/DN-T) wild-type mice, obtained on days 14 and 84 after MCA injection. Responders and stimulators/suppressors, either alone or mixed in 1:1 and 1:3 ratios, were incubated in cell-to-cell contact in the presence of IL-2/LPS, for 24 h. Very similar results were obtained with splenocytes of mice harvested on days 14 (FIG. 5C) and 84 (FIG. 5D) after MCA injection. At both time-points, SCID NK cells and DCs interacted strongly and secreted large amounts of IFNγ (SCID:Control, 1.0:0.0). The reaction was highly increased in a dose-dependent manner by adding to SCID-mouse splenocytes healthy/untreated wild-type-mouse splenocytes, which had low MDSC frequency (FIGS. 3 and 4). Importantly, the observed increases in IFNγ secretion were 6 to 10 fold greater than the responses of the corresponding stimulators/suppressors alone (Control 2, FIGS. 5A, 5B), indicating a possible synergistic cooperation of SCID and healthy/untreated wild-type mouse splenocytes. In contrast, MCA/PBS-mouse splenocytes that contained a large population of MDSCs (FIG. 3) strikingly decreased the SCID-mouse NK cell/DC crosstalk to baseline, on day 14, or below baseline, by day 84. In sharp contrast, MCA/ENBREL-mouse splenocytes, and more prominently MCA/DN-TNF-mouse splenocytes stimulated SCID NK cell/DC crosstalk as measured by IFNγ secretion. While both tumor-free and tumor-bearing MCA/DN-TNF mouse splenocytes that lacked MDSCs (FIG. 3) stimulated SCID-NK-cell/DC crosstalk as strongly as healthy/untreated wild-type splenocytes, MCA/ENBREL-treated mouse splenocytes that had low to moderate amount of MDSCs (FIG. 3) did not. The MCA/ENBREL-splenocytes mediated slightly (day 14) and substantially (day 84) decreased stimulation of SCID-NK cell/DC crosstalk relative to that of healthy/untreated- or MCA/DN-TNF-treated-mouse splenocytes. These findings indicate that MCA and MCA-induced tumor strongly stimulate not only the expansion but also the immunosuppressive activity of MDSCs, which in turn inhibits NK-cell/DC crosstalk. They also suggest that the expansion and immunosuppressive activity of MDSCs are both dependent on sTNF and can be efficiently prevented by DN-TNF-XPRO™ 1595 treatment.

It is disclosed herein that selective exclusion of sTNF by DN-TNF-XPRO™ 1595 treatment or TNFR1-gene deletion, and elimination of both sTNF and tmTNF by ENBREL treatment or TNF-gene deletion strikingly prevented carcinogenesis, decreased tumor growth, and prolonged survival of MCA-injected mice. In sharp contrast, the selective exclusion of tmTNF by TNFR2-gene deletion enhanced the MCA-induced carcinogenesis, as evidenced by increased tumor growth and decreased survival. These findings demonstrate that sTNF is essential, while tmTNF is dispensable, for chemical (MCA)-induced carcinogenesis. The data also suggest that tmTNF, in contrast to sTNF, has a protective role in carcinogenesis.

Notably, DN-TNF treatment or TNF-gene deletion, which exclude sTNF or both tmTNF and sTNF, respectively, almost completely prevented carcinogenesis, whereas ENBREL treatment, which neutralizes not only two TNF forms but also LTα and LTα2β1 (Tracey et al., Pharmacology & Therapeutics 2008; 117:244-79), partially prevented carcinogenesis. These findings indicate that not only tmTNF, but also LTα and/or LTα2β1 could have a protective role in MCA-induced carcinogenesis, which is inhibited by the ENBREL.

Without being bound by theory, the following is a likely scenario for the initiation of carcinogenesis. Carcinogens induce injury and cell necrosis in target tissues. Necrotic cells release damage associated molecular pattern molecules (DAMPs), including heat-shock proteins, high-mobility group box 1 (HMGB1), DNA, RNA, S100 molecules and purine metabolites (Tang et al., Immunol Rev 2013; 249: 158-75). DAMPs induce activation of innate immunity effector cells such as macrophages, DCs and NK cells. These innate immunity effectors release proinflammatory cytokines such as sTNF. The proinflammatory cytokines induce pro-carcinogenic inflammation. In parallel, tissue protective/healing anti-inflammatory and immunosuppressive feedback mechanisms develop. In our study the immunoregulatory cytokines IL-1β, IL-12 and IL-17, which are produced by the activated innate immunity effectors and mediate the effective Th1 and Th17 anticancer immune mechanisms, are unchanged during the initiation of MCA-induced carcinogenesis, but enhanced after exclusion of sTNF by DN-TNF. In the context of carcinogenesis, these findings indicate that the activation of anticancer immune mechanisms might be induced during carcinogenesis, but their expression is down-regulated by sTNF-induced immunosuppressive mechanisms. This is supported by the fact that potentially immunosuppressive cytokine soluble IL-1α is secreted in healthy mice, increased during the initiation of MCA-induced carcinogenesis, and strikingly decreased below its healthy-mouse levels by selective sequestration of sTNF by DN-TNF-α.

IL-1α and IL-1β bind to the same receptors (Apte et al., Cancer Metastasis Rev. 2006; 25:387-408). Both cytokines are produced as 31 kD precursors, which are processed by the proteases calpain and IL-1 converting enzyme, respectively, leading to the generation of 17 kD soluble forms that are released outside of cells. The soluble IL-1β is immunologically active. In contrast, the soluble IL-1α is immunologically inactive. The release of 17 kD IL-1α also lead to the generation of the functional 14 kD IL-1α N-terminal propiece. The IL-1α propiece functions as a transcription factor that activates oncogenes and inhibits tumor-suppressor genes. Although immunologically inactive, secreted IL-1α can function as a growth factor for various malignant cell types, including carcinomas, sarcomas, and B-cell and myeloid-cell leukemias. Without being bound by theory, immunologically inactive soluble IL-1α being capable of binding IL-1 receptors, could block and prevent IL-1 receptors for interacting with the immunologically active forms of IL-1, and thus function as a negative regulator of immune responses.

As IL-1α is overexpressed in cells exposed to chemical carcinogens (Apte et al., Cancer Metastasis Rev 2006; 25:387-408), the disclosed results that the elevated soluble IL-1α levels in MCA-injected mice are strikingly decreased by DN-TNF treatment indicate that sTNF can induce enhanced generation of propiece and soluble IL-1α. As a result, the two upregulated forms of IL-1α could promote malignant transformation of target cells, and mediate growth of newly generated malignant cells and inhibition of IL-1-induced immune responses, respectively. MCA-induced carcinogenesis also caused STAT5 phosphorylation in myeloid cells and expansion and accumulation of MDSCs in the spleen, which were prevented in both tumor-free and tumor-bearing mice by the exclusion of sTNF by DN-TNF-α or ENBREL treatment and/or TNF or TNFR1 gene-deletion, but not by the exclusion of tmTNF by TNFR2 gene-deletion. These findings demonstrate that sTNF upregulates MDSC expansion and accumulation in MCA-induced carcinogenesis. Secreted IL-1α, which can mediate growth and homing of myeloid cells (Apte et al. Cancer Metastasis Rev 2006; 25:387-408; Rider et al. J Immunol 2011; 187:4835-43), could be involved in the MDSC growth and regulation during the carcinogenesis. Our data suggest that sTNF has a central regulatory role in MDSC expansion in carcinogenesis, which could comprise the induction of MDSC growth factors such as IL-1α and/or VEGF and GM-CSF. In parallel with the sTNF-dependent expansion and accumulation of MDSCs in the spleen of MCA-injected mice, a potent sTNF-dependent immunosuppressive mechanism inhibiting the central immunoregulatory mechanism NK cell/DC crosstalk was found. Similar to MDSC expansion, immunosuppressive activity was completely eliminated by sTNF exclusion with DN-TNF treatment in both tumor-free and tumor-bearing mice. As the frequency of other potential immunosuppressive cells, including CD4$^+$CD25$^+$Foxp3$^+$ Treg and F4/80$^+$ macrophages, did not change during the initiation or tumorigenesis phase of MCA-induced carcinogenesis, it is possible that MDSCs are the main mediators of the splenocyte immunosuppression that evolves during carcinogenesis. The MDSC-produced immunosuppressive molecules, especially PGE2, TGFβ and IL-10, are also known as potent suppressants and/or modulators of NK cells and DCs (Harizi Cell. Mol. Immunol., 2013; 10:213-21; Mo et al. Annu. Rev. Immunol 2006; 24:99-146; Moore. Annu. Rev. Immunol. 2001; 19:683-765). Therefore, our findings could indicate that MDSCs potently suppress NK cells and/or DCs, which leads to abrogation of their crosstalk in MCA-induced carcinogenesis. As NK cell/DC crosstalk is the central immunoregulatory mechanism that defines the quality and extent of effective anticancer immune responses, MDSC-mediated immunosuppression could be a mechanism of cancer immune escape in MCA-induced carcinogenesis. The data presented herein document that MCA induced the expansion of MDSCs, suppression of innate-immunity and development of cancer, which all could be prevented by sTNF sequestration or TNFR1 blockade. These findings reveal pivotal role of sTNF in carcinogenesis, and indicate existence of an innate immunity sTNF-TNFR1 axis that down-regulates anticancer immune functions and promote carcinogenesis. The newly defined negative immuno-regulatory axes of the innate immunity complements the immune checkpoints of adaptive immunity CTLA4-B7-1/2 and PD-1-B7-H1, which blockade led to highly promising beneficial effects in patients with advanced cancers (Postow et al. Cancer J., 2012; 18:153-9; Topalian et al. Cur. Opin. Immunol. 2012; 24:207-12; Ott et al. Clin. Cancer Res. 2013; 19:5300-9). Our study indicates that sTNF-TNFR1 axis could be additional immune checkpoint, which targeting could be exploited for cancer prevention and immunotherapy. Clinical application is supported by the efficient prevention of both carcinogen-induced immunosuppression and cancer development with DN-TNF-XPro1595 biologic treatment.

Blockade of other immune checkpoints such as CTLA-4 and PD-1, can be used in combination with a DN-TNF-α for cancer prevention and therapy.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

Example 7

Figure 9A:
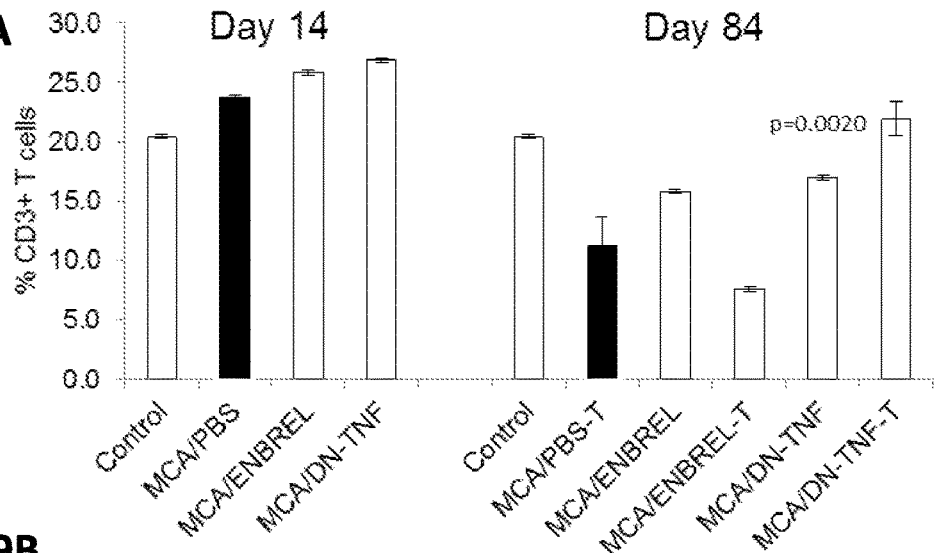
FIGS. 9A-9C. sTNF sequestration with XPRO™ 1595 prevents MCA-induced depletion, and enables expansion of T-helper and T-cytotoxic cells. Both tumor-free and tumor-bearing (T) wild-type mice were examined, including healthy/untreated control (Control); MCA-injected: PBS-treated (tumor-free: MCA/PBS; tumor-bearing: MCA/PBS-T), TNFR2-Fc-treated (tumor-free: MCA/ENBREL®; tumor-bearing: MCA/ENBREL®-T), and XPRO™ 1595-treated (tumor-free: MCA/DN-TNF; tumor-bearing: MCA/DN-TNF-T). Splenocytes were obtained from the listed groups of mice on days 14 and/or 84 following MCA injection, and stained with fluorochrome-conjugated antibodies to CD3, NK1.1, CD4 and CD8. Stained splenocytes were analyzed by three-color flow cytometry. Histograms show individual and mean (2-3 replicates ±SD: Control, MCA/PBS-T and DN-TNF-T) percentages of T cells (CD3$^+$NK1.1$^-$: CD3$^+$.
Figure 9B:
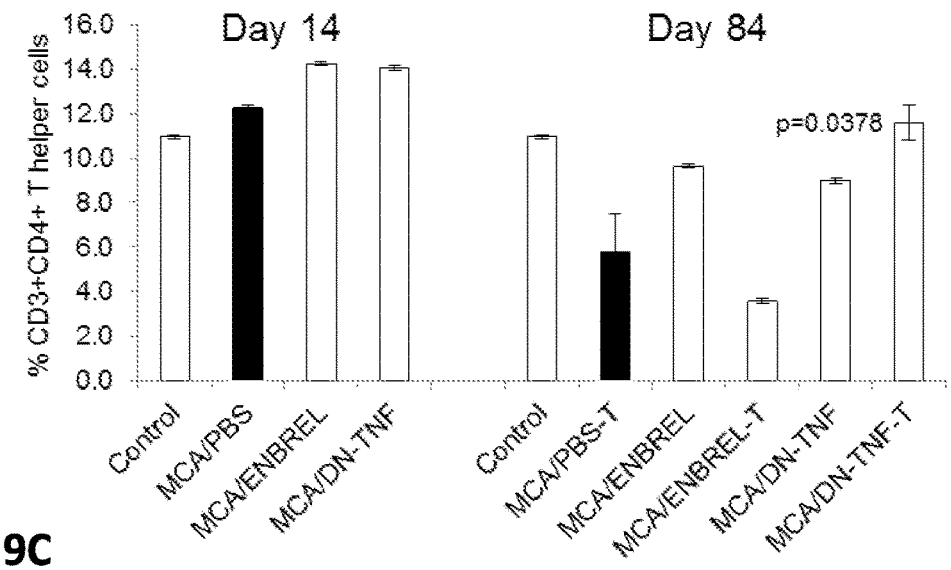
Figure 9C:
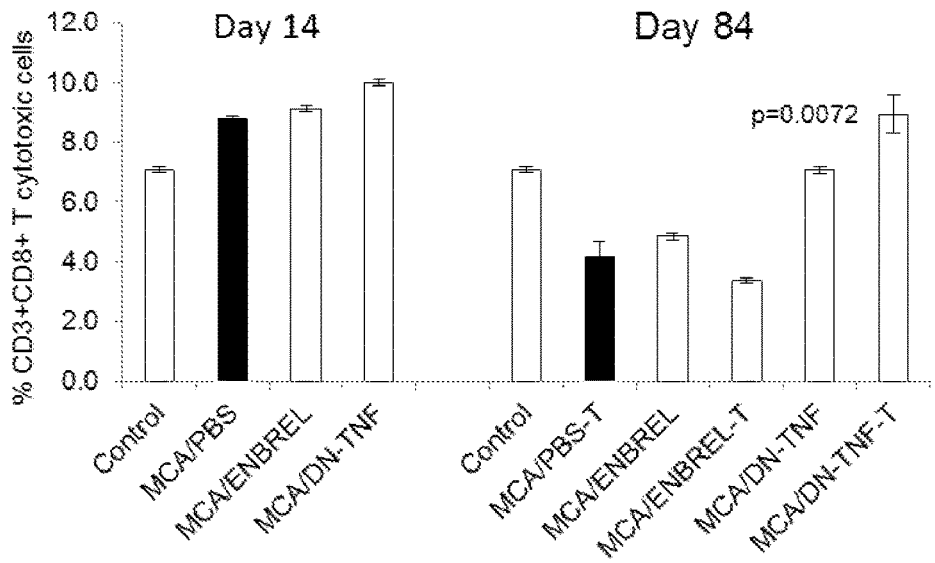

MCA-Induces, ENBREL Promotes and Xpro1595 DN-TNF Averts Depletion and Enables Expansion of T-Helper and T-Cytotoxic Cells Examples 4, 5 and 6 demonstrate that MCA induced and sTNF sequestration averted MDSC expansion and MDSC-mediated suppression of NK cell/DC crosstalk, which is the central immunoregulatory mechanism leading to generation of the potent Th1 innate and T-cell adaptive anticancer immune responses that efficiently control cancer (Moretta, Nature Rev Immunol. 2002; 2:957-64; Cooper et al., TRENDS Immunol 2004; 25:47-52; Walzer et al., Blood 2005; 106:2252-8; Xu et al., Blood 2007; 109:3333-41; Vujanovic et al., Blood 2010; 116:575-583; Vujanovic, Immunol Res 2011; 50:159-74, Makarenkova et al., J Leukoc Biol 2005; 77:408-13). To generate an effective anticancer response, T-helper and T-cytotoxic cells have to be abundant and functional. However, TNF was shown to inhibit tumor-specific T cell responses (Landsberg, et al. Nature 2012; 490:412-416; Donia et al. Cancer Res. 2015; 75:3747-3759). Flow cytometry was used to examine the frequency of CD3$^+$ T cells (FIG. 9A) and their CD3$^+$CD4$^+$ helper (FIG. 9B) and CD3$^+$CD8$^+$ cytotoxic (FIG. 9C) subpopulations in the spleen of wild-type mice either untreated (control) or mice treated for fourteen or eighty-four days with MCA/PBS, MCA/ENBREL (ENBREL neutralizes both tmTNF and sTNF, and LTα), or DN-TNF Xpro1595 (DN-TNF, specifically sequesters sTNF). On day 14 after MCA injection (an early stage of carcinogenesis), the frequency of T cells and their subpopulations were increased in all mice receiving MCA, but these increases tended to be more pronounced after ENBREL (CD4$^+$ cells only) and especially DN-TNF (both CD4$^+$ and CD8$^+$ cells) treatments. These findings indicated that MCA (for example, the MCA-induced immunogenic malignant cells) initially induces expansion of both T-helper and T-cytotoxic cells, which was further promoted by TNF neutralization. On day 84 after MCA injection, the frequencies of T cells and their subpopulations were strongly decreased in MCA/PBS treated mice, slightly decreased in MCA/ENBREL-treated tumor-free (MCA/ENBREL) mice, and most prominently decreased in MCA/ENBREL-treated tumor-bearing (MCA/

ENBREL-T) mice. In contrast, MCA/DN-TNF-treated tumor-free mice (MCA/DN-TNF) showed similar frequency of T cells as the untreated control mice. In MCA/DN-TNF-treated tumor-bearing mice (MCA/DN-TNF-T), the frequencies of T-cells and their subpopulations were notably higher than those in MCA/DN-TNF-treated tumor-free or control mice, and significantly higher than those in MCA/PBS-treated mice (CD3$^+$: p=0.0020; CD3$^+$CD4$^+$: 0.0038; and CD3$^+$CD8$^+$, 0.0072).

These findings indicated that MCA- and tumor-induced sTNF caused depletion of both T-helper and T-cytotoxic cells, which could not only be prevented, but also the expansion of T-helper and T-cytotoxic cells could be promoted in tumor-bearing mice by DN-TNF treatment, which neutralized sTNF while preserving tmTNF. Because ENBREL deepened, while Xpro1595 DN-TNF averted the MCA-induced depletion of T cells in tumor-bearing mice, it is possible that tmTNF and/or lymphotoxin protect T cells from sTNF-mediated depletion.

Example 8

Figure 10:
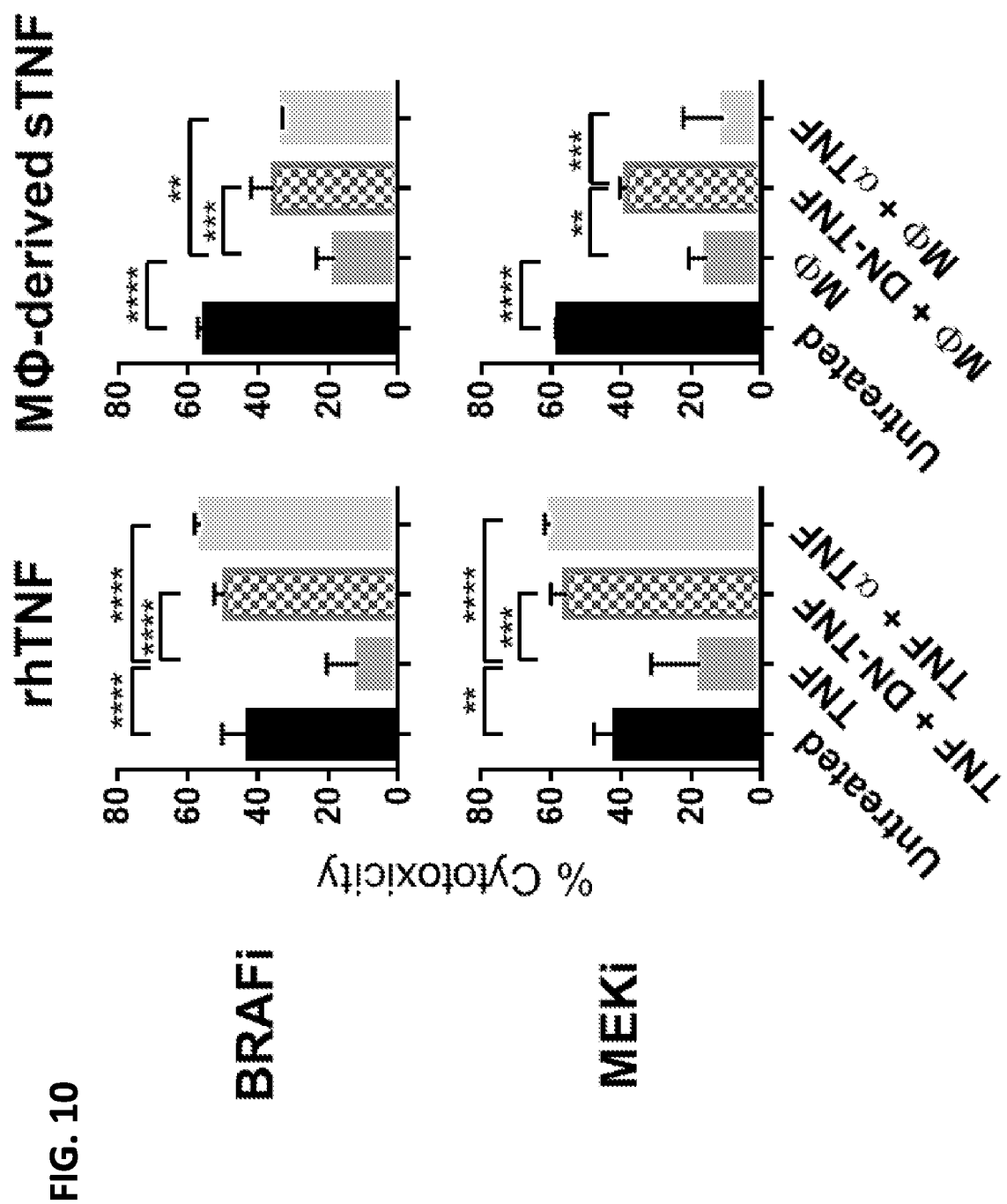
FIG. 10. XPRO™ 1595 effectively blocks sTNF-induced resistance to BRAF and MAPK kinase (MEK) inhibitors in human melanoma cell lines harboring the BRAF$^{V600E}$ mutation. SK-Mel-37, a human melanoma cell line containing the BRAF$^{V600E}$ mutation, was exposed to recombinant human TNF (rhTNF) or M1 macrophage (MΦ)-secreted sTNF in absence (TNF) or presence of XPRO™ 1595 or TNF blocking antibody (TNF+DN-TNF and TNF+αTNF, respectively) for 20 h at 37° C. Subsequently, the sensitivity of cells to BRAF (PLX4720) and MEK (selumetinib) inhibitors (BRAFi and MEKi, respectively), and their sTNF-mediated induction of BRAFi and MEKi resistance were tested using the MTT (3-(4,5-dimethylthiazol-2-yl)-2,5-diphenyltetrazolium bromide) viability assay. Tests were performed in quadruplicates. Mean values and SD are shown for each response. * $p \leq 0.05$.

DN-TNF Blocks sTNF-Induced BRAF and MEK Inhibitor Resistance in BRAF-Mutant Melanoma It has been proposed that TNF is an important factor associated with acquired BRAF-mutant melanoma resistance to MAPK pathway inhibitors (MAPKi) (Smith, M. P. et al. *Cancer Discov.* 2016, 4: 1214-1229; Lehraiki, A. et al. *Cell Discov,* 2015, 1: 15030). For example, it has been shown that MAPKi therapies lead to increased numbers of tumor-associated macrophages and elevated expression of TNF in all of the BRAF inhibitor (BRAFi)-resistant melanoma patient lesions tested, and macrophage-derived (not tumor-derived) TNF were implicated as an important melanoma growth factor associated with resistance to MAPKi. A strategy to specifically target and block TNF-induced resistance to MAPKi would be beneficial. DN-TNF was tested in vitro for the ability to mitigate sTNF-induced melanoma resistance to BRAF and MEK inhibitors (BRAFi and MEKi, respectively). Recombinant and macrophage-secreted sTNF consistently showed a strong inhibitory effect on BRAFi (PLX4720)- and MEKi (selumetinib)-mediated cytotoxicity. These effects were effectively alleviated by DN-TNF, as well as anti-TNF antibodies which non-specifically block both sTNF and tmTNF (FIG. 10). These studies demonstrate that combining DN-TNF, a selective sTNF antagonist, with small molecule inhibitors of BRAF$^{V600E}$ and MEK can be an effective strategy to treat BRAF$^{V600E}$ mutant melanoma.

We claim:

1. A method for inhibiting the development of, or treating a tumor in a subject, comprising administering to a subject a therapeutically effective amount of a dominant negative tumor necrosis factor (DN-TNF)-α protein and/or a nucleic acid encoding the DN-TNF-α protein, thereby inhibiting the development of the tumor in a subject.

2. The method of claim 1, wherein the subject has a benign tumor, and wherein inhibiting development of the tumor comprises inhibiting conversion of the benign tumor to a malignant tumor.

3. The method of claim 1, wherein inhibiting the development of the tumor comprises inhibiting an immunosuppressive response to the tumor in the subject.

4. The method of claim 3, wherein inhibiting the immuosuppressive response comprises the inhibiting the number and/or function of myeloid derived suppressor cells (MDSCs).

5. The method of claim 3, wherein inhibiting the immunosuppressive response comprises inhibiting production of an immunosuppressive cytokine.

6. The method of claim 5, wherein the cytokine is soluble interleukin (IL)-1α, TGFβ or IL-10.

7. The method of claim 3, wherein inhibiting the immunosuppressive response comprises inhibiting depletion and/or exhausting of T-helper and T-cytotoxic cells.

8. The method of claim 1, wherein inhibiting the development of the tumor comprises stimulating an immune response to the tumor in the subject.

9. The method of claim 8, wherein stimulating the immune response comprises stimulating Th1 immune response, stimulating a Th17 immune response, promoting natural killer (NK)-cell/dendritic cell (DC) cross-talk, promoting T-helper and T-cytotoxic cell expansion, and/or increasing secretion of IL-1β, IL-12, IFNγ and/or IL-17.

10. The method of claim 1, wherein inhibiting the development of the tumor comprises reducing tumor size and number as compared to a control.

11. The method of claim 10, wherein the control is an untreated subject or a subject treated with a carrier.

12. The method of claim 1, wherein the DN-TNF-α polypeptide comprises the amino acid sequence of SEQ ID NO: 2.

13. The method of claim 1, wherein the tumor is a colon cancer, lung cancer, prostate cancer, breast cancer, Kaposi's sarcoma liver cancer, head and neck cancer, esophageal cancer, gastric cancer, renal cancer, ovarian cancer, pancreatic cancer, brain cancer, or melanoma.

14. The method of claim 1, further comprising administering to the subject an additional agent for the treatment of the tumor.

15. The method of claim 14, wherein the additional agent is surgery, radiation, or a chemotherapeutic agent.

16. The method of claim 14, wherein the additional agent is an anticancer vaccine comprising MUC-1 or prostate specific antigen (PCA), and wherein the tumor is colon polyps or prostate precancerous hyperplastic dysplasia, respectively.

17. The method of claim 14, wherein the additional agent is a monoclonal antibody.

18. The method of claim 17, wherein the monoclonal antibody is an anti-programmed death (PD)-1 antibody, an anti-programmed death ligand (PD-L)1 antibody, an anti-programmed death ligand PD-L2 antibody, an anti-lymphocyte activation gene (LAG)3 antibody, an anti-T cell immunoglobulin and mucin protein (TIM)-3 antibody, an anti-T cell immunoreceptor with Ig and ITIM domains (TIGIT), or an anti-cytotoxic T-lymphocyte-associated protein (CTLA)-4 antibody.

19. The method of claim 14, wherein the additional agent is a vaccine.

20. The method of claim 19, wherein the vaccine is a) a dendritic-cell-anti-cancer vaccine; b) a poxviral vaccine; or c) a Toll-Like Receptor Ligand (TLR-L) vaccine.

21. The method of claim 14, wherein the additional agent is a) a cytokine, b) adoptive immunotherapy, or c) a ligand.

22. The method of claim 21, wherein the additional agent is the cytokine, and wherein the cytokine is interferon (IFN)α, interleukin (IL)-2, IL-7, IL-15, SCF, GM-CSF or Flt3-ligand.

23. The method of claim 21, wherein the additional agent is the adoptive immunotherapy, and wherein the adoptive immunotherapy comprises natural killer (NK) cells, T cells and stem cells.

24. The method of claim 14, wherein the additional agent simulates CD137 (4-1BB), CD40 or OX40.

25. The method of claim 24, wherein the additional agent is a monoclonal antibody.

* * * * *